(12) United States Patent
Kotani et al.

(10) Patent No.: US 7,491,381 B2
(45) Date of Patent: Feb. 17, 2009

(54) METHOD OF EVALUATING COMPOUND EFFICACIOUS IN TREATING OBESITY

(75) Inventors: Hidehito Kotani, Tsukuba (JP); Hiraku Itadani, Tsukuba (JP); Hiromits Araki, Kitakyushu (JP); Kazuhiko Takahashi, Tsukuba (JP); Hiroaki Suwa, Tsukuba (JP); Nao Odagiri, Hirosaki (JP); Tsutomu Kobayashi, Ushiku (JP)

(73) Assignee: Banyu Pharmaceutical Co., Ltd. (JP)

( * ) Notice: Subject to any disclaimer, the term of this patent is extended or adjusted under 35 U.S.C. 154(b) by 203 days.

(21) Appl. No.: 10/564,311

(22) PCT Filed: Jul. 9, 2004

(86) PCT No.: PCT/JP2004/009834

§ 371 (c)(1),
(2), (4) Date: Jan. 11, 2006

(87) PCT Pub. No.: WO2005/005665

PCT Pub. Date: Jan. 20, 2005

(65) Prior Publication Data

US 2006/0148739 A1 Jul. 6, 2006

(30) Foreign Application Priority Data

Jul. 11, 2003 (JP) ............... 2003-196154

(51) Int. Cl.
- *C12Q 1/68* (2006.01)
- *C12Q 1/00* (2006.01)
- *G01N 33/53* (2006.01)
- *A61K 49/00* (2006.01)
- *C12N 5/00* (2006.01)

(52) U.S. Cl. ............... 424/9.1; 424/9.2; 435/4; 435/6; 435/7.72; 435/375

(58) Field of Classification Search ............ 435/6, 435/91.1, 91.31, 4, 7.72, 375; 530/300, 350; 424/9.1, 9.2; 536/23.1, 23.2, 24.5

See application file for complete search history.

(56) References Cited

FOREIGN PATENT DOCUMENTS

| WO | WO 02/44320 A2 | 6/2002 |
|---|---|---|
| WO | WO 02/099068 | 12/2002 |
| WO | WO 2004/013347 | * 2/2004 |
| WO | WO 2005/030985 | 4/2005 |

OTHER PUBLICATIONS

Moon, Y-A. et al., J. Biol. Chem., vol. 276, No. 48, pp. 45,358-45,366 (2001).*
Matsuzaka, T., et al.,J. Lipid Res., vol. 43, pp. 911-920 (2002).*
Pan, D.A. et al, J. Clin. Invest., vol. 96, pp. 2802-2808 (1995).*
Suneja, S. K., et al., "Enzyme Site-Specific Changes in Hepatic Microsomal Fatty Acid Chain Elongation in Streptozotocin-Induced Diabetic Rats", Biochimica et Biophysica Acta, vol. 1042, pp. 81-85 (1990).
Elbashir, S. M., et al., "Duplexes of 21-Nucleotide RNAs Mediate RNA Interference in Cultured Mammalian Cells", Nature, vol. 411, pp. 494-498 (2001).
Higuchi, H., et al., "Functional Inhibition of the p75 Receptor Using a Small Interfering RNA", Biochemical and Biophysical Research Communications, vol. 301, pp. 804-809 (2003).
Harborth, J., et al., "Identification of Essential Genes in Cultured Mammalian Cells Using Small Interfering RNAs", Journal of Cell Science, vol. 114, pp. 4557-4565 (2001).
Inagaki et al., Biosci. Biotech. Biochem., vol. 66 (2002), pp. 613-621, "Identification and expression of a rat fatty acid elongase involved in biosynthesis . . . ".
Memon et al., Diabetes, vol. 48 (1999), pp. 121-127, "Regulation of putative fatty acid transporters and Acyl-CoA synthetase in liver . . . ".
Angulo, N. Eng. J. Med., vol. 346 (2002), pp. 1221-1231, "Nonalcoholic fatty liver disease".
The Merck Manual (15th ed.), Chapters 66, 67, and 69 (1987).
The Merck Manual (15th ed.), Chapter 79 (1987).

* cited by examiner

*Primary Examiner*—Jane Zara
(74) *Attorney, Agent, or Firm*—John David Reilly; Catherine D. Fitch

(57) ABSTRACT

Examination of obesity or emaciation is performed based on expression levels of LCE gene or protein in a test tissue or a test cell or a polymorphism of the gene. Evaluation of compounds including screening of therapeutic agents for obesity or emaciation is performed utilizing the nature of LCE gene or protein.

4 Claims, 22 Drawing Sheets

(a)

(b)

(a)

(b)

(a)

(b)

(a)

(b)

(a)

(b)

(c)

(a)

(b)

(c)

(a)

(b)

(a)

(b)

(c)

(a)

(b)

(a)

(b)

(c)

(a)

Body weight (b)

e-WAT weight (c)

Liver LCE mRNA (a)

(b)

METHOD OF EVALUATING COMPOUND EFFICACIOUS IN TREATING OBESITY

This application is the National Stage of International Application No. PCT/JP2004/009834, filed on Jul. 9, 2004, which claims the benefit of JP Application No. JP2003-196154 filed Jul. 11, 2003.

TECHNICAL FIELD

The present invention relates to a method of evaluating compounds which are effective for treatment or prevention of obesity using LCE (long chain fatty acyl elongase) gene or protein. The invention further relates to an examination method for obesity using the gene or protein.

BACKGROUND ART

Obesity is a risk factor for numerous adult diseases including hypertension, diabetes, hyperlipidemia and ischemic heart disease. Since most of these are chronic conditions, they are expected to lead to rising medical costs and to create serious problems for society.

Anti-obesity drugs are being developed for prevention, and currently several appetite suppressors and lipid absorption inhibitors are being used in the clinic. Some of the known target molecules in anti-obesity research include leptin, PPARγ and neuropeptide Y, but because of the huge variety of causes for obesity, it is desirable to focus on molecules having different action mechanisms as targets for future drug development.

Proper diagnosis of obesity and its causes is essential for appropriate treatment thereof, and therefore identification of a convenient and high-precision obesity marker has been desired. With the discovery in recent years that the effects of administered drugs are partially dependent on patient genotypes including genetic polymorphism, it has become a goal to establish examination methods and diagnostic markers on the molecular level for clinical trials at the drug development stage, for so-called "tailor-made medicine".

Biosynthesis of fatty acids is mediated by acetyl CoA carboxylase and fatty acid synthases. LCE (Accession No. NM_024090 (human; SEQ ID NO: 1); NM_130450 (mouse; SEQ ID NO: 2)) is one such fatty acid synthase, and in the fatty acid synthesis pathway in which synthesis is initiated on the substrate acetyl CoA, LCE is known to catalyze elongation of the carbon chains primarily of C12 and longer fatty acids, including myristic acid from lauric acid, palmitic acid from myristic acid, stearic acid from palmitic acid and vaccinic acid from palmitoleic acid (J. Biol. Chem., 276(48), 45358-45366(2002); Non-patent document 1).

For example, WO02/44320 (Patent document 1) teaches that ELG5 (LCE) exhibits activity as an elongase on polyunsaturated fatty acid (PUFA) substrates. It also describes a connection between elongases and diseases such as diabetes, citing a report showing that elongase activity is accelerated in the livers of STZ-induced diabetic rat models (Suneja et al., 1990, Biochem. Biophys. Acta, 1042:81-85; Non-patent document 2).

It has also been reported that feeding of mice alters expression levels of mouse FACE (LCE) (Matsuzaka T. et al., J. Lipid Res., 43(6): 911-20 (2002); Non-patent document 3).

Patent document 1: WO02/44320
Non-patent document 1: J. Biol. Chem., 276(48), 45358-45366(2002)
Non-patent document 2: Suneja et al., 1990, Biochem. Biophys. Acta, 1042:81-85
Non-patent document 3: Matsuzaka T. et al., J. Lipid Res., 43(6): 911-20 (2002)

DISCLOSURE OF THE INVENTION

Problems to be Solved by the Invention

However, these documents do not disclose data that directly indicate a connection between LCE and obesity, and have nowhere shown that a crucial role is perfumed by LCE elongase activity on saturated fatty acids.

In light of the circumstances of the prior art as explained above, it is an object of the present invention to elucidate the direct relationship between LCE and obesity in order to provide an examination method for obesity or emaciation which permits judgment to be made on the molecular level, and examining agents for obesity and emaciation which employ such molecules. It is another object to provide a method of evaluating compounds to allow screening of therapeutic and diagnostic agents for obesity or emaciation. It is yet another object to provide a method for inhibiting fat synthesis and preventing obesity.

Means for Solving the Problems

As a result of much diligent research directed toward achieving the aforestated objects, the present inventors discovered a fixed correlation between weight change and LCE expression, and thereupon completed the present invention.

Specifically, the present invention provides the following methods of evaluating compounds effective for treatment or prevention of obesity, (1) to (4).

(1) A method of evaluating compounds which are effective for treatment or prevention of obesity, characterized by comprising a step in which a test compound is administered to or contacted with a test animal or a test cell, and a step in which it is confirmed whether or not said test compound regulates expression levels of LCE gene or a gene which is functionally equivalent to said gene, in said test animal or test cell.

(2) A method of evaluating compounds which are effective for treatment or prevention of obesity, characterized by comprising a step in which a test compound is contacted with a test animal or a test cell possessing a fusion gene comprising an expression regulatory region of LCE gene and a reporter gene, and a step in which expression of said reporter gene in said test animal or test cell is assayed.

(3) A method of evaluating compounds which are effective for treatment or prevention of obesity, characterized by comprising a step in which a test compound is contacted with LCE protein and a step in which it is confirmed whether or not said test compound exhibits an effect on the activity of said protein.

(4) A method of evaluating compounds which are effective for treatment or prevention of obesity, characterized by comprising a step in which a test compound is contacted with a plurality of elongase proteins including LCE, a step in which the activities of said plurality of elongase proteins are assayed, and a step in which test compounds are selected which inhibit LCE activity among said plurality of elongase proteins.

Also encompassed within the scope of the invention is an agent for treatment or prevention of obesity which contains as active ingredient a compound obtained by the method of evaluating compounds effective for treatment or prevention of obesity, according to the invention as described above.

The invention further provides a method of inhibiting fat synthesis characterized by inhibiting LCE fatty acid synthesis activity. The means for inhibiting LCE fatty acid synthesis activity is not particularly restricted, but preferably involves inhibition by RNAi (RNA interference). The RNAi may be accomplished by using one or more siRNA (small interfering RNA) selected from the group consisting of siRNA consisting of the nucleic acids of SEQ ID NOs: 13 and 14, siRNA consisting of the nucleic acids of SEQ ID NOs: 15 and 16, siRNA consisting of the nucleic acids of SEQ ID NOs: 17 and 18, siRNA consisting of the nucleic acids of SEQ ID NOs: 19 and 20, siRNA consisting of the nucleic acids of SEQ ID NOs: 21 and 22, siRNA consisting of the nucleic acids of SEQ ID NOs: 23 and 24, siRNA consisting of the nucleic acids of SEQ ID NOs: 25 and 26, siRNA consisting of the nucleic acids of SEQ ID NOs: 27 and 28, siRNA consisting of the nucleic acids of SEQ ID NOs: 29 and 30, siRNA consisting of the nucleic acids of SEQ ID NOs: 31 and 32, siRNA consisting of the nucleic acids of SEQ ID NOs: 33 and 34, siRNA consisting of the nucleic acids of SEQ ID NOs: 35 and 36, siRNA consisting of the nucleic acids of SEQ ID NOs: 37 and 38, siRNA consisting of the nucleic acids of SEQ ID NOs: 49 and 50, siRNA consisting of the nucleic acids of SEQ ID NOs: 51 and 51, and siRNA consisting of the nucleic acids of SEQ ID NOs: 53 and 54, and especially siRNA consisting of the nucleic acids of SEQ ID NOs: 23 and 24 are preferably used.

The invention further provides a method for treating or preventing obesity, characterized by inhibiting LCE fatty acid synthesis activity using RNAi. There is no particular restriction on the means for inhibiting LCE fatty acid synthesis activity, but it preferably involves inhibition by RNAi. The RNAi is preferably accomplished using the siRNA mentioned above, and preferably siRNA consisting of the nucleic acids of SEQ ID NOs: 23 and 24 are used.

The invention still further provides the following obesity examination methods (1) to (4).

(1) A method of examining obesity characterized by assaying an expression level and a change in expression levels of LCE gene in a test tissue or a test cell.

(2) A method of examining obesity characterized by assaying an expression level and a change in expression level of LCE protein in a test tissue or a test cell.

(3) A method of examining obesity characterized by detecting a polymorphism in LCE gene in a test tissue or a test cell.

(4) A method of examining obesity characterized by detecting expression or activity of a protein which affects expression of LCE gene through interaction with LCE protein.

The invention still further provides siRNA characterized by being consisting of the nucleic acids of SEQ ID NOs: 23 and 24, as well as an LCE expression inhibiting agent, a fatty acid synthesis inhibiting agent and a therapeutic or preventing agent for obesity characterized by comprising the siRNA.

EFFECT OF THE INVENTION

By the method of evaluating compounds of the present invention, it has become possible to elucidate the direct relationship between LCE and obesity, and provide an examination method for obesity or emaciation which permits judgment to be made on the molecular level, as well as examining agents for obesity and emaciation which employ such molecules. It has also become possible to provide a method for evaluating compounds to allow screening of therapeutic and diagnostic agents for obesity or emaciation, as well as to provide a method for inhibiting fat synthesis and preventing obesity.

BEST MODE FOR CARRYING OUT THE INVENTION

Figure 1:
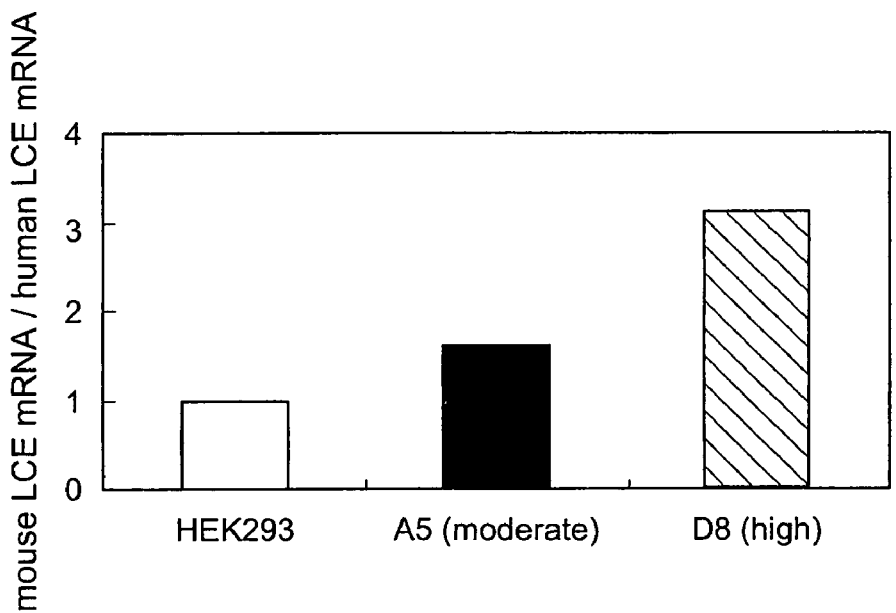
FIG. 1 is a graph showing (a) LCE mRNA expression and (b) LCE activity in cells forced to express LCE. HEK293 represents non-treated cells, A5 represents LCE moderately-expressing cells and D8 represents LCE highly-expressing cells.
Figure 1:
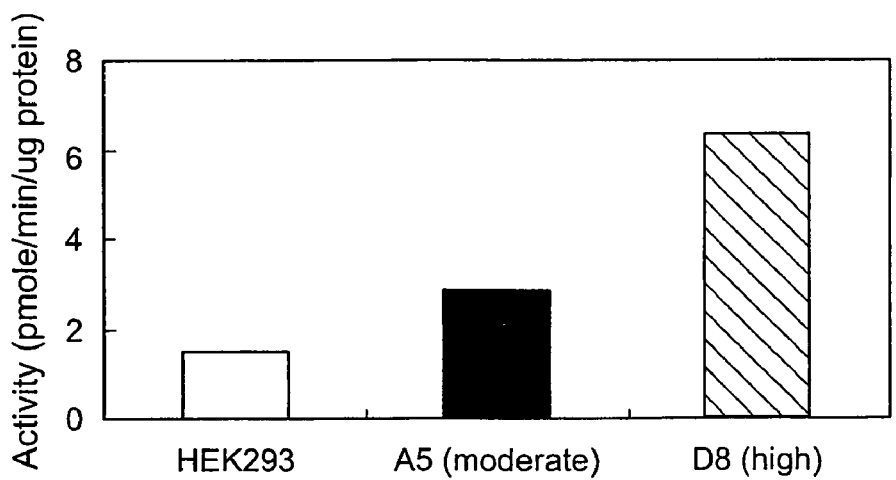

Preferred modes of the invention will now be explained in detail.

"Expression level" according to the invention refers to the absolute or relative amount of transcription product of LCE gene. The term "gene" includes both DNA and mRNA. When the target of expression detection is the protein, the "expression level" refers to the absolute or relative amount of translation product of LCE gene.

A "test animal" according to the invention is not particularly restricted in terms of species so long as it is an animal that can be used for evaluation of the compound, and specifically there may be mentioned mouse, rat, guinea pig, rabbit, dog, monkey and the like.

The type of "test tissue" according to the invention is not particularly restricted so long as it is a tissue which can be extracted from the body for examination of obesity or emaciation, but from the standpoint of readily reflecting effects on obesity or emaciation it is preferably liver tissue, adipose tissue, muscle tissue or blood tissue. From the standpoint of facilitating isolation of the tissue, it is most preferably blood tissue among the above tissues. There are no particular restrictions on the animal species from which the tissue is taken, but human tissue is preferred since the major purpose of the invention will be for human clinical use.

The type of "test cells" according to the invention are also not particularly restricted so long as they are cells that can be extracted from the body for examination of obesity or emaciation, but from the standpoint of readily reflecting effects on obesity or emaciation they are preferably hepatocytes, adipocytes (white adipocytes, brown adipocytes, etc.), muscle cells (myoblasts, skeletal muscle cells, smooth muscle cells, etc.), pancreatic cells (islet cells, etc.) or hemocytes. There are no particular restrictions on the animal species from which the cells are derived, but human cells are preferred since the major purpose of the invention will be for human clinical use.

"Obesity" according to the invention includes not only general obesity as defined by an excess accumulation of adipose tissue, but also "adiposity" associated with complications such as diabetes or hypertension, or visceral fat. "Obesity" according to the invention may also refer to a state of increased body weight relative to an original body weight, in the case of body weight control by administration of a drug or the like.

The term "examination" used according to the invention includes not only simple discernment of obesity or emaciation but also "prognosis" regarding future obesity or emaciation.

"Elongase activity" according to the invention means activity of elongating carbon chains of fatty acids or fatty acyl-CoA.

(1) Method of Evaluating Compounds Effective for Treatment or Prevention of Obesity A method of evaluating compounds which are effective for treatment or prevention of obesity will now be explained. By administering or contacting a test compound with a test animal or a test cell and measuring the resulting variation in LCE gene expression or contacting a test compound with LCE protein and examining the effect on the protein activity, it is possible to evaluate the test compound.

Specifically, it is thought that test compounds will include those which act on cells or tissues to normalize or control LCE gene expression levels or LCE protein activity, thereby helping to normalize mechanisms that contribute to obesity, such as controlling fat accumulation and appetite. Thus, the evaluation method described below allows evaluation of compounds which are effective for treatment or prevention of obesity.

(A) Evaluation Method Using LCE Gene Expression Level Regulation as Index

By administering or contacting test compounds with a test animal or a test cell and confirming whether or not the test compounds regulate expression levels of LCE gene or a gene which is functionally equivalent to the gene, in the test animal or test cells, it is possible to identify test compounds which are effective for treatment or prevention of obesity.

Specifically, a test compound is evaluated by the following procedure.

First, the test compound is administered to or contacted with the test animal or a test cell. There are no restrictions on the type of the compound, regardless of its structure or properties, so long as it is a candidate compound for treatment or prevention of obesity. The mode of administering the test compound to the test animal is not particularly restricted, and specifically there may be mentioned, for example, oral administration and parenteral administration (such as percutaneous administration, intramuscular injection, intravenous injection or subcutaneous injection). There are also no particular restrictions on the method of containing the test compound with the test cell, and specifically there may be mentioned, for example, methods of contact by admixture in a solution such as a culture solution or buffer solution (phosphate buffer or the like).

It is then confirmed whether or not the test compound regulates the level of expression of LCE gene or a gene which is functionally equivalent to that gene in the test animals or the test cell.

There are no particular restrictions on the method of confirming whether or not the expression level of the gene is regulated, and it may be carried out by detecting change in the gene expression level by a gene amplification method such as RT-PCR, a method using a DNA microarray or a Northern hybridization method, against the pre-administration or pre-contact levels as a control. There may optionally be used animals or cells having artificially introduced therein a fused gene comprising the aforementioned gene with an expression regulatory region and a reporter gene. For such cases, specific examples of reporter genes include β-galactosidase gene, luciferase gene and green fluorescence protein gene.

Here, "a gene which is functionally equivalent to LCE gene" refers to a gene which has a different nucleotide sequence than LCE gene but exhibits relatively high homology and has identical or similar activity to LCE. The degree of homology is not particularly restricted so long as the functions of the genes are equivalent, but the nucleotide sequence homology is preferably 70-100%, more preferably 80-100% even more preferably 90-100% and most preferably 95-100%. If the homology is lower than this range, the gene is probably one which does not exhibit identical or similar function to LCE. However, even if the nucleotide sequence homology is below the aforementioned range, the gene may still have identical or similar function to LCE gene if there is high homology between the domain exhibiting the unique function of LCE and the nucleotide sequence corresponding to that domain. Such genes can be suitably used even if the nucleotide sequence homology falls outside of the aforementioned range. In addition, a gene with relatively high homology can be obtained by natural or artificial substitution, deletion, addition and/or insertion of one or more bases of LCE gene.

When the expression level of LCE gene or a gene which is functionally equivalent to LCE gene is reduced by at least 20% and preferably at least 50% after administration of or contact with the test compound compared to the level before administration of or contact with the test compound, the test compound may be evaluated as a compound effective for treatment or prevention of obesity.

(B) Evaluation Method Using LCE Protein Activity as Index

If a test compound is administered to or contacted with LCE protein and it is confirmed whether or not the test compound affects activity of the protein, it is also possible to evaluate test compounds which are effective for treatment or prevention of obesity.

Specifically, a test compound may be evaluated by the following procedure.

First, the test compound is contacted with LCE protein. There are no particular restrictions on the method of contacting the test compound with the protein, and specifically there may be mentioned, for example, methods of contact by admixture in a solution such as a buffer solution (phosphate buffer or the like).

It is then confirmed whether or not the test compound affects the activity of the protein. The conditions for assaying the protein activity may be appropriately set depending on the nature of the protein used. The specific conditions, in the case of LCE protein for example, may use elongase activity as the index, and more specifically, the method may involve admixture and incubation of a cell-extracted microsome fraction in a solution containing NADPH palmitoyl CoA and $^{14}$C-labeled malonyl CoA for extraction of the fatty acids, and then assay of the specific radioactivity in the fatty acids for measurement of the elongase activity. Alternatively, the method may be carried out with reference to J. Biol. Chem. 276(48), 45358-45366 (2001).

When the expression level of LCE gene or a gene which is functionally equivalent to LCE gene is reduced by at least 20% and preferably at least 50% after administration of or contact with the test compound compared to the level before administration of or contact with the test compound, the test compound may be evaluated as a compound effective for treatment or prevention of obesity.

The method of evaluating compounds effective for treatment or prevention of obesity according to the invention as explained above allows screening of therapeutic or diagnostic agents for obesity, evaluation of the efficacy and safety of such agents, and selection of appropriate agents for tailor-made therapy.

(C) Method of Evaluating Compounds which Inhibit LCE Protein

By contacting a test compound with a plurality of elongase proteins including LCE, assaying the activities of the plurality of elongase proteins and then selecting test compounds which inhibit LCE activity, it is possible to evaluate and select compounds that inhibit elongase activity, and specifically LCE elongase activity.

Specifically, the evaluation may be conducted by the following procedure.

First, a test compound is contacted with each of a plurality of elongase proteins including LCE. The method of contacting the proteins and the test compound is not particularly restricted, and specifically there may be mentioned, for example, methods of contact by admixture in a solution such as a buffer solution (phosphate buffer or the like). The types of elongases used are not restricted so long as they have elongase activity, and as specific examples there may be mentioned FAS (Fatty Acid Synthase) and ELO-1.

Next, it is confirmed whether or not the test compounds affect the protein activity. The conditions for assaying the protein activity may be appropriately set depending on the nature of the protein used. The specific conditions, in the case of LCE protein for example, may use elongase activity as the index, and more specifically, the method may be carried out with reference to J. Biol. Chem. 276(48), 45358-45366 (2001). For other elongases, elongase activity may be used as the index as for LCE, and the activity assay may be carried out according to a publicly known method such as, for example, a method based on J. Biol. Chem. 276(48), 45358-45366 (2001).

The method of evaluating compounds effective for treatment or prevention of obesity according to the invention as described above allows screening of the therapeutic or diagnostic agents for obesity, evaluation of the efficacy and safety of such agents, and selection of appropriate agents for tailor-made therapy.

(2) Fat Synthesis Inhibiting Method and Obesity Treatment and Prevention Method

A method of inhibiting fat synthesis and a method of treating or preventing obesity according to the invention will now be explained. Since LCE is a synthase of fatty acids which are constituents of fat, inhibition of its enzyme activity can block synthesis of fatty acids and thus prevent synthesis of fat.

Specifically, fat synthesis inhibition is accomplished by the following procedure.

First, a substance which inhibits LCE activity is selected. The substance may be, for example, a compound which functions as an LCE inhibitor, or an antibody against LCE, antisense nucleotide or siRNA (small interfering RNA; double-stranded RNA consisting of sense RNA and antisense RNA) used for RNAi.

Next, the substance is introduced into an individual, tissue or cell in which LCE is present. Specifically, when the target is an individual, the method of introduction is not particularly restricted and may be intraarterial injection, intravenous injection, subcutaneous injection, intranasal introduction, transbronchial inhalation, intramuscular administration or oral administration of the compound. When the target is a tissue, the method of introduction is not particularly restricted and may be injection into the tissue or introduction by admixture in a buffer solution. When the target is a cell, the method of introduction is not particularly restricted and may be admixture in a buffer solution, electroporation, or the like.

More specifically, RNAi can be accomplished by introduction of siRNA into cells by, for example, contacting liposome-packaged siRNA with cells added to a cell culture solution (Nature, 411, 494-498, (2001); J. Cell Sci., 114(Pt 24), 4557-4565, (2001); Biochem. Biophys. Res. Commun., 301 (3), 804-809, 2003). The following siRNA may be used for RNAi of LCE: hLCE-siRNA-1 (SEQ ID NOs: 13 and 14), hLCE-siRNA-2 (SEQ ID NOs: 15 and 16), hLCE-siRNA-3 (SEQ ID NOs: 17 and 18), hLCE-siRNA-4 (SEQ ID NOs: 19 and 20), hLCE-siRNA-5 (SEQ ID NOs: 21 and 22), hLCE-siRNA-6 (SEQ ID NOs: 23 and 24), LCE-siRNA-2 (SEQ ID NOs: 25 and 26), hLCE-siRNA-7 (SEQ ID NOs: 27 and 28), hLCE-siRNA-8 (SEQ ID NOs: 29 and 30), hLCE-siRNA-9 (SEQ ID NOs: 31 and 32), hLCE-siRNA-10 (SEQ ID NOs: 33 and 34), hLCE-siRNA-11 (SEQ ID NOs: 35 and 36), hLCE-siRNA-12 (SEQ ID NOs: 37 and 38), hLCE-siRNA-6 (SEQ ID NOs: 49 and 50), mLCE-siRNA-7 (SEQ ID NOs: 51 and 52) and mLCE-siRNA-11 (SEQ ID NOs: 53 and 54). These siRNA may also be used in different combinations to allow RNAi to occur. Among these siRNA, hLCE-siRNA-6 (SEQ ID NOs: 23 and 24) is most suitable for LCE RNAi because of its particularly powerful expression-suppressing effect on LCE.

Inhibiting LCE activity in this manner blocks the elongation reaction of fatty acid carbon chains and inhibits biosynthesis of fatty acids.

Such a method of inhibiting fat synthesis can be applied for treatment or prevention of obesity. That is, inhibiting LCE activity in the body can block synthesis of fatty acids, resulting in inhibited synthesis of lipids, thereby allowing treatment or prevention of obesity.

Specifically, treatment or prevention of obesity may be accomplished in the following manner.

First, a substance which inhibits LCE activity is selected. The substance may be, for example, a compound which functions as an LCE inhibitor, or an antibody against LCE, antisense nucleotide or siRNA used for RNAi.

Next, the substance is administered the body. The method of administration is not particularly restricted and may be, for example, intraarterial injection, intravenous injection, subcutaneous injection, intranasal administration, transbronchial inhalation, intramuscular administration or oral administration of the compound. A specific method using RNAi is as explained above for fat synthesis inhibition.

(3) A Method of Examining Obesity or Emaciation

A method of examining obesity or emaciation according to the invention will now be explained.

(A) A Method of Examining Obesity or Emaciation Based on Assay of LCE Gene Expression Levels By detecting change in the expression level of LCE gene or assaying its expression level in a test tissue or a test cell, it is possible to perform examination or diagnosis regarding obesity of the organism (for example, a human) from which the test tissue or the test cell have been extracted. This allows not only examination of the condition of obesity at the time of examination, but also permits prognosis regarding possible future obesity or emaciation.

A specific method for such examination will now be explained.

First, the test tissue or test cells are extracted from an organism as the subject of examination. There are no particular restrictions on the method of extraction, and any publicly known method may be employed.

Next, the gene whose expression level is to be assayed is prepared from extracted test tissue or test cell. Assay of LCE gene expression level requires preparation of LCE RNA (total RNA or mRNA) from the test tissue or the test cell. The RNA can be prepared by a publicly known method, with reference to, for example, Molecular cloning A LABORATORY MANUAL 2nd EDITION (1989) (T. Maniatis: Cold Spring Harbor Laboratory Press) 7.3-7.36. The prepared RNA may then be used for measurement of the expression level by, for example, a gene amplification method such as RT-PCR, a method using a DNA microarray (for example, an Affymetrix DNA chip) or a Northern hybridization method. The expression level may also be measured by in situ hybridization or the like, using the test tissue or the test cell.

For detection of changes in the expression level of LCE gene, the change in expression level may be determined by assaying the expression level before and after a period in which the expression level is expected to change (for example, before and after administration of an obesity therapeutic agent). Specifically, it is possible to determine that an increase in body weight has occurred or may occur in the future if expression level of LCE gene in a test tissue or a test cell is significantly increased before and after a period in which the expression level is expected to change.

(B) A Method of Examining Obesity or Emaciation Based on Assay of LCE Protein Expression Levels By detecting change in expression level of LCE protein in a test tissue or a test cell, or by assaying the expression level, it is possible to perform examination or diagnosis regarding obesity of the organism (for example, human) from which the test tissue or the test cell have been extracted. This allows not only examination of the condition of obesity at the time of examination, but also permits prognosis regarding possible future obesity or emaciation.

A specific method for examination will now be explained.

The method for protein expression level assay may be a method of quantitating protein isolated from an organism or a method of assaying protein levels in the blood, and there are no particular restrictions on the actual method employed. A specific method for quantitation of protein isolated from an organism is described below. First, LCE protein is prepared from a test tissue or a test cell. The protein preparation may be carried out by a publicly known method. The expression level can be measured from the prepared protein using a method employing a protein chip (for example, Protein Chip System by CIPHERGEN) or an immunological method (for example, ELISA, EIA or West blotting). The expression level can also be measured by immunostaining of the test tissue or the test cell. As a specific example of a method of measuring protein levels in the blood there may be mentioned quantitation of LCE protein by an immunological method as mentioned above, using sampled blood from the organism.

Thus, by analyzing the results after assaying LCE gene or protein expression levels in the manner described above, it is possible to examine the state of obesity of a subject. That is, according to the present invention, a fixed correlation between LCE protein expression level and body weight has been established, and therefore comparison of the examination results with the LCE protein expression level of a control group (healthy individuals) allows judgment of the severity of obesity. The examination method of the invention allows not only examination of the state of obesity at the time of examination, but also permits prognosis regarding possible future obesity or emaciation.

For detection of change in the level of expression of LCE protein, the change in expression level may be determined by measuring the expression level before and after a period in which the expression level is expected to change (for example, before and after administration of an obesity therapeutic agent). Specifically, it is possible to determine that an increase in body weight has occurred or may occur in the future if expression level of the LCE protein in a test tissue or a test cell is significantly increased before and after a period in which the expression level is expected to change.

(C) A Method of Examining Obesity or Emaciation Based on Detection of Gene Polymorphisms in LCE Gene When gene polymorphisms are present in LCE gene, expression levels of LCE gene or protein vary depending on the existence and types of such polymorphisms, and can often abnormally affect activity of the protein. Thus, detection of such gene polymorphisms can yield knowledge regarding LCE expression and activity, while also allowing examination regarding obesity of a subject from which a test tissue or a test cell is derived. Such polymorphisms include, specifically, minisatellites, microsatellites and SNPs (single nucleotide polymorphisms).

Detection of polymorphisms in LCE gene may be accomplished in the following manner. Specifically, the base sequence of a region which controls expression of LCE gene is determined for obesity test subjects to be examined, and polymorphic sites are located. The allelic frequencies at the detected polymorphic sites are calculated, and polymorphisms are identified which correlate with obesity by discovering alleles which are significantly increased or decreased in the subject group. The genetic polymorphisms determined in this manner may be clinically detected in genomic DNA derived from the subject by, for example, a method of analyzing the base sequence at the polymorphic site, or utilizing differences in the physicochemical properties of DNA which vary depending on the type of base at the polymorphic site, or differences in restriction endonuclease sites, a method utilizing a detection probe suitable for detection of the polymorphic site, or a method utilizing mass spectrometry.

(D) A Method of Examining Obesity Based on Detecting Expression or Activity of Protein which Affects Expression of LCE Gene Through Interaction with LCE Protein Most proteins exhibit their physiological function in vivo by interaction with other proteins. LCE also exhibits its function with its expression under control by the action of transcription factors, for example. A fixed correlation exists between LCE protein and the expression or activity of a protein which affects expression of LCE gene by interaction with LCE protein, and the relationship is such that detection of the behavior of either allows measurement of the behavior of the other.

Here, "interaction" refers to direct or indirect action between LCE protein and a different protein, and for example, there may be mentioned action whereby physical contact between LCE protein and the different protein results in modification of an amino acid, or interaction via a third protein which indirectly affects expression of LCE protein. Such proteins include, for example, proteins that exhibit their physiological function upstream or downstream from LCE protein for signal transduction via LCE protein. The method of detecting expression or activity of such a protein may be appropriately selected as a suitable means depending on the protein of interest, and there are no particular restrictions on the specific method.

The method of examining obesity according to the invention as explained under (A) to (D) above not only allows diagnosis of obesity on the molecular level but also permits prognosis reading possible future obesity and more precise diagnosis compared to conventional diagnostic methods.

(4) Therapeutic or Preventing Agents for Obesity

A correlation is seen between LCE gene expression levels and body weight. Thus, a compound that regulates the expression level of the gene to the normal level is not only useful for treatment or prevention of obesity, but can also be applied to conditions such as, for example, emaciation, diabetes, hypertension, hyperlipidemia and ischemic heart disease. Such compounds include those selected by the method of evaluating compounds according to the invention. Such compounds may be used as drugs by direct administration of the compounds to patients, or by their administration in the form of medical compositions form by publicly known pharmaceutical methods. For formulation, the following may be specifically mentioned as examples of pharmacologically acceptable carriers or media: sterilized water, physiological saline, vegetable oils, emulsifiers, suspending agents, surfactants, stabilizers, binders, lubricants, sweeteners, aromatics and coloring agents. As examples of methods of administering such medical compositions to patients there may be mentioned intraarterial administration, intravenous injection, subcutaneous injection, intranasal administration, transbronchial inhalation, intramuscular administration or oral administration. The amount of the medical composition administered will vary depending on the patient body weight and age and the method of administration, and a suitable dosage may be selected by a person skilled in the art.

(5) Obesity Examination Agent and Examination Kit

LCE protein expression levels are correlated with changes in body weight due to obesity. Thus, antibodies against the protein can be used for detection and assay of the protein levels in a test cell or a test tissue to conveniently perform examination of obesity. Here, "antibodies" may be full antibody molecules or fragments thereof, which are able to bind LCE gene product as antigen. Such antibodies may be produced by publicly known methods, and may be either monoclonal antibodies or polyclonal antibodies. Immunological assay using such antibodies may be accomplished by a publicly known method, and specifically there may be mentioned fluorescent antibody assay and enzyme-antibody assay.

The present invention can also be implemented by producing a kit including such antibodies. The kit construction may include, in addition to the antibodies, a fluorescent labeling substance for detection of the antibodies, as well as a secondary antibody labeled with a radioisotope and a buffer solution to be used for antigen-antibody reaction.

By using such an examining agent for obesity, it is possible not only to diagnose obesity on the molecular level, but also to perform prognosis regarding possible future obesity, and to achieve a more accurate diagnosis than conventional diagnostic methods. Moreover, using an examination kit for obesity according to the invention allows such accurate diagnosis to be carried out in a highly convenient manner.

(6) hLCE-siRNA-6 (siRNA Comprising Nucleic Acid of SEQ ID NOs: 23 and 24), and LCE Expression Suppressors, Fat Synthesis Inhibitors and Obesity Therapeutic and Preventing Agents Containing the Same hLCE-siRNA-6, siRNA consisting of nucleic acid of SEQ ID NOs: 23 and 24, strongly suppresses LCE expression. Thus, hLCE-siRNA-6 can be used as an LCE expression suppressor, as a fat synthesis inhibitor, or as a therapeutic or preventing agent for obesity.

EXAMPLES (Creation of Obesity Model Animal)

Preparation Example 1

Mice Intracerebroventricularly (i.c.v) Administered with Neuropeptide Y (NPY) Y5 Agonist A mouse model of obesity induced by administration of an NPY Y5 agonist was prepared in the following manner. Nine- to twelve-week-old male mice (C57BL/6J: Clea Japan) were raised under conditions with a room temperature of 23±2° C. and a humidity of 55±15%, with one mouse in each plastic cage. The mice were raised under a 12 hour lightness/darkness cycle, with lights on at 7:00 am and lights off at 7:00 pm. The mice were also given free access to feed (CE-2 (25.4 wt % protein, 50.3 wt % carbohydrate, and 4.4 wt % lipid), Clea Japan) and water.

The mice were anesthetized with 80 mg/kg sodium pentobarbital (Dynabot) and a 28-gauge sterilized brain fusion cannula (Alzet Co.) was stereotactically implanted in the right cerebral ventricle. The cannula was positioned 0.4 mm behind and 0.8 mm to the side of the bregma, and to a depth of 2 mm, and was anchored vertically with respect to the cranial bone using dental cement. A polyvinyl chloride tube was used to connect the cannula to an osmotic pump Model #2002: Alzet Co.) filled with 10 mM phosphate buffer containing 0.05% bovine serum albumin (BSA). A solution of D-Try$^{34}$ NPY in 10 mM PBS (containing 0.05% BSA) (prepared for 5 μg/day) was filled into the pump, and the pump was implanted subcutaneously at the back of the mouse, and the mouse was subcutaneously injected with an antibiotic (50 mg/kg Cefamedine; Fujisawa Pharmaceutical Co., Ltd.).

The mice were divided into three groups with equivalent average body weights: a group injected with the solvent (vehicle group); a group injected with D-Try$^{34}$ NPY (NYP Y5 agonist) (ad lib fed group); and a group injected with D-Try$^{34}$ NPY and pair-fed (pair-fed group).

Preparation Example 2

MCH-administered Mice

A mouse model of obesity induced by administration of MCH (melanin-concentrating hormone) was prepared in the following manner.

Thirteen-week-old male mice (C57BL/6J: Clea Japan) were raised under conditions with a room temperature of 23±2° C. and a humidity of 55±15%, with one mouse in each plastic cage. The mice were raised under a 12 hour lightness/darkness cycle, with lights on at 7:00 am and lights off at 7:00 pm. The mice were also given free access to feed (CE-2 (25.4 wt % protein, 50.3 wt % carbohydrate, and 4.4 wt % lipid), Clea Japan) and water. When the mice had adapted to their environment, they were given MHF (15.0 wt % protein, 52.4 wt % carbohydrate, 32.6 wt % lipid, Oriental Bioservice) as feed.

The mice were anesthetized with 80 mg/kg sodium pentobarbital (Dynabot) and a 28-gauge sterilized brain fusion cannula (Ale Co.) was stereotactically implanted in the right cerebral ventricle. The cannula was positioned 0.4 mm behind and 0.8 mm to the side of the bregma, and to a depth of 2 mm, and was anchored vertically with respect to the cranical bone using dental cement. A polyvinyl chloride tube was used to connect the cannula to an osmotic pump Model #2002: Alzet Co.) filled with 30% propylene glycol. The pump was implanted subcutaneously at the back of the mouse, and the mouse was subcutaneously injected with an antibiotic.

The mice were divided into three groups with equivalent average body weights: a group injected with the solvent (vehicle group); a group injected with MCH (ad lib fed group); and a group injected with MCH and pair-fed (pair-fed group). The pump was then replaced with MCH (3 μg/day) or solvent (30% propylene glycol) under ether anesthesia.

Preparation Example 3

DIO (Diet Induced Obesity) Mice

Eighteen-week-old male mice (C57BL/6J: Clea Japan) were raised under conditions with a room temperature of 23±2° C. and a humidity of 55±15%, with one mouse in each plastic cage. The mice were given a high-calorie diet of MHF (18.2 wt % protein, 55.6 wt % carbohydrate, 15.5 wt % lipid) for a period of 6 months, to create an obese mouse model (DIO mice). In the examples, "established MFD" refers to mice raised with MHF feeding until body weight no longer increased.

Also created were DIO mice (HFD), which were the same mice given a high-calorie diet of HFD (20.8 wt % protein 38.59 wt % carbohydrate, and 32.88 wt % lipid) containing more fat than MHF.

Preparation Example 4

Dietary-restricted Mice

Mice (C57BL/6N, 17-week-old) were raised each separately in different cages. The feed given was ordinary feed (CA-1, Clea Japan). Dietary restriction was carried out according to the following schedule. Specifically, the feed (CA-1) was supplied for 3 hours each day (10:00-13:00), while water was made freely available. The feed weight was assured before and after the feeding time, and the difference was calculated as the ingested weight. The body weights and appearances were observed during the period of dietary restriction. Mice believed to have failed the conditions (mice which exhibited an excessive body weight decrease (for example, about a 20% decrease) in a short time) were not used for the experiment. After 7 days of raising the mice under these conditions, the white adipocytes were extend.

Examples 1-5 and Comparative Example 1

LCE Expression in White Adipocytes

The mouse models prepared in Preparation Examples 1-4 were used for measurement of LCE expression in liver and white adipocytes (WAT). The expression levels were measured by treating RNA extracted from white adipocytes from each mouse model using a mouse U74A chip (Affymetrix).

Table 1 shows LCE gene expression levels for DIO mice (DIO), D-Try$^{34}$ NPY-administered mice (NPY(FF)), D-Try$^{34}$ NPY pair feeding mice (NPY(PF)), MCH-administered mice (MCH(FF)), MCH pair feeding mice (MCH(PF)), dietary-restricted mice (fasting) and NPY Y5 agonist-administered mice (Y5ant), where the LCE expression in the liver or WAT of non-treated C57BL/6N mice was defined as 1.00.

As shown in Table 1, the LCE gene expression tended to increase in the obese mouse models, while the expression decreased in the dietary-restricted mice. Thus, a clear correlation was established between LCE expression level and body weight.

TABLE 1

|  | Obesity model | LCE expression in liver | LCE expression in WAT |
|---|---|---|---|
|  | Non-treated | 1.00 | 1.00 |
| Example 1 | DIO mice | 4.56 | 1.00 |
| Example 2 | NPY(PF) | 2.11 | 2.47 |
| Example 3 | NPY(FF) | 2.93 | 6.78 |
| Example 4 | MCH(PF) | 1.00 | 5.57 |
| Example 5 | MCH(FF) | 1.50 | 2.56 |
| Comp. Example 1 | Fasting | 0.14 | 0.19 |

Example 6

Measurement of Mouse LCE mRNA Expression Levels in HEK293 Cells

1. Preparation of LCE Expression-accelerated Cells

RNA extracted from mouse liver was used for amplification of mouse LCE cDNA by RT-PCR. After subcloning of the obtained PCR product into an expression vector pCDNA3.1, the base sequence was confirmed. The expression vector into which mouse LCE was subcloned was linearized with a restriction endonuclease ScaI and transfected into HEK293 cells. The cells were cultured in selective medium containing 1 mg/ml G418 to give a cell line with stable high expression of the mouse LCE gene.

The base sequences of the primers used for RT-PCR are shown below.

mLCE-exF: 5'-GCC ACC ATG GGC AAC ATG TCA GTG TTG ACT TTA C-3' (SEQ ID NO: 3)

mLCE-exR: 5'-CTA CTC AGC CTT CGT GGC TTT CTT-3' (SEQ ID NO: 4)

2. Assay of Mouse LCE mRNA Expression Levels in HEK293 Cells

The total RNA was purified from the HEK293 cells and used for reverse transcription reaction to obtain cDNA. Mouse LCE mRNA and human LCE mRNA expression was assayed by TaqMan PCR with an ABI Prism 7700 Sequence Detector System. A standard curve for mouse LCE was drawn from expression analysis using the aforementioned DNA obtained by linearizing the mouse LCE-subcloned expression vector with a restriction endonuclease ScaI. A standard curve for human LCE was drawn from subcloning of a PCR-prepared human LCE DNA fragment in pcDNA3.1 and expression analysis using the DNA fragment linearized with ScaI. The mouse LCE expression was then divided by the human LCE expression to determine the ratio of the mouse LCE gene expression and the intrinsic human LCE gene expression.

The base sequences of the primers and probes used are shown below.

```
TaqMan probe for mouse LCE
mLCE-P:
5'-CTT TCC TGT TTT CTG CGC TGT ACG    (SEQ ID NO: 5)
CTG-3'

TaqMan primer for mouse LCE
mLCE-F:
5'-GGA TGC AGG AAA ACT GGA AGA        (SEQ ID NO: 6)
A-3' mLCE-R:
5'-TGC CGA CCA CCA AAG ATA AAG-3'     (SEQ ID NO: 7)

TaqMan probe for human LCE
hLCE-P2:
5'-ATC ACT GTG CTC CTG TAC T-3'       (SEQ ID NO: 8)

TaqMan primer for human LCE
hLCE-F2:
5'-AGC TGA TCT TCC TGC ACT GGT        (SEQ ID NO: 9)
AT-3' hLCE-R2:
5'-GGC AAC CAT GTC TTT GTA GGA        (SEQ ID NO: 10)
GTA-3'

PCR primer for human LCE
mLCE-exF:
5'-GCC ACC ATG GGC AAC ATG TCA GTG    (SEQ ID NO: 11)
TTG ACT TTA C-3' hLCE-exR:
5'-CTA TTC AGC TTT CGT TGT TTT CCT    (SEQ ID NO: 12)
C-3'.
```

3. Assay of LCE Activity in HEK293 Cells

After disruption of the HEK293 cells by sonication, the microsome fraction was prepared by an ultracentrifuge prone. The obtained microsome fraction was used for assay of the LCE activity by the following method. The microsome fraction was added to phosphate buffer solution containing NADPH, palmitoyl CoA and $^{14}$C-labeled malonyl CoA, which are necessary for the reaction, and incubation was performed at 37° C. for 5 minutes. A solution of 15% potassium hydroxide-methanol was then added and the mixture was heated at 75° C. for 45 minutes for saponification. After adding 5N hydrochloric acid thereto, hexane was used for fatty acid extraction. The specific radioactivity of the obtained fatty acids was measured and the amount of malonyl CoA incorporated into the fatty acids by fatty acid elongation reaction was determined.

FIG. 1 is a graph showing (a) LCE mRNA expression and (b) LCE activity in cells forced to express LCE. As shown in FIG. 1, it was confirmed that cell lines with enhanced LCE expression had been obtained, and that LCE activity was enhanced in these cell lines.

Example 7

Measurement of Fatty Acid Composition in HEK293 Cells

The HEK293 cells were disrupted by sonication in phosphate buffer, and after adding C17:0 triglycerides, cholesteryl esters and phospholipids as internal standard substances, the lipid components were extracted with chloroform-methanol (2:1). The obtained lipids were dried to hardness under a nitrogen stream, and then fractionated by thin-layer chromatography using silica gel G (hexane:diethyl ether:acetic acid=80:20:1) for separation of the triglycerides, cholesteryl esters and phospholipids. The fatty acid residues of the three fractions were methylated with 5% hydrochloric acid-methanol, and the fatty acid composition was analyzed using gas chromatography (GC-FID).

Figure 2:
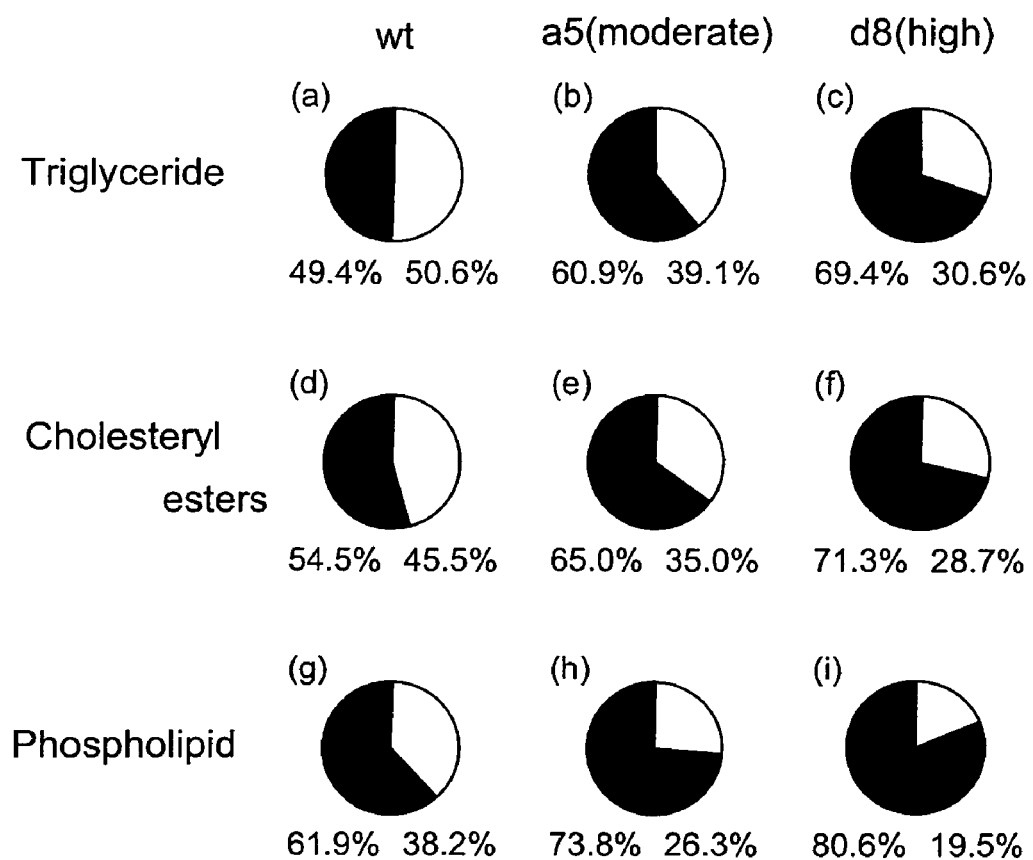
FIG. 2 is a set of pie graphs showing fatty acid compositions in cells forced to express LCE. The black portions represent fatty acids with carbon chains of C18 or more carbons, and the white portions represent fatty acids with carbon chains of C16 or fewer carbons. Graphs (a) to (c) sent the fatty acid compositions of triglycerides, graphs (d) to (f) present the fatty acid compositions of cholesteryl esters and graphs (g) to (i) represent the fatty acid compositions of phospholipids. "wt" represents non-treated HEK293 cells.

FIG. 2 shows the results of comparing fatty acids of C18 or more and C16 or less carbon chains. As is clear from FIG. 2, the component ratio of C18 or more fatty acids tended to increase in the cell lines with enhanced LCE expression, confirming that carbon chain elongation reaction proceeds in proportion to augmented LCE activity. Almost all of the fatty acids in the cells were present in ester form, i.e. triglycerides, cholesteryl esters and phospholipids. Since the component ratio of C18 or more fatty acids tended to increase with enhanced LCE expression for all of these esters, the change in LCE activity is presumably responsible for the altered fatty acid component ratios in all of the cells, leading the present inventors to conclude that LCE is an important factor determining the fatty acid composition of cells.

Figure 3:
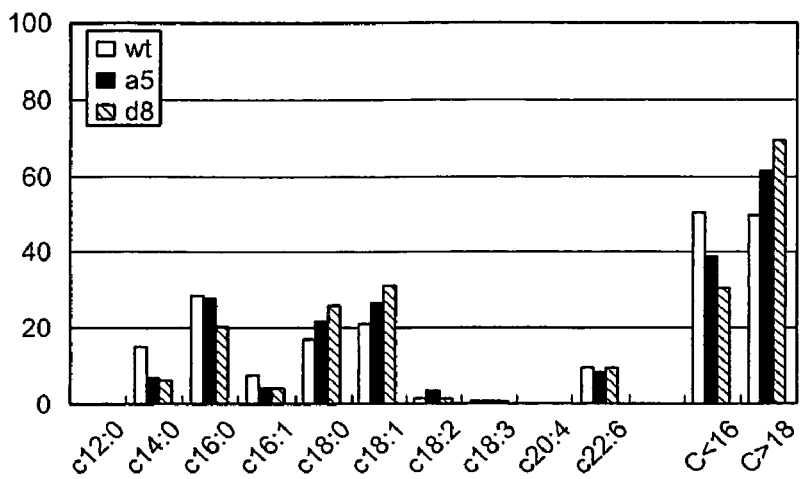
FIG. 3 is a set of bar graphs showing more detailed fatty acid compositions in cells forced to express LCE. Graph (a) rents the fatty acid compositions of triglycerides, graph (b) represents the fatty acid compositions of cholesteryl esters and graph (c) represents the fatty acid compositions of phospholipids.
Figure 3:
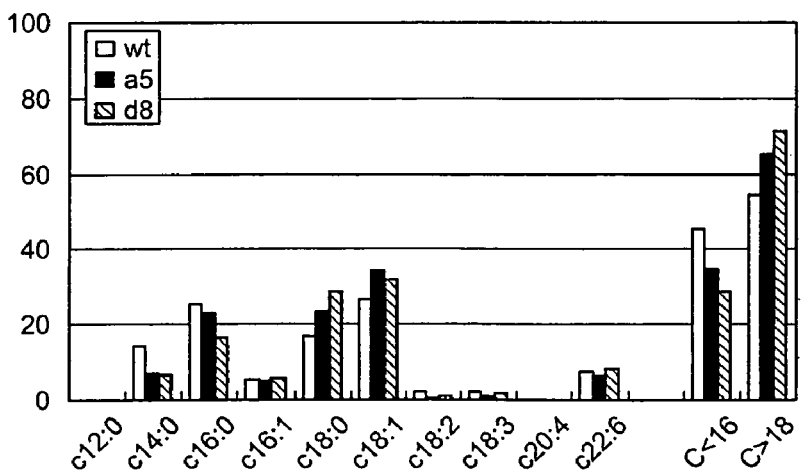
Figure 3:
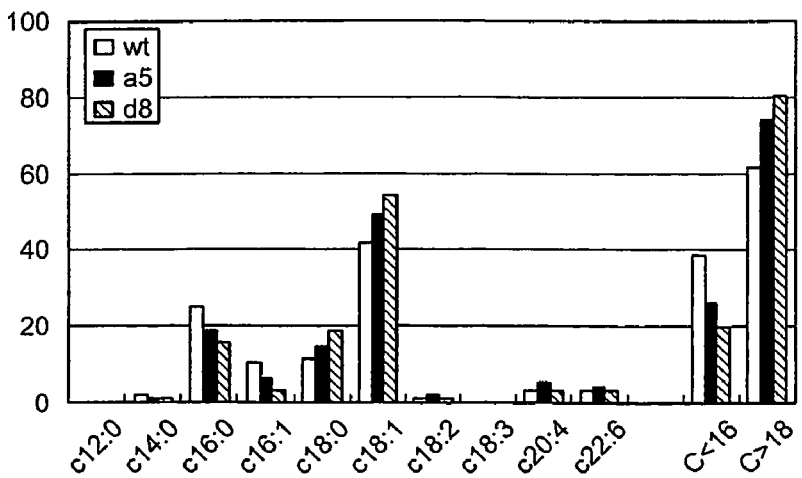

The results of comparison of the fatty acid compositions are shown in FIG. 3. As FIG. 3 clearly demonstrates, it was confirmed that the cell lines with enhanced LCE expression tended to have an increased component ratio of C18 or more fatty acids.

Example 8

Suppression of Human LCE Expression by RNAi

1. Examination of siRNA Used for Expression Suppression Experiment

Figure 4:
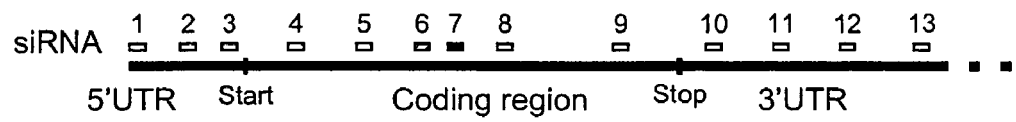
FIG. 4 shows the results of the suppression of the expression of LCE by RNAi. Drawing (a) shows the corresponding regions for each siRNA on LCE gene, and (b) shows expression of LCE mRNA upon transfection of each siRNA.
Figure 4:
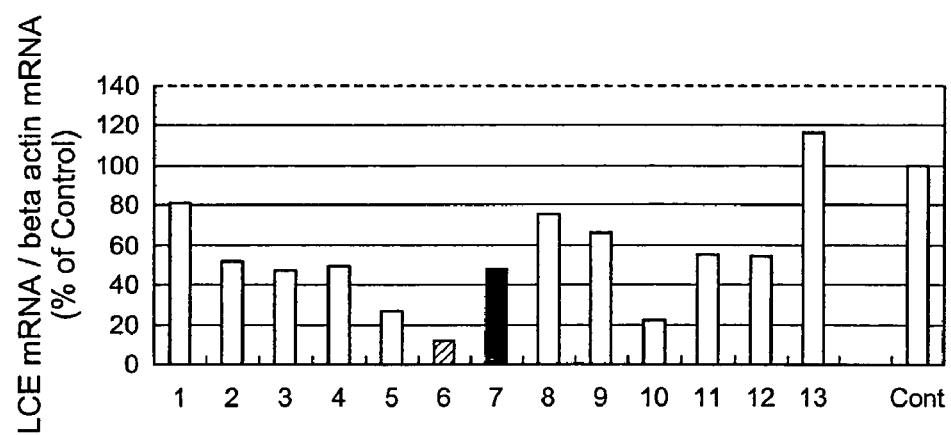

Based on nucleotide sequence data for human LCE DNA, siRNA (small interfering RNA) having the sequences listed below were synthesized. Each synthesized siRNA was transfected into HepG2 cells and after 24 hours the total RNA was prepared from the cells. Next, cDNA was yielded by reverse transcription reaction and human LCE mRNA expression was assayed by TaqMan PCR with an ABI Prism 7700 Sequence Detector System. FIG. 4(a) shows the corresponding regions for each siRNA on LCE gene, and FIG. 4(b) is a graph showing expression of LCE mRNA upon transfection of each siRNA. As seen in FIG. 4(b), it was confirmed that using the siRNA (hLCE-siRNA-6) produced a strong effect of the suppression of LCE expression.

The sequences of the siRNA used were as follows.

```
hLCE-siRNA-1
(siRNA 1 in FIG. 4)
5'-GACCGCAAGGCAUUCAUUUUU-3'        (SEQ ID NO: 13)

3'-UUCUGGCGUUCCGUAAGUAAA-5'        (SEQ ID NO: 14)

hLCE-siRNA-2
(siRNA 2 in FIG. 4)
5'-CACUCGAAAUCAAGCGCUUUU-3'        (SEQ ID NO: 15)

3'-UUGUGAGCUUUAGUUCGCGAA-5'        (SEQ ID NO: 16)

hLCE-siRNA-3
(siRNA 3 in FIG. 4)
5'-CACGUAGCGACUCCGAAGAUU-3'        (SEQ ID NO: 17)

3'-UUGUGCAUCGCUGAGGCUUCU-5'        (SEQ ID NO: 18)

hLCE-siRNA-4
(siRNA4 in FIG. 4)
5'-UGAAGCCAUCCAAUGGAUGUU-3'        (SEQ ID NO: 19)

3'-UUACUUCGGUAGGUUACCUAC-5'        (SEQ ID NO: 20)

hLCE-siRNA-5
(siRNA 5 in FIG. 4)
5'-GCCAUUAGUGCUCUGGUCUUU-3'        (SEQ ID NO: 21)

3'-UUCGGUAAUCACGAGACCAGA-5'        (SEQ ID NO: 22)

hLCE-siRNA-6
(siRNA 6 in FIG. 4)
5'-AGGCCUGAAGCAGUCAGUUUU-3'        (SEQ ID NO: 23)

3'-UUUCCGGACUUCGUCAGUCAA-5'        (SEQ ID NO: 24)

LCE-siRNA-2
(FIG. 4: siRNA 7)
5'-UGGACCUGUCAGCAAAUUCUU-3'        (SEQ ID NO: 25)

-continued
3'-UUACCUGGACAGUCGUUUAAG-5'        (SEQ ID NO: 26)

hLCE-siRNA-7
(siRNA 8 in FIG. 4)
5'-AGCACCCGAACUAGGAGAUUU-3'        (SEQ ID NO: 27)

3'-UUUCGUGGGCUUGAUCCUCUA-5'        (SEQ ID NO: 28)

hLCE-siRNA-8
(siRNA 9 in FIG. 4)
5'-CAUCUUCUGGUCCUCACUCUU-3'        (SEQ ID NO: 29)

3'-UUGUAGAAGACCAGGAGUGAG-5'        (SEQ ID NO: 30)

hLCE-siRNA-9
(siRNA 10 in FIG. 4)
5'-UCACACGUGGUGCAGCUAAUU-3'        (SEQ ID NO: 31)

3'-UUAGUGUGCACCACGUCGAUU-5'        (SEQ ID NO: 32)

hLCE-siRNA-10
(siRNA 11 in FIG. 4)
5'-GCACUGCUGCUGGAAGACCUU-3'        (SEQ ID NO: 33)

3'-UUCGUGACGACGACCUUCUGG-5'        (SEQ ID NO: 34)

hLCE-siRNA-11
(siRNA 12 in FIG. 4)
5'-ACUGUGCGAGCACAACACAUU-3'        (SEQ ID NO: 35)

3'-UUUGACACGCUCGUGUUGUGU-5'        (SEQ ID NO: 36)

hLCE-siRNA-12
(siRNA 13 in FIG. 4)
5'-AGGGGGUGAAUACUUCCCCUU-3'        (SEQ ID NO: 37)

3'-UUUCCCCCACUUAUGAAGGGG-5'        (SEQ ID NO: 38).
```

2. LCE Activity-reducing Effect of siRNA in HepG2 Cells

Figure 5:
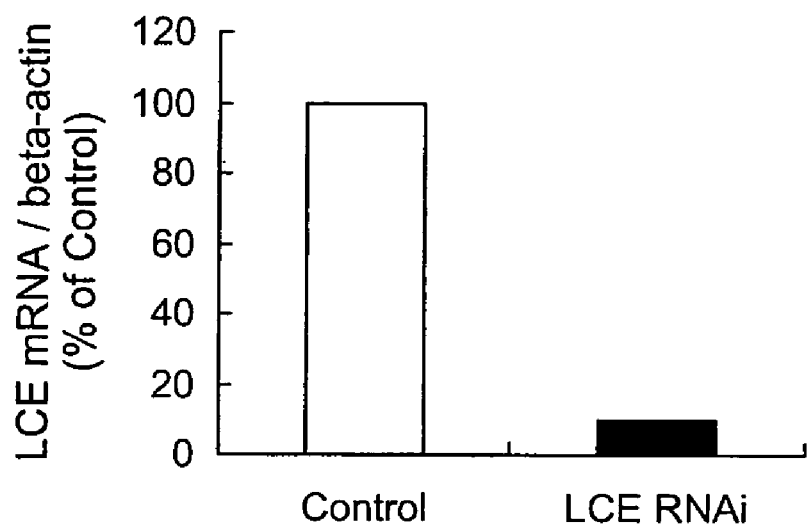
FIG. 5 is a pair of graphs showing the results of activity inhibition of LCE by RNAi. Graph (b) shows LCE mRNA expression, and graph (b) shows Fatty Acyl CoA elongation activity. LCE RNAi represents RNAi of LCE using hLCE-siRNA-6 (likewise hereunder, unless otherwise specified).
Figure 5:
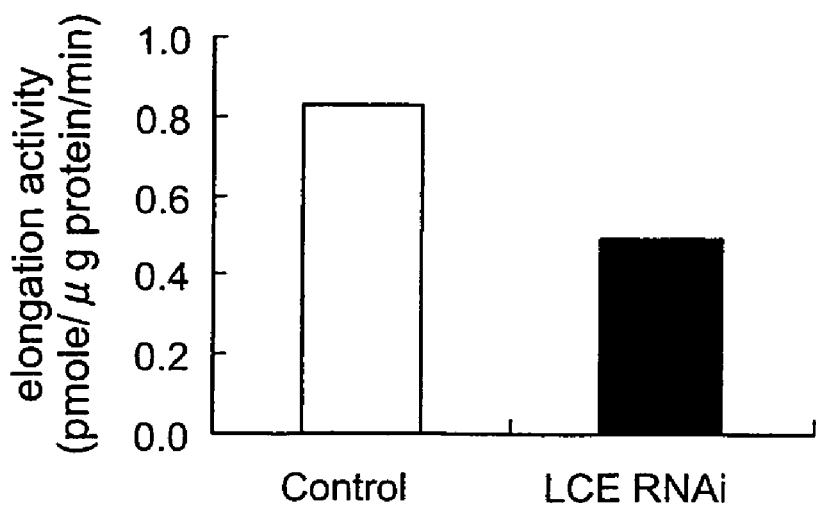

After disruption of siRNA (hLCE-siRNA-6)-transfected HepG2 cells by sonication, the microsome fraction was prepared by an ultracentrifuge procedure. The LCE activity (Fatty Acyl CoA elongation activity) of the obtained microsome fraction was then assayed. As a control there were used HepG2 cells into which siRNA having a sequence with no mammalian gene homology (scramble siRNA Duplex: Dharmacon, Inc.) had been transfected. FIG. 5(a) is a graph showing LCE mRNA expression, and FIG. 5(b) is a graph showing elongation activity. As seen in FIGS. 5(a) and (b), it was confirmed that LCE expression had been specifically inhibited and that LCE activity had also been inhibited.

Figure 6:
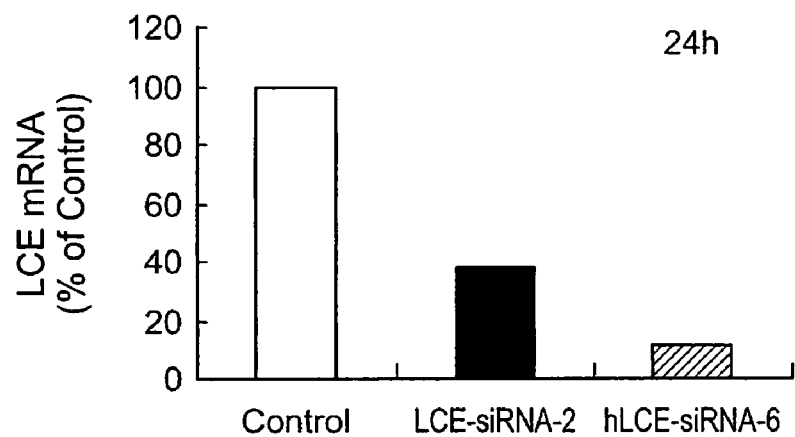
FIG. 6 is a pair of graphs showing LCE mRNA expression in siRNA-transfected HepG2 cells. (a): at 24 hours, (b): at 48 hours.
Figure 6:
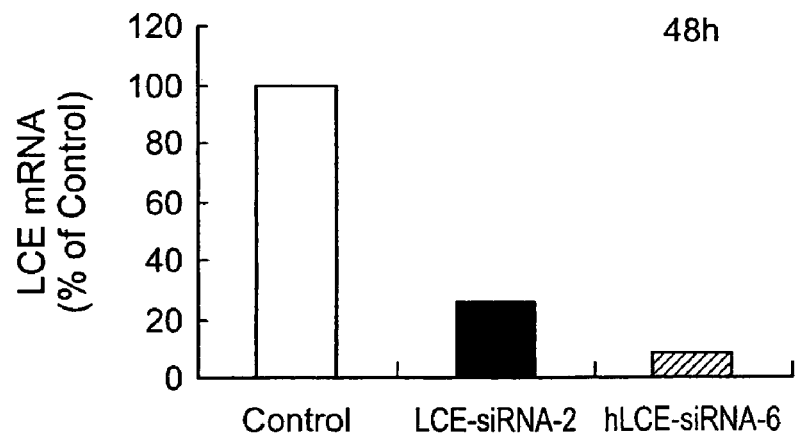

Two different siRNA (one with a strong expression-suppressing effect (hLCE-siRNA-6) and one with a moderate expression-suppressing effect (LCE-siRNA-2)) were transfected into HepG2 cells. At 24 and 48 hours after the siRNA transfection, the total RNA was prepared from the cells, gene expression was analyzed using a DNA chip (Affymetrix), and genes were selected whose expression was reduced by siRNA transfection. FIG. 6 is a pair of graphs showing LCE mRNA expression after siRNA transfection ((a): 24 hour, (b): 48 hours). It was confirmed that siRNA transfection suppressed LCE expression.

The number of genes whose expression was reduced by siRNA transfection was 5 at 24 hours and 64 at 48 hours. Of the genes with reduced expression, the expression levels of FAS (Fatty Acid Synthase) and SCD (Stearyl CoA Desaturase), which like LCE are involved in fatty acid synthesis, were the focus of study. Specifically, total RNA was purified from siRNA (hLCE-siRNA-6)-transfected HepG2 cells, and cDNA was obtained by reverse transcription reaction. Next human FAS mRNA and human SCD mRNA expression levels were Ned by TaqMan PCR with an ABI Prism 7700

Figure 7:
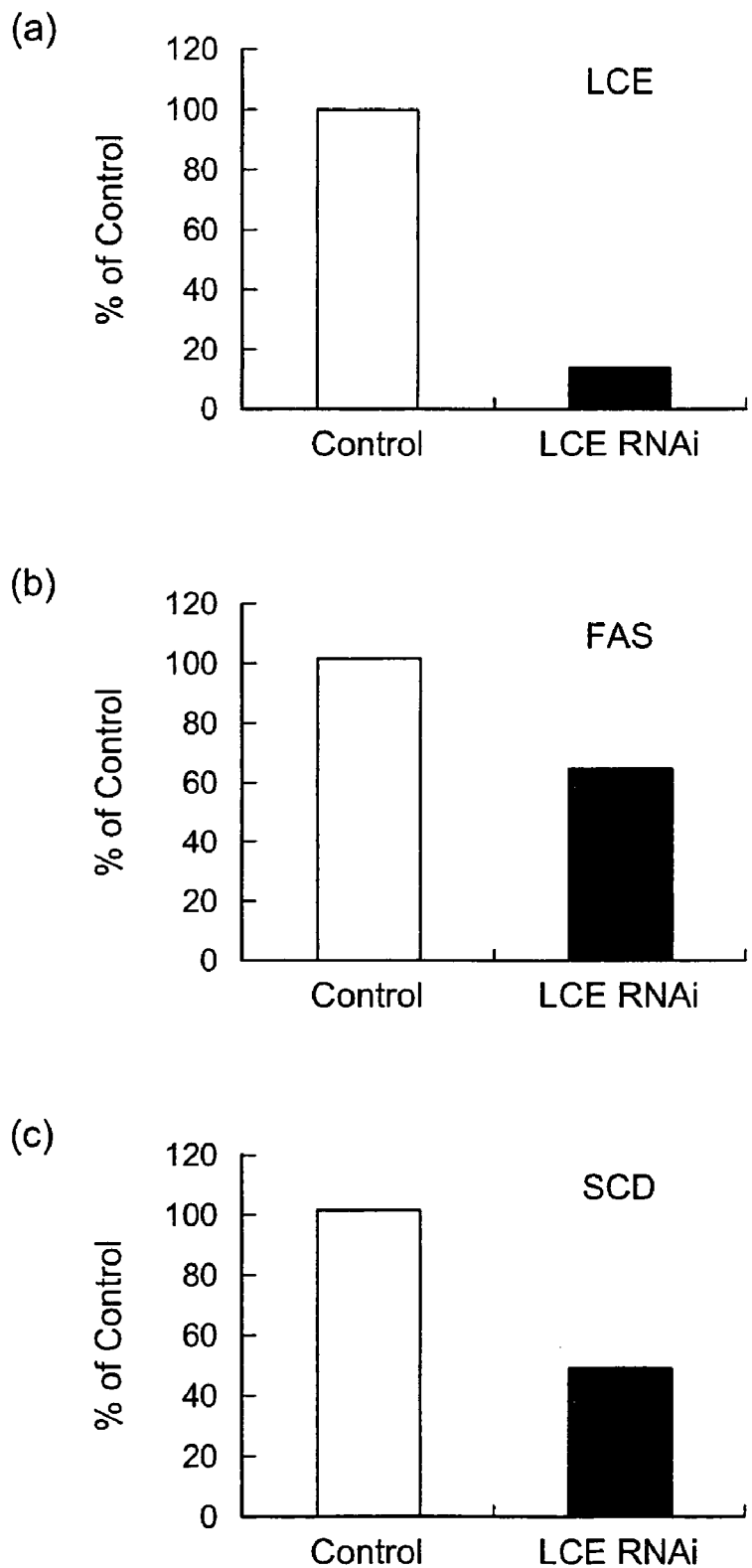
FIG. 7 is a set of graphs showing (a) LCE, (b) FAS and (c) SCD mRNA expression in siRNA-transfected HepG2 cells.

Sequence Detector System. A standard curve was drawn using the human FAS cDNA fragment and human SCD cDNA fragment prepared by PCR. The expression levels of FAS and SCD were normalized based on β-actin expression levels. FIG. 7 is a set of graphs showing (a) LCE, (b) FAS and (c) SCD mRNA expression levels in the siRNA-transfected HepG2 cells. As shown in FIG. 7, siRNA transfection significantly reduced LCE expression, while expression levels of FAS and SCD, though not being reduced to the extent of LCE expression, were still reduced by about 40-60%.

The base sequences of the primers and probes used for measurement were as follows.

```
TaqMan probe for human FAS
hFAS-P:
5'-ACC CGC TCG GCA TGG CTA TCT    (SEQ ID NO: 39)
T-3'

TaqMan primer for human FAS
hFAS-F:
5'-GCA AAT TCG ACC TTT CTC AGA    (SEQ ID NO: 40)
AC-3' hFAS-R:
5'-GGA CCC CGT GGA ATG TCA-3'     (SEQ ID NO: 41)

PCR primer for construction of human FAS cDNA
hFAS-4823S:
5'-TAC GCC TCC CTC AAC TTC CG-3'  (SEQ ID NO: 42)

hFAS-5604A:
5'-CAC TTG AGG GGC CGT ACC AC-3'  (SEQ ID NO: 43)

TaqMan probe for human SCD
hSCD-P:
5'-CAC ATG CTG ATC CTC ATA ATT CCC (SEQ ID NO: 44)
GAC G-3'

TaqMan primer for human SCD
hSCD-F:
5'-GCC CAC CAC AAG TTT TCA GAA-3' (SEQ ID NO: 45)

hSCD-R:
5'-CCA CGT GAG AGA AGA AAA AGC    (SEQ ID NO: 46)
C-3'

PCR primer for construction of human SCD cDNA
hSCD-600S:
5'-TGT GGA GCC ACC GCT CTT AC-3'  (SEQ ID NO: 47)

hSCD-931A:
5'-AAG CGT GGG CAG GAT GAA GC-3'. (SEQ ID NO: 48).
```

Example 9

Suppression of Mouse LCE Expression by RNAi

The same experiment as in Example 8 was carried out using mouse LCE. Based on nucleotide sequence data for mouse LCE DNA, siRNA having the sequences listed below were synthesis. Each synthesized siRNA was transfected into 3T3-L1 cells and after 24 hours the total RNA was prepared from the cells. Next, cDNA was yielded by reverse transaction reaction and mouse LCE mRNA expression was increased by TaqMan PCR with an ABI Prism 7700 Sequence Detector System.

Figure 8:
FIG. 8 shows the results of the suppression of the expression of mouse LCE by RNAi. Drawing (a) shows corresponding regions for each siRNA on mouse LCE gene, (b) shows expression of mouse LCE mRNA upon transfection of each siRNA, and (c) shows expression of mouse FAS mRNA upon transfection of each siRNA.
Figure 8:
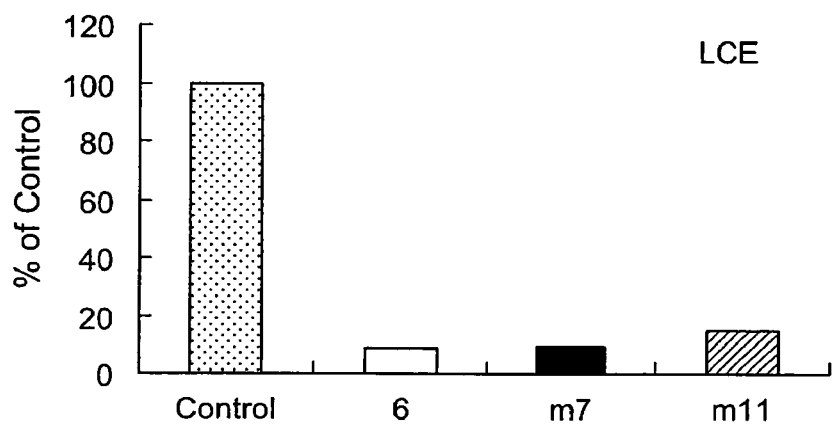
Figure 8:
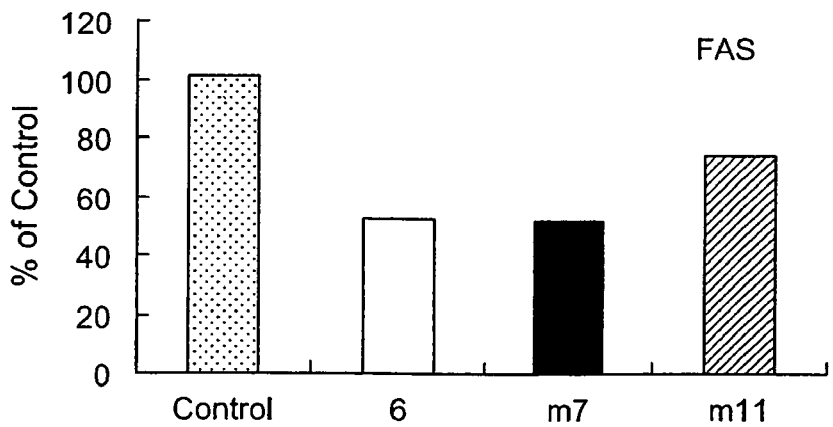

FIG. 8 is a set of graphs showing the results of the suppression of the mouse LCE expression by RNAi. Drawing (a) shows corresponding regions for each siRNA on mouse LCE gene, (b) shows expression levels of mouse LCE mRNA upon transfection of each siRNA, and (c) shows expression levels of mouse FAS mRNA upon transfection of each siRNA. As shown in FIG. 8, each siRNA was confirmed to suppress expression of LCE and FAS.

The siRNA used for the experiment are listed below.

hLCE-siRNA-6 (identical to hLCE-siRNA-6 used as siRNA for human LCE shown above) (siRNA 6 in FIG. 8)

```
5'-AGGCCUGAAGCAGUCAGUUUU-3'       (SEQ ID NO: 49)

3'-UUUCCGGACUUCGUCAGUCAA-5'       (SEQ ID NO: 50)

mLCE-siRNA-7 (siRNA m7 in FIG. 8)
5'-UCCCAUAUGGUGCAGCUAAUU-3'       (SEQ ID NO: 51)

3'-UUAGGGUAUACCACGUCGAUU-5'       (SEQ ID NO: 52)

mLCE-siRNA-11 (siRNA m11 in FIG. 8)
5'-GCAUCCGUUGUUCAGUUGCUU-3'       (SEQ ID NO: 53)

3'-UUCGUAGGCAACAAGUCAACG-5'       (SEQ ID NO: 54).
```

Example 10

Effect of LCE RNAi on FAS mRNA Expression in 3T3-L1 Cells

Twenty-four hours after transfection of siRNA (hLCE-siRNA-6) into 3T3-L1 cells differentiated to adipocytes, the total RNA was purified from the cells. After preparing cDNA from the obtained total RNA by reverse transcription reaction, the mouse FAS mRNA expression was measured by TaqMan PCR with an ABI Prism 7700 Sequence Detector System. A standard curve was drawn using a mouse FAS cDNA fragment prepared by PCR. The expression level of FAS was normalized based on β-actin expression.

The primers and probes used for the measurement were as follows.

```
TaqMan probe for mouse FAS
mFAS-P2:
5'-ATG CTG GCC AAA CTA ACT ACG GCT (SEQ ID NO: 55)
TCG-3'

TaqMan primer for mouse FAS
mFAS-F2:
5'-TGG CCT TCT CCT CTG TAA GCT    (SEQ ID NO: 56)
G-3' mFAS-R2:
5'-CTG TTC ACA TAT ACG CTC CAT    (SEQ ID NO: 57)
GG-3'

PCR primer for construction of mouse FAS cDNA
mFAS-5541S:
5'-TTC CGC TAC ATG GCT CAG GG-3'  (SEQ ID NO: 58)

mFAS-7551A:
5'-CCC GTA CAC TCA CTC GTG GC-3'  (SEQ ID NO: 59)
```

Also, siRNA (hLCE-siRNA-6) was transfected into 3T3-L1 cells differentiated to adipocytes, and after 24 hours there was added $^{14}C$-labeled sodium acetate to the medium. Four hours after this addition, the cells were lysed with 0.1% SDS, a 15% potassium hydroxide-methanol solution was added, and saponification was performed by heating at 75° C. for 45 minutes. After adding 5N hydrochloric acid thereto, the lipid components were extracted with chloroform:methanol (2:1). The extracted lipid components were fractionated by thin-layer chromatography using silica gel G (hexane:diethyl ether:acetic acid=80:20:1), and the $^{14}C$ acetate incorporated into the fatty acid fraction was measured to determine the fatty acid synthesis ability. As a control there were used 3T3-L1 cells into which siRNA having a sequence with no mammalian gene homology (scramble siRNA Duplex: Dharmacon, Inc.) had been transfected.

Figure 9:
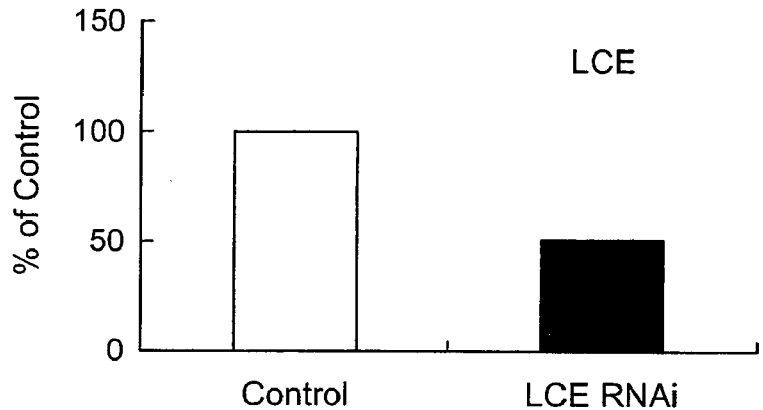
FIG. 9 is a set of graphs showing the results of (a) the suppression of LCE expression (b) the suppression of FAS expression and (c) fatty acid synthesis inhibition by RNAi.
Figure 9:
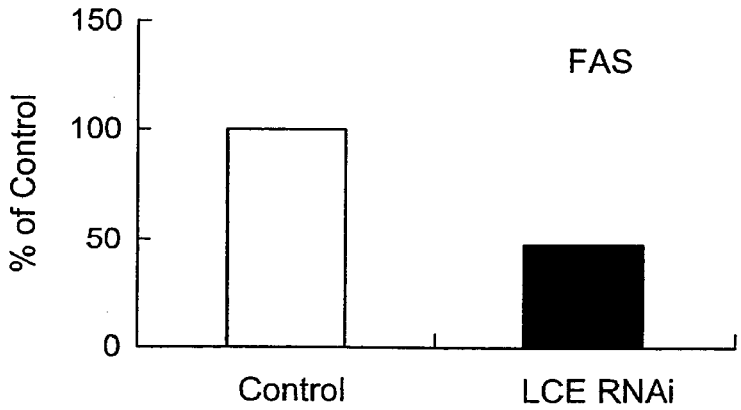
Figure 9:
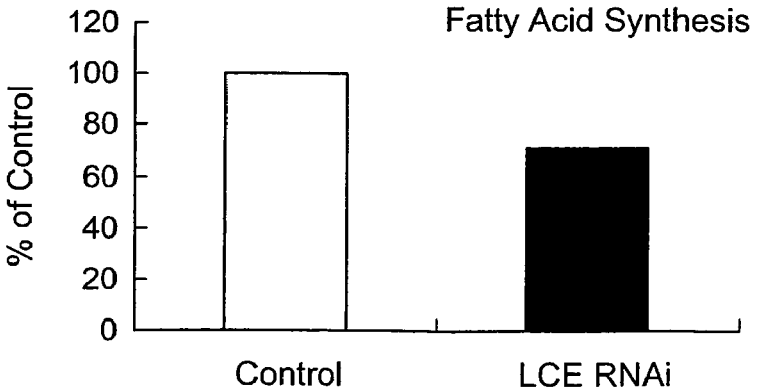

FIG. 9 is a set of graphs showing the results of (a) the suppression of LCE expression (b) the suppression of FAS expression and (c) fatty acid synthesis inhibition by RNAi. As shown in FIG. 9, it was confirmed that suppression of LCE expression inhibits synthesis of fatty acids.

Example 11

Effect of LCE RNAi on Apolipoprotein B Secretion in HepG2 Cells

Forty-eight hours after transfection of siRNA (hLCE-siRNA-6) into HepG2 cells, the medium was exchanged. Incubation was initiated 48 hours after medium exchange, and the culture supernatant was collected and used for quantitation of apolipoprotein secreted in the medium. The quantitation of apolipoprotein was carried out by microplate EIA (APO B TEST, Exocell Inc.). A standard solution of apolipoprotein B was used to draw a standard curve, and the apolipoprotein B concentration in the culture supernatant was determined. As a control there were used HepG2 cells into which siRNA having a sequence with no mammalian gene homology (scramble siRNA Duplex: Dharmacon, Inc.) had been transfected.

Figure 10:
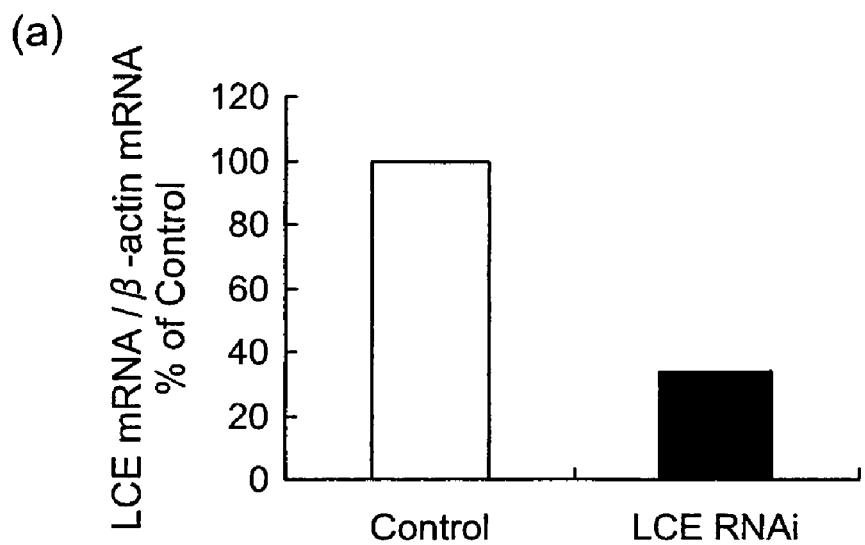
FIG. 10 is a pair of graphs showing (a) suppression of LCE expression and (b) apolipoprotein B secretion inhibition by RNAi.
Figure 10:
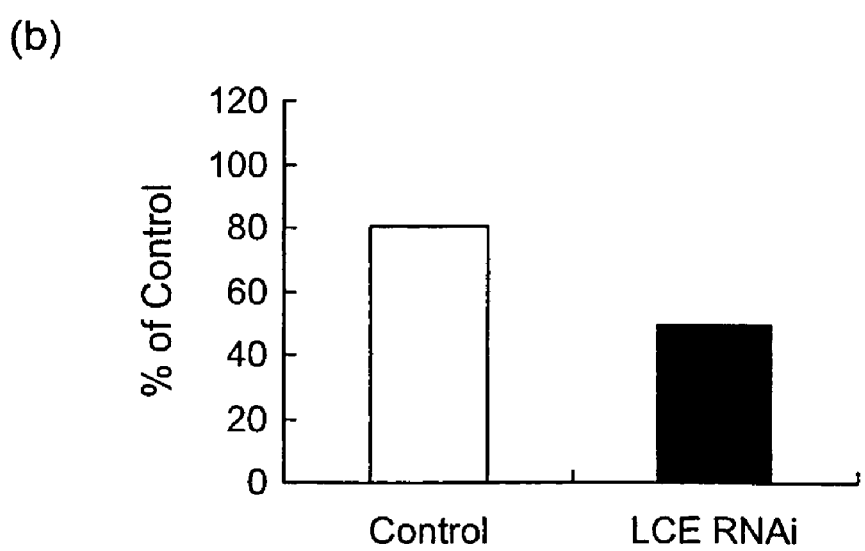

FIG. 10 is a pair of graphs showing (a) the suppression of the LCE expression and (b) apolipoprotein B secretion inhibition by RNAi. As shown in FIG. 10, it was confirmed that suppression of LCE expression inhibits apolipoprotein B secretion.

This result suggested that suppression of LCE activity produces an effect against obesity.

Example 12

Effect of LCE RNAi in DIO Mice

Seven-week-old mice (ICR, female) were raised for 23 weeks on a high-calorie MHF diet to induce obesity. First, the body weights of the mice were measured before administration of siRNA. The siRNA (hLCE-siRNA-6) was injected though the caudal vein of each mouse using HVJ-liposomes as the carrier (40 µg/mouse/injection). Administration was performed 5 times every other day, and two days after the final administration, the mouse body weights were again measured and the weight changes before and after siRNA administration were determined. Blood was collected from the orbital venous plexus for measurement of the blood glucose levels. Blood was also collected from the abdominal vena cava for at of the plasma insulin levels. As a control there were used mice injected with scramble siRNA which exhibits no effect in mammalian cells.

Figure 11:
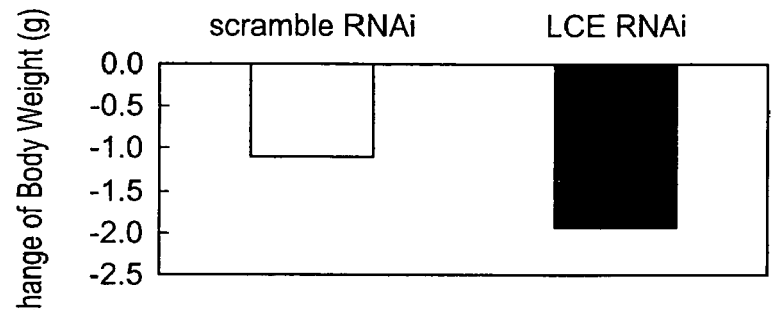
FIG. 11 is a set of graphs showing changes in (a) body weight, (b) blood glucose and (c) plasma insulin upon siRNA administration. "scramble RNAi" represents the control wherein RNAi was carried out using scramble siRNA which exhibits no effect in mammals.
Figure 11:
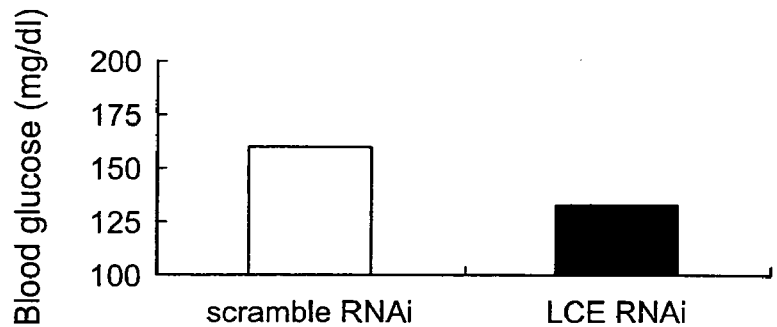
Figure 11:
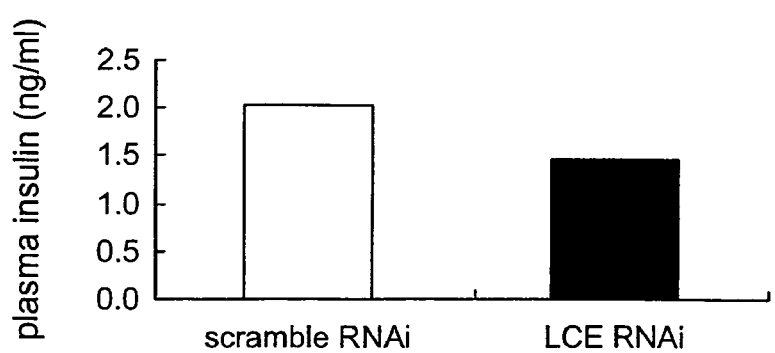

FIG. 11 is a set of graphs showing change in (a) body weight, (b) blood glucose and (c) plasma insulin upon siRNA administration. As shown in FIG. 11, it was confirmed that administration of siRNA for LCE to mice reduced body weight. In addition, since both blood glucose levels and plasma insulin levels were reduced, it was confirmed on the individual level that siRNA for LCE suppress LCE activity and exhibits an improving effect on obesity.

The total RNA was purified from the mouse livers and cDNA was obtained by reverse transcription reaction. The expression levels of mouse LCE mRNA, mouse acetyl-CoA carboxylase (ACC) mRNA, mouse FAS mRNA, mouse SCD-1 mRNA, mouse SREBP-1c mRNA and mouse insulin receptor substrate (IRS)-2 mRNA were measured by TaqMan PCR with an ABI Prism 7700 Sequence Detector System. A standard curve was drawn using a cDNA fragment for each gene, prepared by PCR. The expression level of each gene was normalized based on β-actin expression.

The base sequences of the primers and probes used for measurement were as follows.

```
TaqMan probe for mouse ACC1
5'-AGC TGC AAG CCT GTC ATC CTC AAT    (SEQ ID NO: 73)
ATC G-3'

TaqMan PCR primer for mouse ACC1
forward:
5'-TTC TGA ATG TGG CTA TCA AGA CTG    (SEQ ID NO: 74)
A-3' reverse:
5'-TGC TGG GTG AAC TCT CTG AAC        (SEQ ID NO: 75)
A-3'

Primer for construction of mouse ACC1 cDNA
forward:
5'-TAG TGT CAG CGA TGT TCT GT-3'      (SEQ ID NO: 76)

reverse:
5'-AAA TCT CTG ATC CAC CTC AC-3'      (SEQ ID NO: 77)

TaqMan probe for mouse SCD-1
ACT CGC CTA CAC CAA CGG GCT CC        (SEQ ID NO: 78)

TaqMan primer for mouse SCD-1
forward:
5'-TTT CCA AGC GCA GTT CCG-3'         (SEQ ID NO: 79)

reverse:
5'-ATC GAG CGT GGA CTT CGG T-3'       (SEQ ID NO: 80)

PCR primer for construction of mouse SCD-1 cDNA
forward:
5'-CAC CCA TCC CGA GAG TCA GG-3'      (SEQ ID NO: 81)

reverse:
5'-GTG GGC CGG CAT GAT GAT AG-3'      (SEQ ID NO: 82)

TaqMan probe for mouse SREBP-1c
5'-CTT CAA ATG TGC AAT CCA TGG CTC    (SEQ ID NO: 83)
CGT-3'

TaqMan primer for mouse SREBP-1c
forward:
5'-GTA GCG TCT GCA CGC CCT A-3'       (SEQ ID NO: 84)

reverse:
5'-CTT GGT TGT TGA TGA GCT GGA        (SEQ ID NO: 85)
G-3'

PCR primer for construction of mouse SREBP-1c cDNA
forward:
5'-AAG CTG TCG GGG TAG CGT CT-3'      (SEQ ID NO: 86)

reverse:
5'-AGG CTC GAG TAA CCC AGC AC-3'      (SEQ ID NO: 87)

TaqMan probe for mouse IRS-2
5'-ACT TAG CCG CTT CAA GCC CGA        (SEQ ID NO: 88)
TGT G-3'

TaqMan PCR primer for mouse IRS-2
forward:
5'-AGA AGG TGC CCG AGT GGC-3'         (SEQ ID NO: 89)

reverse:
5'-CCC CAG ATA CCT GAT CCA TGA-3'     (SEQ ID NO: 90)

Primer for construction of mouse IRS-2 cDNA
forward:
5'-CAG TAG GCT CCA TGG ATG GC-3'      (SEQ ID NO: 91)
```

-continued

```
reverse:
5'-ATG ACC TTA GCA CCC CGG TG-3'    (SEQ ID NO: 92)
```

Figure 21:
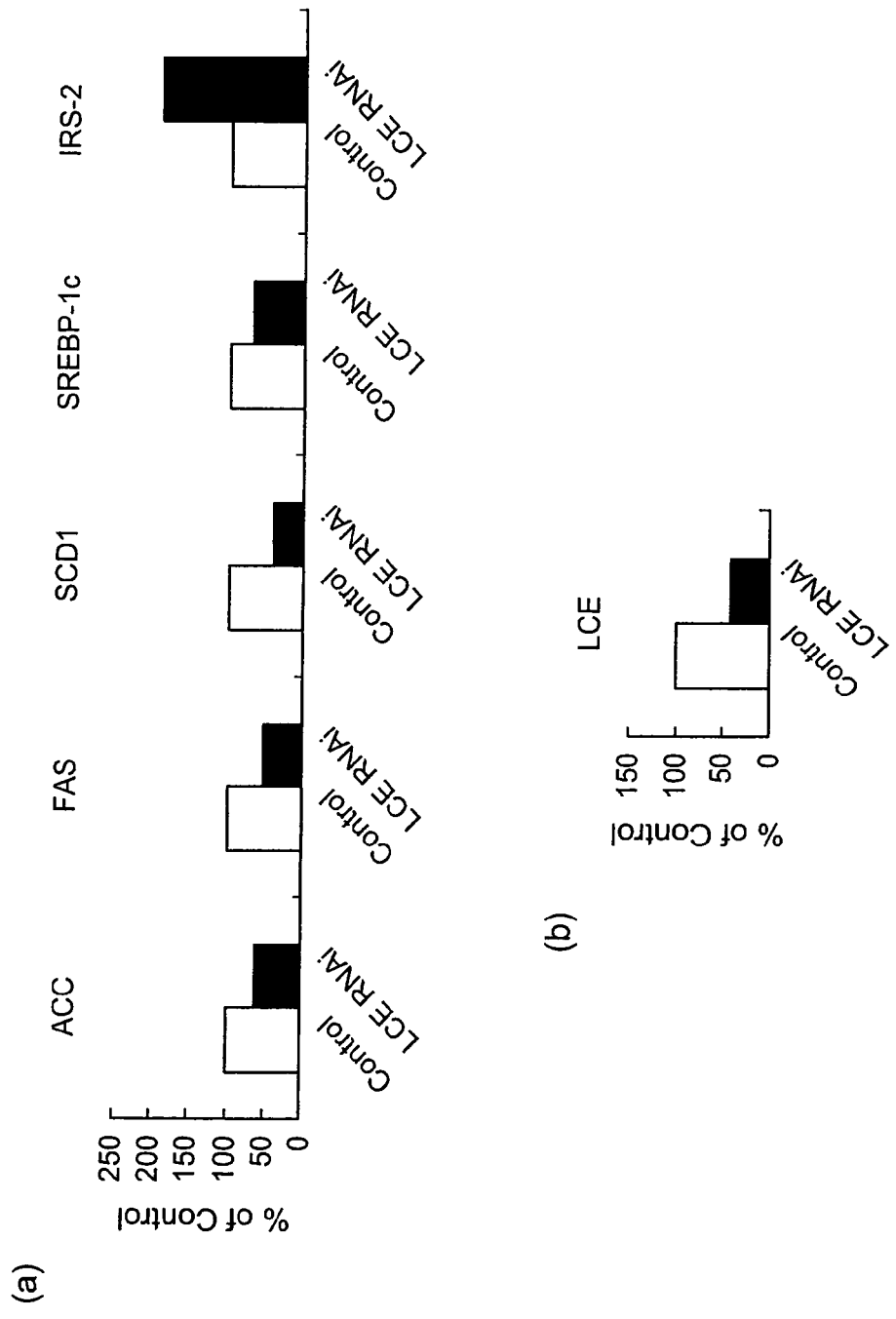
FIG. 21 is a pair of graphs showing (a) ACC, FAS, SCD1, SREBP-1c and IRS-2 and (b) LCE mRNA expression level in the livers of siRNA-administered mice.

FIG. 21 is a pair of graphs showing (a) ACC, FAS, SCD1, SREBP-1c and IRS-2 and (b) LCE mRNA expression levels in the livers of siRNA-administered mice. It was confirmed that suppression of LCE expression lowers expression of the fatty acid synthesis enzymes ACC, FAS and SCD1, while also lowering expression of SREBP-1c, a transcription factor which regulates fatty acid synthesis. In other words, this suggested that suppression of LCE expression in DIO mouse liver inhibits fat synthesis in the liver.

Moreover, the enhanced expression of IRS-2 (insulin receptor substrate-2) in LCE RNAi-administered mouse livers suggests that suppression of LCE expression in the liver also increases insulin sensitivity in the liver. The present inventors believe that this is the reason for the reduction in blood glucose levels and plasma insulin levels induced by suppression of LCE expression as demonstrated in Example 12.

Example 13

Effect of LCE RNAi on Cellular Fatty Acid Composition of HepG2 Cells

Seventy-two hours after transfection of siRNA (hLCE-siRNA-6) into HepG2 cells, the cells were harvested. They were then disrupted by sonication in phosphate buffer, and after adding C17:0 triglycerides, cholesteryl esters and phospholipids as internal standard substances, the lipid components were extracted by Bligh-Dyer method. The obtained lipids were dried to hardness under a nitrogen stream, and then fractionated by thin-layer chromatography using silica gel G (hexane:diethyl ether:acetic acid=80:20:1) for separation of the triglycerides, cholesteryl esters and phospholipids. The fatty acid residues of the three factions were methylated with 5% hydrochloric acid-methanol, and the fatty acid composition was analyzed using gas chromatography (GC-FID). As a control there were used HepG2 cells into which siRNA having a sequence with no mammalian gene homology (scramble siRNA Duplex: Dharmacon, Inc.) had been transfected.

Table 2 shows the results of fatty acid composition analysis. As the results in Table 2 clearly demonstrate, it was confirmed that suppression of LCE expression by RNAi reduces the component ratio of C18 or more fatty acids in triglycerides, cholesteryl esters and phospholipids.

TABLE 2

|  |  | C16:0 | C16:1 | C18:0 | C18:1 | C16/C18 |
|---|---|---|---|---|---|---|
| Triglyc-erides | Control | 34.3 | 16.3 | 8.7 | 29.0 | 1.34 |
|  | hLCE-siRNA-6 | 37.3 | 16.1 | 7.7 | 26.1 | 1.58 |
| Choles-teryl esters | Control | 23.6 | 7.0 | 18.6 | 36.1 | 0.56 |
|  | hLCE-siRNA-6 | 26.5 | 7.7 | 18.8 | 37.7 | 0.61 |
| Phospho-lipids | Control | 29.1 | 20.4 | 9.1 | 25.3 | 1.44 |
|  | hLCE-siRNA-6 | 30.4 | 23.2 | 8.1 | 21.5 | 1.81 |

Example 14

Effect of LCE RNAi on Expression of Other Genes in HepG2 Cells

The effect suppression of LCE expression was also examined with respect to SREBP-1 (sterol regulatory element binding protein-1) which is involved in fatty acid synthesis and SREBP-2 (sterol regulatory element binding protein-2) which is involved in cholesterol synthesis. Total RNA was purified from siRNA (hLCE-siRNA-6)-transfected HepG2 cells, and cDNA was obtained by reverse transcription reaction. The human SREBP-1 mRNA and human SREBP-2 mRNA expression levels were measured by TaqMan PCR with an ABI Prism 7700 Sequence Detector System. As a control there were used HepG2 cells into which siRNA having a sequence with no mammalian gene homology (scramble siRNA Duplex: Dharmacon, Inc.) had been transfected. A standard curve was drawn using the human SREBP-1 cDNA fragment and human SREBP-2 cDNA fragment prepared by PCR. The expression level of each gene was normalized based on β-actin expression.

The base sequences of the primers used for measurement were as follows.

```
TaqMan primer for human SREBP-1
forward:
5'-CAA CAC AGC AAC CAG AAA CTC    (SEQ ID NO: 60)
AAG-3' reverse:
5'-TTG CTT TTG TGG ACA GCA GTG-3'  (SEQ ID NO: 61)

PCR primer for construction of human SREBP-1 cDNA
forward:
5'-CGG AGA AGC TGC CTA TCA AC-3'   (SEQ ID NO: 62)

reverse:
5'-GGT CAG TGT GTC CTC CAC CT-3'   (SEQ ID NO: 63)

TaqMan primer for human SREBP-2
forward:
5'-GAT ATC GCT CCT CCA TCA ATG     (SEQ ID NO: 64)
AC-3' reverse:
5'-ACT TGT GCA TCT TGG CGT CTG-3'  (SEQ ID NO: 65)

PCR primer for construction of human SREBP-2 cDNA
forward:
5'-CAT TCT GAC CAC AAT GCC TG-3'   (SEQ ID NO: 66)

reverse:
5'-AGT AGG GAG AGA AGC CAG CC-3'   (SEQ ID NO: 67)
```

Figure 12:
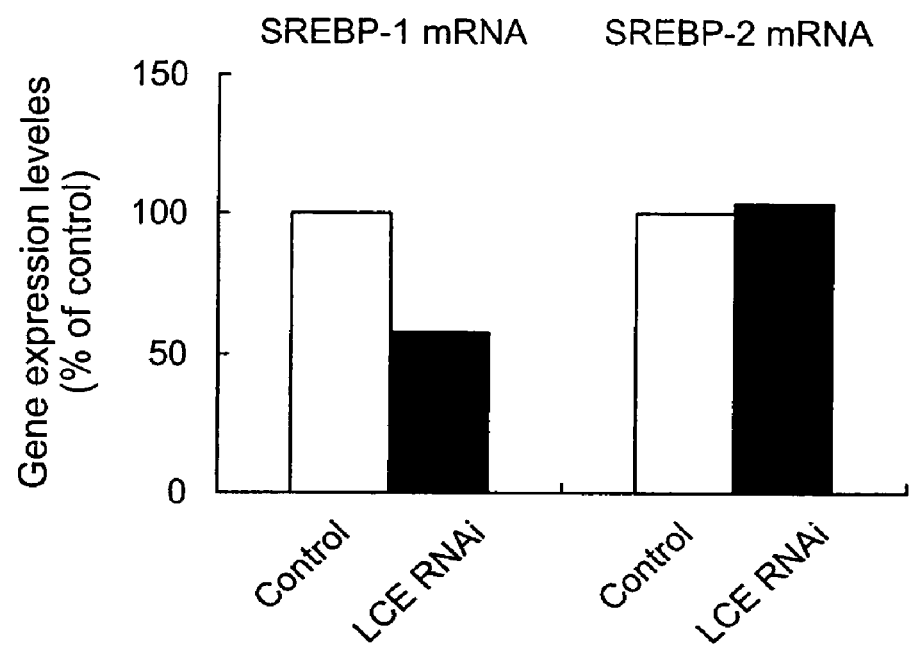
FIG. 12 is a graph showing expression of SREBP-1 and SREBP-2 mRNA in siRNA-transfected HepG2 cells.

FIG. 12 is a graph showing expression of SREBP-1 and SREBP-2 mRNA in siRNA-transected HepG2 cells. As shown in FIG. 12, it was confirmed that transfection of siRNA significantly reduces expression of SREBP-1 but does not alter expression of SREBP-2.

Example 15

Effect of LCE RNAi on Cellular Lipid Synthesis in HepG2 Cells

Seventy-two hours after transfection of siRNA (hLCE-siRNA-6) into HepG2 cell, $^{14}$C-labeled sodium acetate was added to the medium. Four hours after this addition, the cells were lysed with 0.1% SDS. A 15% potassium hydroxide-methanol solution was added to a portion of the cell lysate, and saponification was performed by heating at 75° C. for 45 minutes. After adding 5N hydrochloric acid thereto, the lipid components were extracted with chloroform:methanol (2:1). The extracted lipid components were fractionated by thin-layer chromatography using silica gel G (hexane:diethyl ether:acetic acid=80:20:1), and the $^{14}C$ acetate incorporated into the fatty acid fraction was measured to determine the fatty acid synthesis ability The lipid components were again extracted directly from the cell lysate portion with chloroform:methanol (2:1). The obtained lipid components were fractionated by thin-layer chromatography, and the $^{14}C$ acetate incorporated into the triglyceride fraction was measured to determine the triglyceride synthesis ability. The values for the fatty acid synthesis ability and triglyceride synthesis ability were normalized based on the protein in the cell lysate. As a control there were used HepG2 cells into which siRNA having a sequence with no mammalian gene homology (scramble siRNA Duplex: Dharmacon, Inc.) had been transfected.

Figure 13:
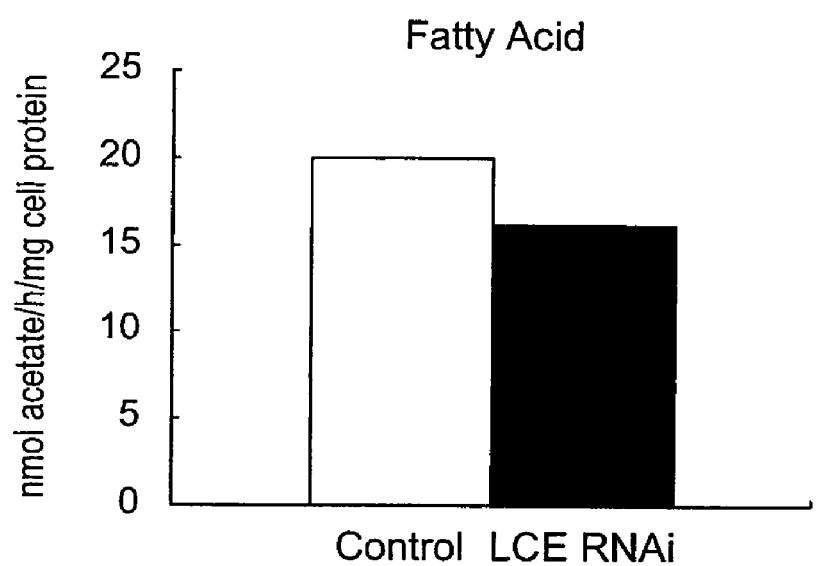
FIG. 13 is a pair of graphs showing (a) fatty acid synthesis and (b) triglyceride synthesis ability of siRNA-transfected HepG2 cells.
Figure 13:
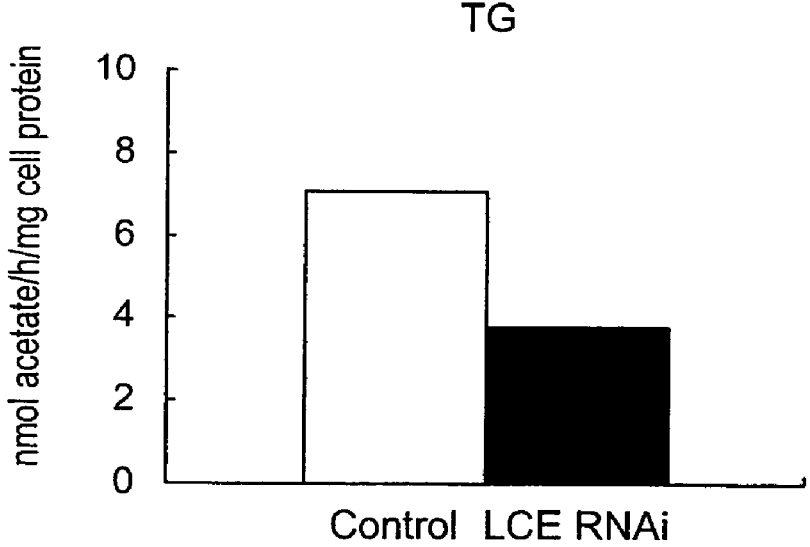

FIG. 13 is a pair of graphs showing (a) fatty acid synthesis and (b) triglyceride synthesis ability of siRNA-transfected HepG2 cells. As shown in FIG. 13, it was confirmed that suppression of LCE expression by transfection of siRNA reduces fatty acid synthesis ability and triglyceride synthesis ability.

Example 16

Effect of LCE RNAi on Cellular Triglyceride Contents in HepG2 Cells

Seventy-two hours after transfection of siRNA (hLCE-siRNA-6) into HepG2 cells, the cells were harvested. They were then disrupted by sonication in phosphate buffer, and the lipid components were extracted from a portion thereof by Bligh-Dyer method. The obtained lipids were dried to hardness under a nitrogen stream and dissolved in 2-propanol, and the triglycerides were measured by an enzyme method. The obtained value for the triglyceride content was normalized based on the protein content in the solution of the cells disrupted by sonication. As a control there were used HepG2 cells into which siRNA having a sequence with no mammalian gene homology (scramble siRNA Duplex: Dharmacon, Inc.) had been transfected.

Figure 14:
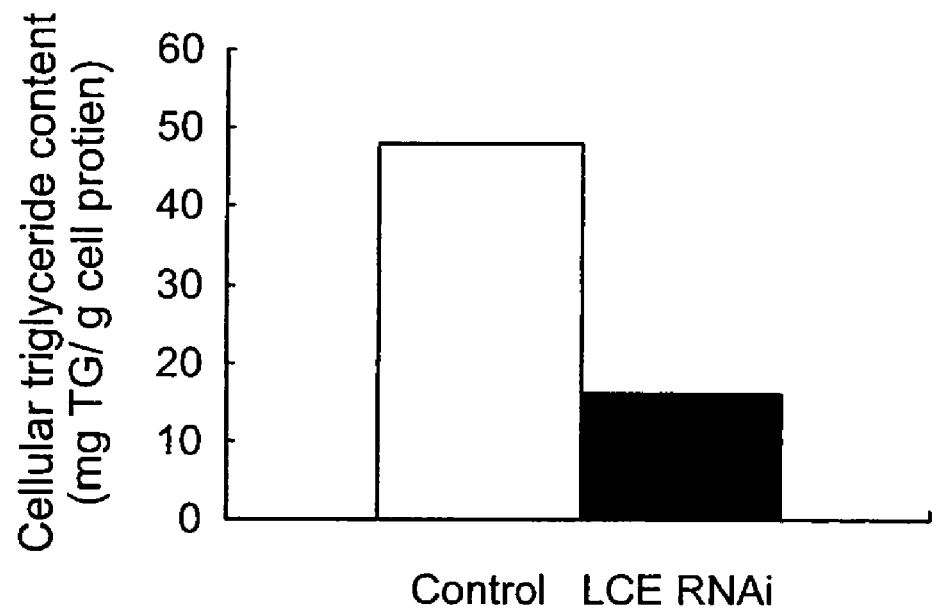
FIG. 14 is a graph showing triglyceride amount in siRNA-transfected HepG2 cells.

FIG. 14 is a graph showing triglyceride amount in siRNA-transfected HepG2 cells. As shown in FIG. 14, it was confirmed that suppression of LCE expression by transfection of siRNA reduces intracellular triglyceride content.

Example 17

Effect of LCE RNAi on Cellular Fatty Acid Oxidation in HepG2 Cells

Seventy-two hours after transfer of siRNA (hLCE-siRNA-6) into HepG2 cells, $^{14}C$-palmitic acid was added to the medium. After 30 minutes of incubation, the medium was transfected to a separate tube and 10% trichloroacetic acid was added. The $CO_2$ released from the medium was trapped with a 10% aqueous sodium hydroxide. The specific radioactivity of the trapped $CO_2$ was measured, and the volume of $CO_2$ produced by β-oxidation from the palmitate added to the medium was determined. The $CO_2$-released medium was centrifuged, the specific radioactivity of the acid-soluble fraction of the supernatant was measured, and the quantity of ketone bodies produced by β-oxidation from the palmitate added to the medium was determined. After removal of the medium, the incubated HepG2 cells were lysed with 0.1% SDS. The lipid components were extracted from a portion of the cell lysate with chloroform:methanol (2:1), and were fractionated by thin-layer chromatography. The specific radioactivity of the triglyceride fraction was measured, to determine the amount of palmitate added to the medium which was incorporated into the triglycerides in the cells. The values for the $CO_2$ volume, ketone body concentration and triglyceride incorporation were normalized based on the protein in the cell lysate. As a control there were used HepG2 cells into which siRNA having a sequence with no mammalian gene homology (scramble siRNA Duplex: Dharmacon, Inc.) had been transfected.

Figure 15:
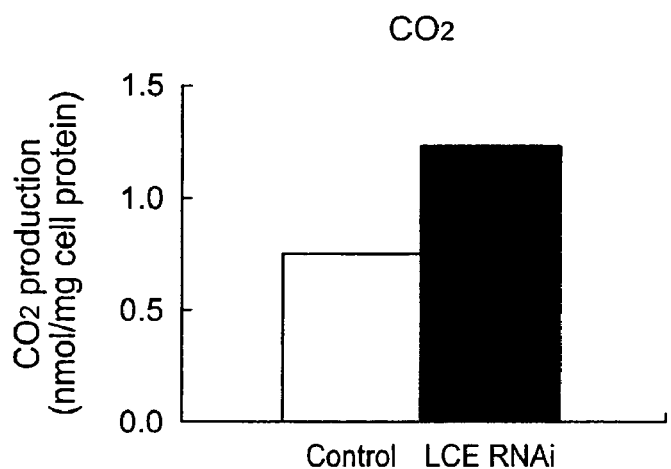
FIG. 15 is a set of gas showing (a) $CO_2$ production, (b) ketone body production and (c) palmitate incorporation into triglycerides, for siRNA-transfected HepG2 cells.
Figure 15:
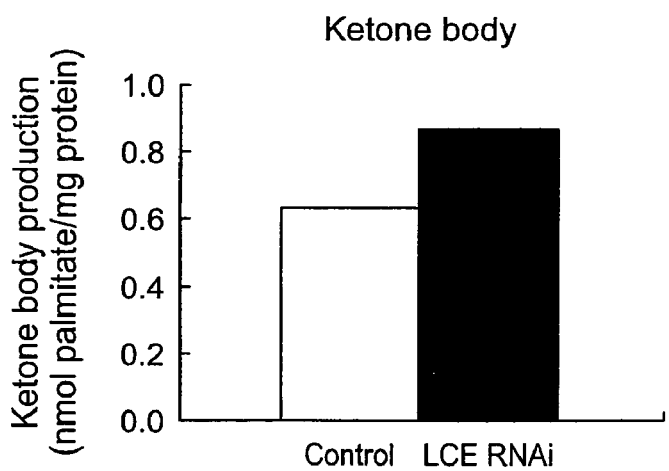
Figure 15:
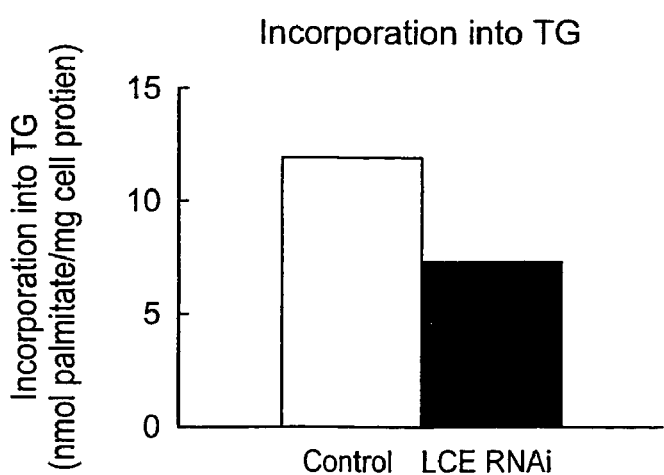

FIG. 15 is a set of graphs showing (a) $CO_2$ production, (b) ketone body production and (c) palmitate incorporation into triglycerides, for siRNA-transfected HepG2 cells. As shown in FIG. 15, it was confirmed that suppression of LCE expression by siRNA transfection increases $CO_2$ production and ketone body production, while reducing incorporation of palmitate into triglycerides. Since fatty acid combustion is accompanied by $CO_2$ and ketone body production, this result suggests that suppression of LCE expression promotes fatty acid combustion.

Example 18

Effect of LCE RNAi on Cellular CPT-1 Expression in HepG2 Cells

The effect of suppression of LCE expression on CPT-1 (carnitine palmitoyl transferase-1), a transporter which uptakes fatty acids into mitochondria, was examined. Seventy-two hours after transfection of siRNA (hLCE-siRNA-6) into HepG2 cells, the cells were harvested. The total RNA was purified from the cells and used for reverse transcription reaction to obtain cDNA. The human CPT-1 mRNA expression was measured by TaqMan PCR with an ABI Prism 7700 Sequence Detector System. As a control there were used HepG2 cells into which siRNA having a sequence with no mammalian gene homology (scramble siRNA Duplex: Dharmacon, Inc.) had been transfected. A standard curve was drawn using the human CPT-1 cDNA fragment prepared by PCR. The obtained value was normalized based on β-actin expression.

The base sequences of the primers and probes used for measurement were as follows.

```
TaqMan probe for human CPT-1
5'-CCG GGA GGA AAT CAA ACC AAT TCG  (SEQ ID NO: 68)
TC-3'

TaqMan primer for human CPT-1
forward:
5'-TGC TTT ACA GGC GCA AAC TG-3'    (SEQ ID NO: 69)

reverse:
5'-TGG AAT CGT GGA TCC CAA A-3'     (SEQ ID NO: 70)

PCR primer for construction of human CPT-1 cDNA
forward:
5'-ATT TGA AGT TAA AAT CCT GGT GGG  (SEQ ID NO: 71)
C-3' reverse:
5'-TTC CCA CGT CCA AAA TAG GC-3'    (SEQ ID NO: 72)
```

Figure 16:
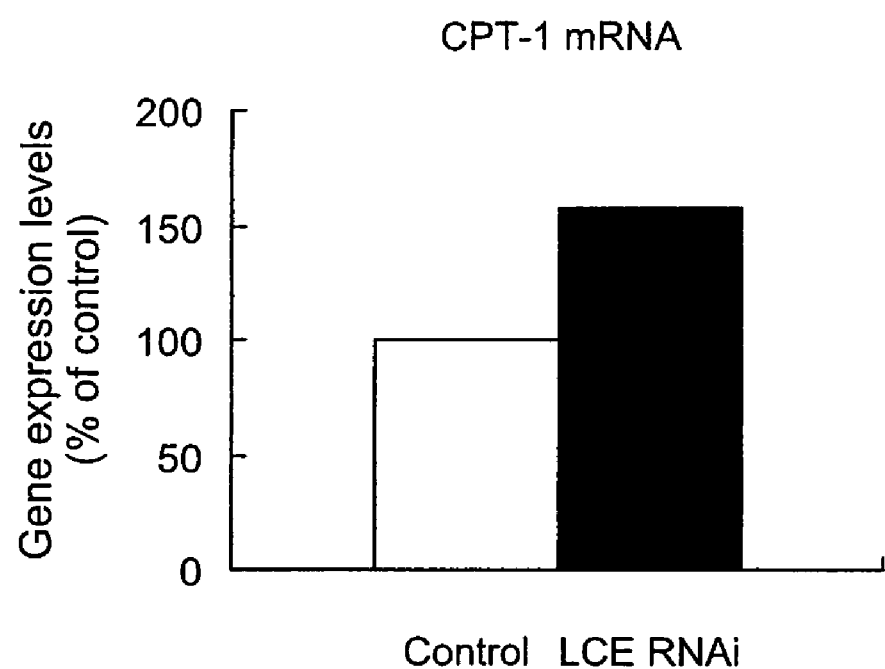
FIG. 16 is a graph showing CPT-1 mRNA expression in siRNA-transfected HepG2 cells.

FIG. 16 is a graph showing CPT-1 mRNA expression in siRNA-transfected HepG2 cells. As shown in FIG. 16, it was confirmed that suppression of LCE expression by transfection of siRNA increases CPT-1 expression.

Example 19

Change in LCE Expression in Livers of Mice Fed a High-sucrose Diet

Eight-week-old mice (ICR, male) were raised for 3 days on a high-sucrose diet (67% sucrose), and 7-week-old mice (ICR, male) were raised for 10 days on the high-sucrose diet. After body weight measurement, the mice were euthanized, and the epididymal adipose tissue was extracted and weighed. The mouse livers were also extracted, the total RNA was purified, and the LCE mRNA expression levels in the liver were measured by TaqMan PCR. The LCE mRNA expression levels were normalized based on β-actin expression. As a control there were used mice raised on an ordinary diet (CA-1).

Figure 17:
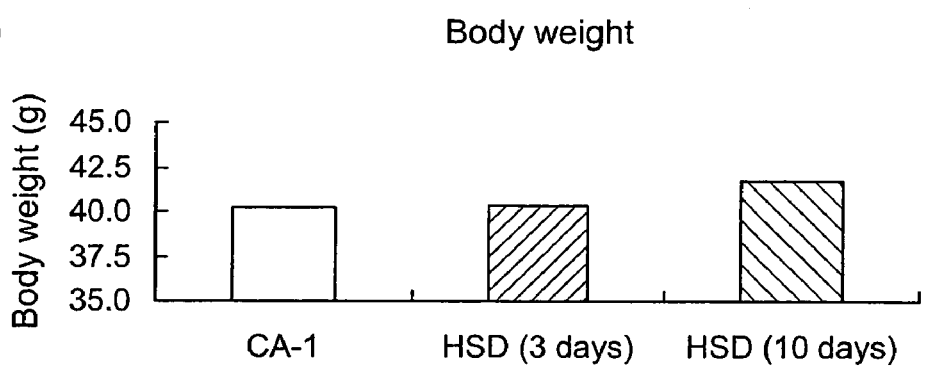
FIG. 17 is a set of graphs showing (a) body weight, (b) epididymal white adipose tissue weight and (c) liver LCE mRNA expression in mice fed with a high-sucrose diet CA-1 represents mice fed with a normal diet, and HSD (3 days) and HSD (10 days) represent mice fed with a high-sucrose diet for 3 days and 10 days, respectively.
Figure 17:
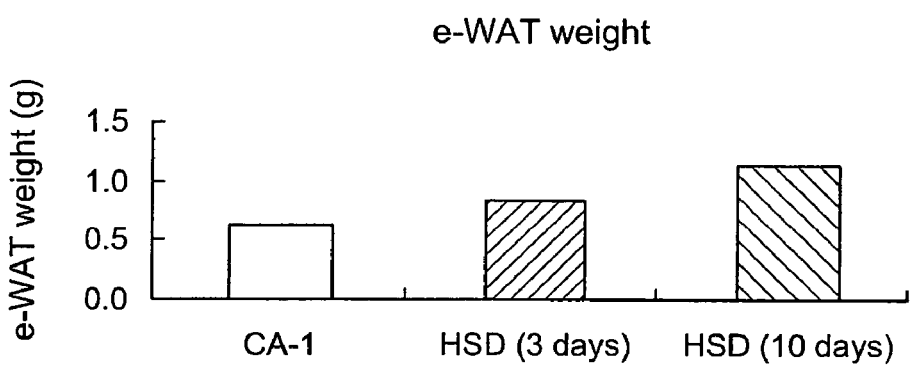
Figure 17:
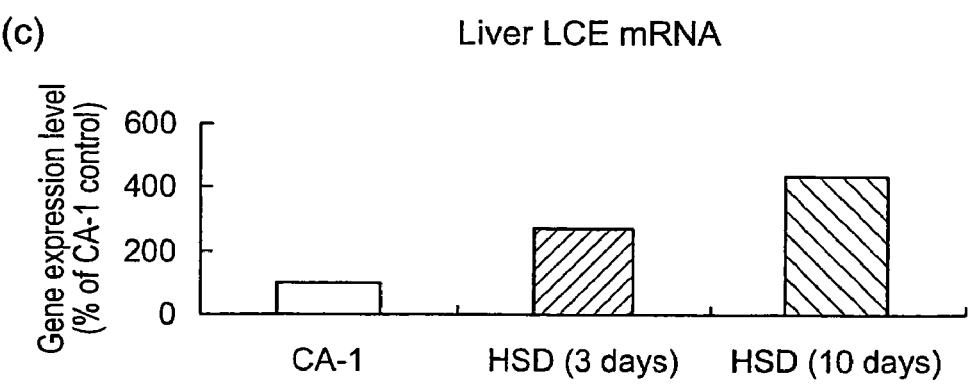

FIG. 17 is a set of graphs showing (a) body weights, (b) epididymal adipose tissue weights and (c) liver LCE mRNA expression in the mice which were fed a high-sucrose diet. As shown in FIG. 17, it was confirmed that high-sucrose diet feeding increases mouse body weight and adipose tissue weight, while also increasing LCE mRNA expression in the liver.

Example 20

LCE RNAi Administration to High-sucrose Diet-fed Mice

Using HVJ-liposomes as a carrier, siRNA (hLCE-siRNAi-6) was injected into mice (7-week-old, ICR, male) though the caudal vein (40 μg/mouse/injection). Immediately after the initial injection, the mice were raised on a high-sucrose diet. As a control, there were used mice injected with scramble siRNA which exhibits no effect in mammalian cells. The siRNA injection was performed 5 times every other day, and on the day following the final injection, the mouse body weights were measured, the body fat masses were determined with an NMR analyzer (Minispec; mq7.5), and the adipose weight/body weight ratios were calculated. Blood was collected from the abdominal vena cava for measurement of the plasma leptin levels.

Figure 18:
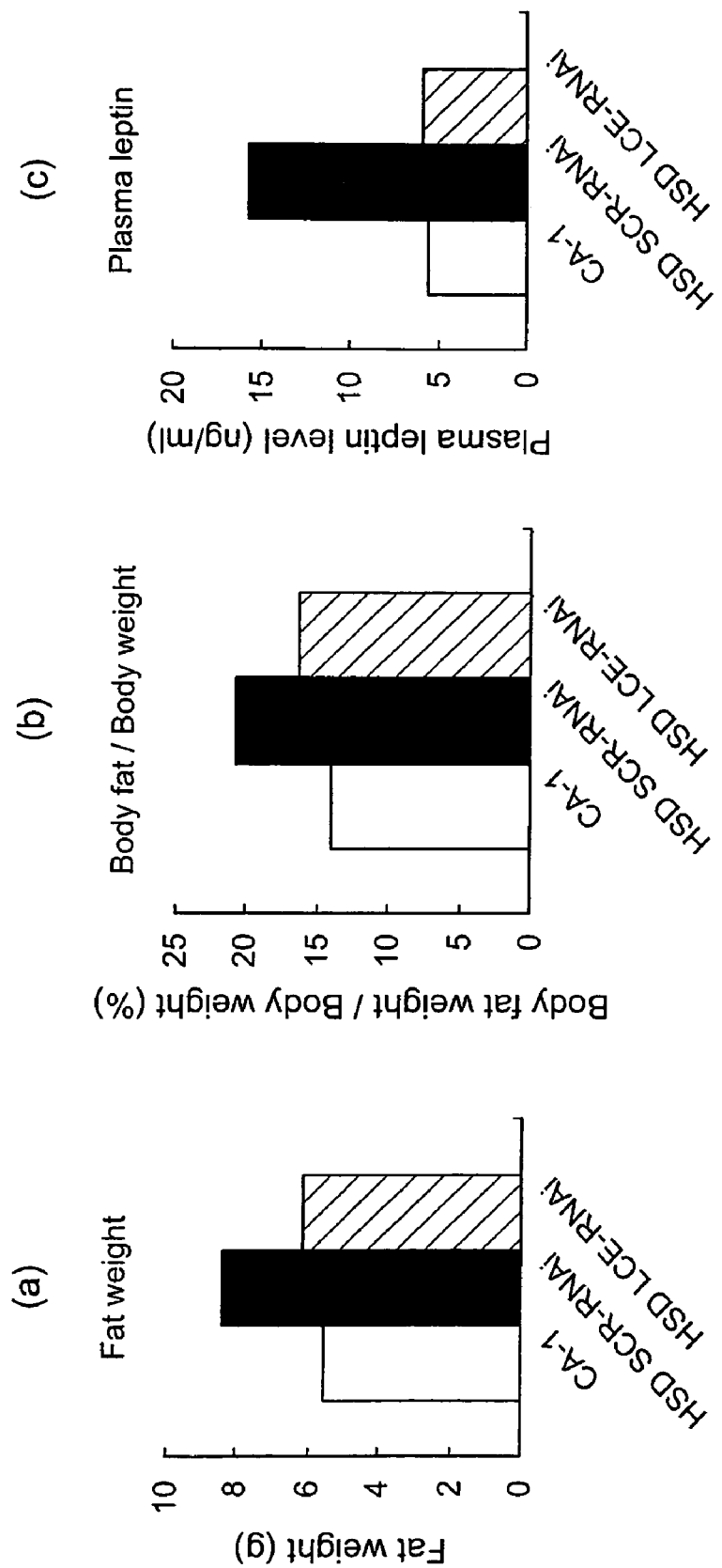
FIG. 18 is a set of graphs showing (a) fat weight, (b) body fat weight/body weight ratio and (c) plasma leptin level for mice administered with siRNA. HSD SCR-RNAi represents administration of scramble siRNA which exhibits no effect in mammals, to mice fed with a high-sucrose diet. HSD LCE-RNAi represents administration of hLCE-siRNA-6 to mice fed with a high-sucrose diet.

FIG. 18 is a set of graphs showing (a) fat weights, (b) body fat weight/body weight ratios and (c) plasma leptin levels for mice administered with siRNA. LCE expression inhibition by administration of LCE RNAi suppressed fat weight increase caused by the high-sucrose diet. Body fat weight/body weight ratio increase was likewise inhibited. This indicates that suppression of LCE expression prevents obesity induced by a high-sucrose diet (exhibits an anti-obesity effect). Moreover, since leptin is secreted from adipose tissue, increased adipose tissue weight results in elevated secreted leptin levels. In this experiment, the increase in leptin with the high-sucrose diet implies that the fat volume had increased, while the fact that increase in leptin levels was suppressed in the LCE RNAi-administered group implies that LCE RNAi administration had suppressed increase in adipose tissue weight.

After euthanasia of the mice and extortion of the livers, the total RNA was purified from a portion thereof and the LCE mRNA and FAS mRNA expression levels in the livers were measured by TaqMan PCR. The LCE mRNA and FAS mRNA expression levels were normalized based on β-actin expression levels. Portions of the livers were also homogenized in phosphate buffer and the lipid components were extracted by Bligh-Dyer method. The obtained lipids were dried to hardness under a nitrogen stream and dissolved in 2-propanol, and the triglycerides were measured by an enzyme method. The obtained value for the triglyceride content was normalized based on the protein content of the liver homogenate. Also, the microsome fraction was prepared from the liver tissue and the change in LCE protein level was assayed by Western blotting. For the Western blotting there were used anti-LCE polyclonal antibodies obtained by immunizing rabbits (SPF, Japanese White Rabbits) with the synthetic peptide "CFEAYIGKVKKATKAE" synthesized based on the amino acid sequence "FEAYIGKVKKATKAE" from the primary structure of mouse LCE protein.

Figure 19:
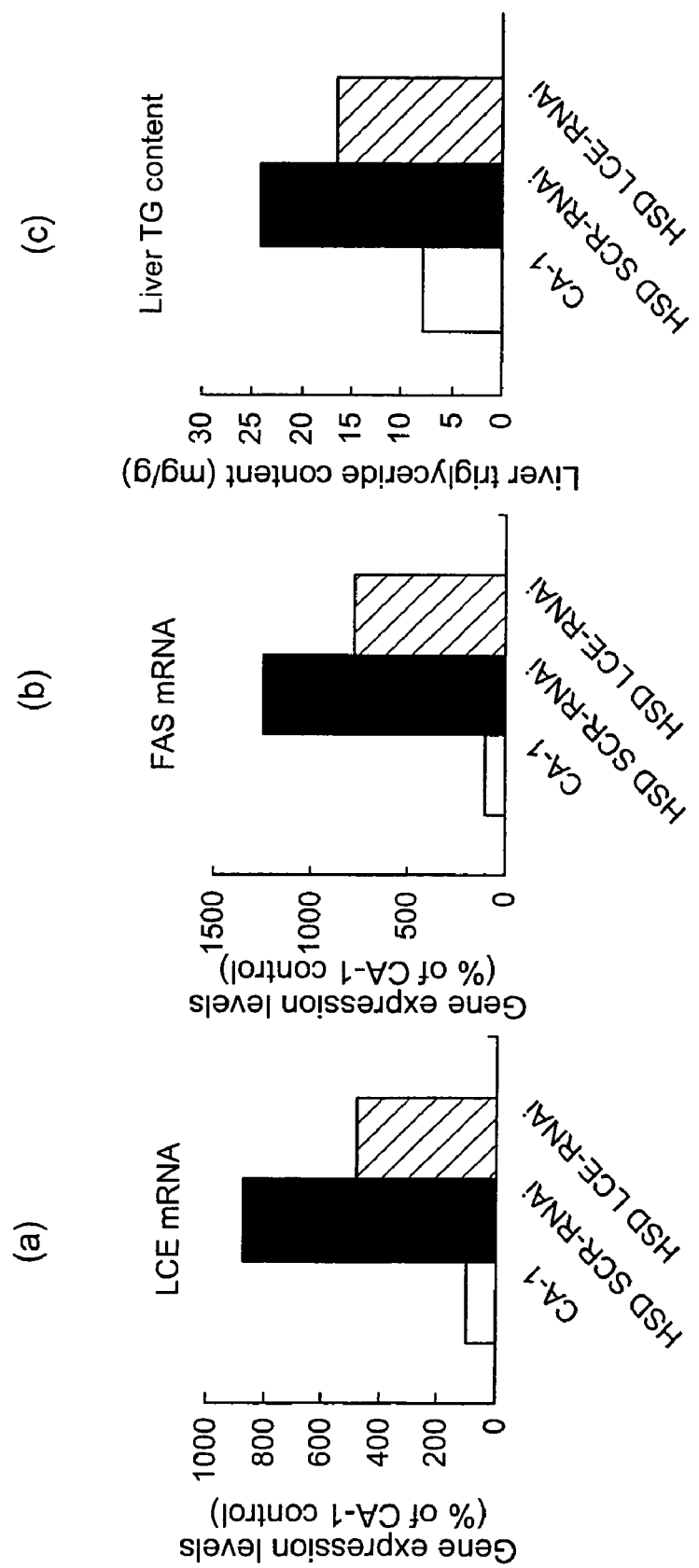
FIG. 19 is a set of graphs showing (a) LCE mRNA expression level, (b) FAS mRNA expression level and (c) liver triglyceride content for siRNA-administered mice.

FIG. 19 is a set of graphs showing (a) LCE mRNA expression levels, (b) FAS mRNA expression levels and (c) liver triglyceride contents for siRNA-administered mice. FIG. 19(a) confirmed that a high-sucrose diet promotes LCE expression in the liver, or in other words, that liver LCE expression is enhanced in the onset of obesity. Moreover, it was confirmed that LCE RNAi administration suppresses enhanced expression of LCE in mouse liver.

FIG. 19(b) suggested that FAS expression in liver is enhanced by a high-sucrose diet, or in other words, that fatty acid synthesis in liver is enhanced by a high-sucrose diet. It also suggested that suppression of LCE expression by administration of LCE RNAi suppresses enhanced expression of FAS and inhibits enhanced fatty acid synthesis.

FIG. 19(c) confirmed that fat accumulation in liver is enhanced by a high-sucrose diet. It was also confirmed that suppression of LCE expression by administration of LCE RNAi suppresses fat accumulation in liver during onset of obesity.

Thus, it was confined that fat synthesis in liver is enhanced by a high-sucrose diet (process for promoting obesity onset) and that fat synthesis enhancement is blocked by suppression of LCE expression (inhibition of obesity onset).

Figure 20:
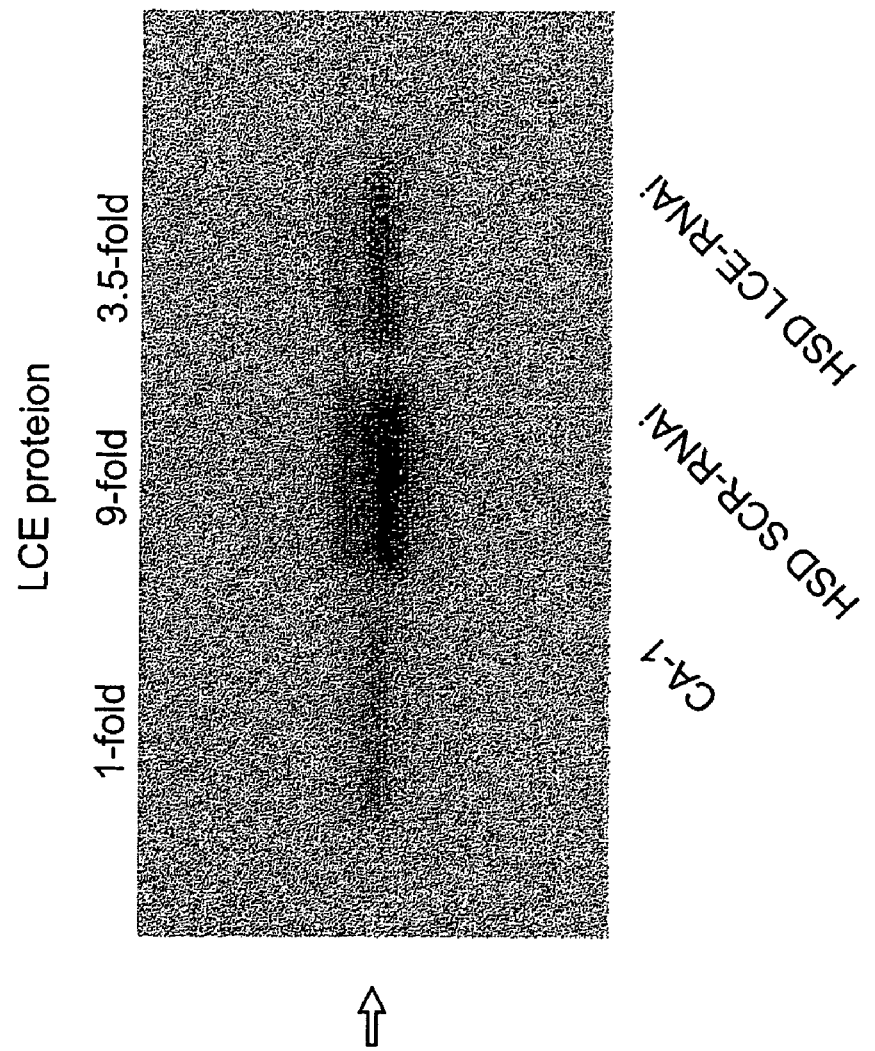
FIG. 20 is an image showing the change in LCE protein in the livers of siRNA-administered mice.

FIG. 20 is an image showing the change in LCE protein in the livers of siRNA-administered mice. The relationship between fatty acid synthesis and LCE expression shown in FIG. 19 could also be confirmed by LCE protein levels.

Example 21

Human LCE Amino Acid Substitution and Resulting Change in LCE Activity

Human LCE cDNA was constructed by PCR using a forward primer having BamHI site (hLCE-5BamHI) and a reverse primer having XhoI site (hLCE-3XhoI). The obtained cDNA fragment was subcloned into plasmid pCMV-Tag2B (Stratagene) using the added BamHI and XhoI sites (wild-type LCE construct).

The sequences of the primers used were as follows.

```
hLCE-5BBamHI:
GGA TCC AAC ATG TCA GTG TTG ACT T    (SEQ ID NO: 93)

hLCE-3XhoI:
CTC GAG CTA TTC AGC TTT CGT TGT T    (SEQ ID NO: 94)
```

This plasmid was used as a template for construction of cDNA coding mutant LCE using point mutagenesis by PCR. The method for point mutagenesis was as follows. First, the 5'-end portion for mutated LCE cDNA was constructed by PCR using hLCE-F4 as a forward primer and different mutagenic primers as a reverse primer. The 3'-end portion of the LCE cDNA was then constructed by PCR using hLCE- 510S as a forward primer and T7 as a reverse primer. A combination of each mutated LCE cDNA 5'-end fragment and the LCE cDNA 3'-end fragment was used as template for PCR using hLCE-F4 as a forward primer and T7 as a reverse primer, to give DNA fragments containing the full-length coding region of the mutated LCE.

The sequences of the primers used were as follows.

```
hLCE-F4:
AAC ATG TCA GTG TTG ACT TTA C         (SEQ ID NO: 95)

hLCE-510S:
GTG CTC TTC GAA CTG GTG CT            (SEQ ID NO: 96)

T7:
TAA TAC GAC TCA CTA TAG GG            (SEQ ID NO: 97)
```

The constructed LCE mutants were as follows. The mutations introduced into human LCE were: substitution of cysteine (99) by alanine (C99A), substitution of cysteine (225) by alanine (C225A), substitution of histidine (141) by alanine (H141A), substitution of histidine (144) by alanine (H144A), substitution of histidine (145) by alanine (H145A) and substitution of histidine (174) by alanine (H147A).

The sequences of the primers used for the mutagenesis were as follows.

```
C99A:
CCC TGG TCG GCA ACT GAC TGC TTC       (SEQ ID NO: 98)

C225A:
GTG AGA GTG GGC CTG GTC ATG CTG       (SEQ ID NO: 99)

H141A:
GTG ATA CCA GGC CAG GAA GAT C         (SEQ ID NO: 100)

H144A:
GTG ATG TGG GCA TAC CAG TGC           (SEQ ID NO: 101)

H145A:
CAC AGT GAT GGC GTG ATA CCA G         (SEQ ID NO: 102)

H174A:
CAT CAC GGC GGC CAC GCC ATA G         (SEQ ID NO: 103)
```

The obtained mutant LCE cDNA fragments were subcloned into plasmid pCMV-Tag2B using restriction endonucleases EcoRI and XhoI to construct mutant LCE-expressing constructs. The constructs were transfected into HEK293 cells using Lipofectamine 2000 (Invitrogen) for expression of the mutant LCE. Two days after transfection, the cells were harvested, the microsome fraction was prepared and the LCE activity in the microsomes was assayed. The LCE activity assay was carried out by the same method as described in Example 6.

Figure 22:
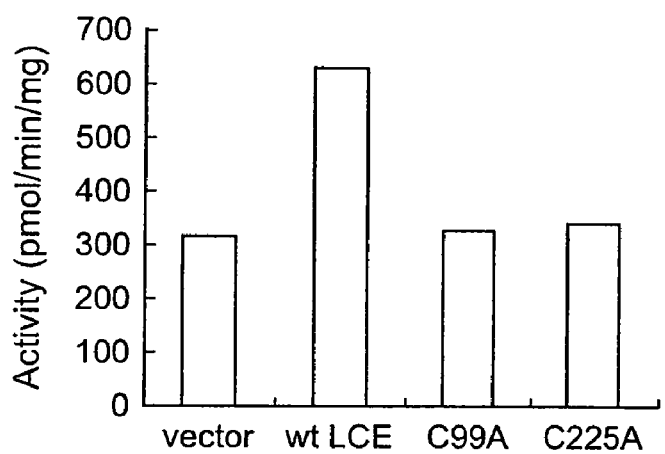
FIG. 22 is a pair of graphs showing LCE activity of LCE mutants, where (a) shows the LCE activity of a mutant wherein cysteine is substituted with alanine and (b) shows the LCE activity of a mutant wherein histidine is substituted with alanine.
Figure 22:
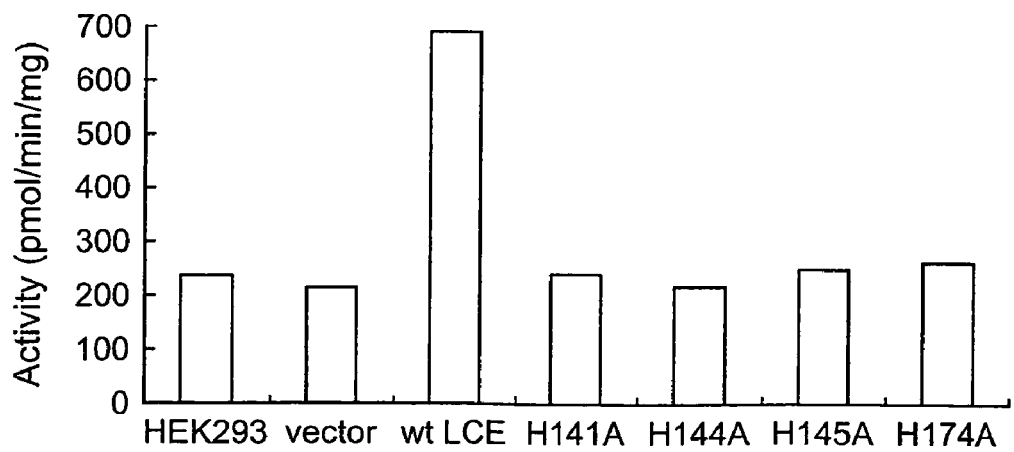

FIG. 22 is a pair of graphs showing LCE activity of LCE mutants. (a) shows LCE activity of a mutant where cysteine is substituted with alanine and (b) shows LCE activity of a mutant where histidine is substituted with alanine. All of the mutants had LCE activity reduction to below half of that of the wild type.

INDUSTRIAL APPLICABILITY

According to the present invention, it is possible to provide a method for treatment and prevention of metabolic disorders, circulatory diseases, central nervous system disorders and the like using substances having activity of inhibiting long chain fatty acid elongase activity (for example, siRNA, low molecular compounds, proteins, antibodies and the like), as well as therapeutic and preventing agents comprising such substances. As examples of metabolic disorders there may be mentioned obesity, diabetes, hormone secretion imbalances, hyperlipidemia, gout and fatty liver. As examples of circulatory diseases there may be mentioned angina, acute and congestive heart failure, myocardial infarction, coronary sclerosis, hypertension, kidney disease and electrolyte imbalances. As an example of a nervous system disorder there may be mentioned bulimia.

The invention claimed is:

1. A method of evaluating compounds which are effective for treatment or prevention of obesity comprising:
   (a) a step in which a test compound is contacted with a long chain fatty acyl elongase (LCE) protein in an admixture comprising a cell-extracted microsome fraction, NADPH, palmitoyl CoA, and labeled malonyl-CoA and
   (b) a step in which it is confirmed whether or not said test compound inhibits the elongase activity of said LCE protein.

2. The method of claim 1 wherein at least 20% of the LCE activity is confirmed as being inhibited.

3. A method of evaluating compounds which are effective for treatment or prevention of obesity comprising:
   (a) a step in which test compounds are contacted with a plurality of elongase proteins including a long chain fatty acyl elongase (LCE) in an admixture comprising a cell-extracted microsome fraction, NADPH, palmitoyl CoA, and labeled malonyl-CoA,
   (b) a step in which the activities of said plurality of elongase proteins are assayed, and
   (c) a step in which test compounds which inhibit the LCE activity among said plurality of elongase proteins are selected as being effective for the treatment or prevention of obesity.

4. The method of claim 3 wherein the test compounds which inhibit at least 20% of the activity of LCE activity are selected.

* * * * *

SEQUENCE LISTING

<160> NUMBER OF SEQ ID NOS: 110

<210> SEQ ID NO 1
<211> LENGTH: 3045
<212> TYPE: DNA
<213> ORGANISM: Homo sapiens

<400> SEQUENCE: 1

| | | | | | |
|---|---|---|---|---|---|
| actaagaccg | caaggcattc | atttcctcct | acggtggatg | cggacgccgg | gaggaggaga | 60 |
| gccccagaga | gaggagctgg | gagcggaggc | gcaggcaatg | ctcagccctg | gatgtagctg | 120 |
| agaggctggg | agaagagacg | accgctggag | accgagcggc | gtggggaaga | cctaggggg | 180 |
| tgggtggggg | aagcagacag | gagaacactc | gaaatcaagc | gctttacaga | ttattttatt | 240 |
| ttgtatagag | aacacgtagc | gactccgaag | atcagcccca | atgaacatgt | cagtgttgac | 300 |
| tttacaagaa | tatgaattcg | aaaagcagtt | caacgagaat | gaagccatcc | aatggatgca | 360 |
| ggaaaactgg | aagaaatctt | tcctgttttc | tgctctgtat | gctgcctta | tattcggtgg | 420 |
| tcggcaccta | atgaataaac | gagcaaagtt | tgaactgagg | aagccattag | tgctctggtc | 480 |
| tctgacccct | gcagtcttca | gtatattcgg | tgctcttcga | actggtgctt | atatggtgta | 540 |

-continued

| | |
|---|---|
| cattttgatg accaaaggcc tgaagcagtc agtttgtgac cagggttttt acaatggacc | 600 |
| tgtcagcaaa ttctgggctt atgcatttgt gctaagcaaa gcacccgaac taggagatac | 660 |
| aatattcatt attctgagga agcagaagct gatcttcctg cactggtatc accacatcac | 720 |
| tgtgctcctg tactcttggt actcctacaa agacatggtt gccggggag gttggttcat | 780 |
| gactatgaac tatggcgtgc acgccgtgat gtactcttac tatgccttgc gggcggcagg | 840 |
| tttccgagtc tcccggaagt tgccatgtt catcaccttg tcccagatca ctcagatgct | 900 |
| gatgggctgt gtggttaact acctggtctt ctgctggatg cagcatgacc agtgtcactc | 960 |
| tcactttcag aacatcttct ggtcctcact catgtacctc agctaccttg tgctcttctg | 1020 |
| ccatttcttc tttgaggcct acatcggcaa atgaggaaa caacgaaag ctgaatagtg | 1080 |
| ttggaactga ggaggaagcc atagctcagg gtcatcaaga aaataatag acaaaagaaa | 1140 |
| atggcacaag gaatcacacg tggtgcagct aaaacaaaac aaaacatgag caaacacaaa | 1200 |
| acccaaggca gcttagggat aattaggttg atttaaccca gtaagtttat gatcctttta | 1260 |
| gggtgaggac tcactgagtg cacctccatc tccaagcact gctgctggaa gaccccattc | 1320 |
| cctctttatc tatcaactct aggacaaggg agaacaaaag caagccagaa gcagaggaga | 1380 |
| ctaatcaaag gcaaacaaag gctattaaca cataggaaaa tatgtattta ctaagtgtca | 1440 |
| catttctcta agatgaaaga ttttactct agaaactgtg cgagcacaac acacacaatc | 1500 |
| ctttctaact ttatggacac taaactggag ccaatagaaa agacaaaaat gaaagagaca | 1560 |
| cagggtgtat atctagaacg ataatgcttt tgcagaaact aaagccttt taagaaatgc | 1620 |
| cagctgctgt agaccccatg agaaaagatg tcttaatcat ccttatgaaa acagatgtaa | 1680 |
| acaactatat ttcaactaac ttcatcttca ctgcatagcc tcaggctagt gagtttgcca | 1740 |
| aaaccaaagg gggtgaatac ttccccaaga ttcttcctgg gaggatggaa acagtgcagc | 1800 |
| ccaggtccca tgggggcagc tccatcccag agcatttctg atagttgaac tgtaatttct | 1860 |
| actcttaagt gagatatgaa gtattatcct tttgttcagt tgccccgggc ttttgaacag | 1920 |
| aagagtaaat acagaattga aaagataaa cactcaacca aacaatgtga aaacgggttc | 1980 |
| tgtagtattt gtaaaaggc ccggcccagg accactgtga gctggaaaag ggagaaaggc | 2040 |
| agtgggaaaa gaggtgagcc gaagatcaat tcgacagaca gacggtgtgt atgcccctcc | 2100 |
| ctgtttgact tcacacacac tcataacttt ccaaatgaaa ccccacagta tagcgcatat | 2160 |
| tttcgatatt tttgtgaatt ccaaaaggaa atcacagggc tgttcgaaat attgggggaa | 2220 |
| cactgtgttt ctgcatcatc tgcatttgct ccccaagcaa tgtagaggtg tttaagggc | 2280 |
| cctctgctgg ctgagtggca atactacaac aaacttcaag gcaagtttgg ctgaaaacag | 2340 |
| ttgacaacaa agggccccca tacacttatc cctcaaattt taagtgatat gaaatacttg | 2400 |
| tcatgtcttt ggccaaatca gaagatattc atcctgcttc aagtcagctt cagaaatgtt | 2460 |
| ttaaaaggga ctttagctct ggaactcaaa atcaatttat taagagccat attctttaaa | 2520 |
| aaaaaaagct ggataatatt atctgtaata tttcagtcct ttacaagcca aatacatgtg | 2580 |
| tcaatgtttc tagtatttca aagaagcaat tatgtaaagt tgttcaatgt gacataatag | 2640 |
| tattataatt ggttaagtag cttaatgatt aggcaaacta gatgaaaaga ttaggggctt | 2700 |
| ccacactgca tagatcacac gcacatagcc acgcatacac acacagacac acagatgtgg | 2760 |
| ggtacactga atttcaaagc ccaaatgaat agaaacacat tttctggcta gcagaaaaaa | 2820 |
| acaaaacaaa actgttgttt ctctttcttg ctttgagagt gtacagtaaa agggattttt | 2880 |

-continued

| | |
|---|---|
| tcgaattatt tttatattat tttagcttta attgtgctgt cgttcatgaa acagagctgc | 2940 |
| tctgcttttc tgtcagagat ggcaagggct ttttcagcat ctcgtttatg tgtggaattt | 3000 |
| aaaaagaata aagttttatt ccattctgaa aaaaaaaaaa aaaaa | 3045 |

<210> SEQ ID NO 2
<211> LENGTH: 5893
<212> TYPE: DNA
<213> ORGANISM: Homo sapiens

<400> SEQUENCE: 2

| | |
|---|---|
| tggatgcgga cgctgggagg agagccctg agctaggagc tgggagcaga ggcgcagaga | 60 |
| acacgtagcg actccgaaga tcagcccaa tgaacatgtc agtgttgact ttacaagaat | 120 |
| atgaattcga aaagcagttc aacgagaacg aagccatcca atggatgcag gaaaactgga | 180 |
| agaagtcttt cctgtttttct gcgctgtacg ctgcctttat ctttggtggt cggcatctga | 240 |
| tgaacaagcg agccaagttt gaacttcgga agccgctcgt gctctggtcg ctgactcttg | 300 |
| ccgtcttcag tatattcggt gctcttcgaa ctggtgctta catgctgtac attctgatga | 360 |
| ccaaaggcct gaagcagtca gtttgtgacc agagttttta caatggacct gtcagcaaat | 420 |
| tctgggctta tgcatttgtg ctcagcaaag cacccgaact aggtgacacg atattcatca | 480 |
| ttctgaggaa acagaaactg atcttcctgc actggtacca ccacatcact gtgctcctgt | 540 |
| actcctggta ctcctacaaa gacatggtcg ctggggtgg ttggttcatg actatgaact | 600 |
| atggcgtgca tgccgtcatg tactcttact acgccttgcg ggctgcgggt ttccgagtct | 660 |
| cccggaagtt tgccatgttc atcaccttgt cccagatcac tcagatgctg atgggctgtg | 720 |
| tcattaacta cctggtcttc aactggatgc agcatgacaa cgaccagtgc tactcccact | 780 |
| ttcagaacat cttctggtcc tcgctcatgt acctcagcta ccttgtgctc ttctgccatt | 840 |
| tcttctttga ggcctacatc ggcaaagtga agaaagccac gaaggctgag tagtgtcagg | 900 |
| gctgaggagg aagtcatagc tcagggtcat cacgaaaaat aatcgacaaa agaaaaatgg | 960 |
| cacaaggaat cccatatggt gcagctaaaa caaaacaaaa catccgtatg agcaggcacg | 1020 |
| aggcccaagg cagcttggga ctgaagatta ggttgtaagt ttatgatcct ttctgggtga | 1080 |
| ggactcgctg agtgcaactc ttatctcaaa gcacggctgc tgagggggacc ccttccctct | 1140 |
| ggcctgtcaa ctctagaaca cactagatgc aaaggcagcc acgggcaaag agattgggca | 1200 |
| gagattagtg gacggccagc aaaacactgc aggaagcagg tgggggagg aatctactca | 1260 |
| gccttttttgt tttgttttgt tttgttttgt tttgtttttc tctaaggata aaggagtttc | 1320 |
| cccttttcaa acgatgtgag cacacacaca cacacacaca cacacacaca cacacacaca | 1380 |
| cacacgcaat cttttcaaca cgaaaccaga gctaaaagaa aagataaaca tgggagagac | 1440 |
| agggtttcta tctgggacag caatgctttt gcaaaaggct aggccttttta aagaaaggtg | 1500 |
| agcttgtaac tccttgataa agatgtgtctt aattatttttt actgcaactg aaagtaaaga | 1560 |
| ggtagagcct ttccccttct gcacagcctc agggcttgta tgttcgctac aaccaaacac | 1620 |
| aggacagtac ttcccccatg atactttatt actgggagaa agaaacccct gtagttgaaa | 1680 |
| caccacactg acaactgtta tttctgctct ccgacgagaa ttcaagcatc cgttgttcag | 1740 |
| ttgccccaaa ctttagtgac ggaggagtaa atgcagaact gaaagggaag aagctcagct | 1800 |
| ggctggcttg aaaatggagt cttgtaccat gtgtaacaaa tgccagccca tcgtccctgg | 1860 |
| agctgaacag ggaggaaggg ctatgggcag agactagagc cggattcatc caatgtgcag | 1920 |
| acagcgtgtt cgcctccctc cctgttcgac ctcacacata atcctggctt tctaaatgag | 1980 |

```
gccctgtgac acactctgtg ctttctatat ttttgtgact ttcaaacaca gatctgcagg    2040
gctctgcctg atttggggta aacactgtgt ttctgcagcc tctgcatttg ctcccttcag    2100
cagtgcagag gcttgagaag tgccctctgc tggcttagtg agaagcttca acaaacactt    2160
cacagtagtg ttgaaataac tgaccactaa gggcctgcgg agattaaacc ctaagttcta    2220
agtgctgtca acacctgac atatatttga ccaaatcaga aattttttag gtgactttca     2280
cttgagaact cagaaagtca atgtattaag agccatattc tgaaagaaag aaagagaaag    2340
agagaaagaa agaaagaaag aaagaaagaa agaaagaaag aaagaaagaa agaagaaaga    2400
aagaaagaaa gaaagcaagc tagacaatgt taactgtaat atttcagtcc tctacaagcc    2460
aaataaatgt gtcgatgttc ctaatatttc aaagacgcaa ttacataaag ttgttcaatg    2520
tgatataata gtattctaat tggttaagta gtttaatgat taggcaaact agcagaaaca    2580
attagaggct gctacaccac gtagattata cacacatagc cacgtacgtg aggtacacgg    2640
agctataaag ctcaaatcaa tagtaacacg attttttggct agcagaaact atcacctatc    2700
ttcctttact tgagagtgta cagtaaaagg gattttttc aaattatttt tatattattt      2760
tagctttaat tgtgctgtca ttcatggaac agctgctcag cagccttcct gtgagagatg    2820
acaggggtgt tttcgtgtgg cttgtttacg tgtggaattg gaaaagaata aaatctgatt    2880
cccttctgtg ggaatgggat caagggtaga caaaggaccc atgtagatca agtcataact    2940
gaacgaccag ggaagggagc caggcggggg cgggagtcag ctgtggcttt catgttacca    3000
ttgtgtggtg gctgatggac gggacgtggt tggagggatg ttttcttact tggggtagaa    3060
gctaaccgga gatgaaagtc tagaagccac tctgtccagt ggaatcttag ggtgtacttg    3120
ttcctttgag ctttgtaaat gcacaatagt gtacaataat aagcctttcc cttgccttat    3180
ggaagaaagt gagcaagata atgaaaacca agaagccacc tatcagttga attgagtcta    3240
atcaaaaggc cagcctgagg ctcctctggt cggttcagtt taatttagat atttaccata    3300
gaatacaggt acaatatgga aatctcataa gcataaactt taaaacgact aagctatgct    3360
tccaaagcac tttagtctca gtgttcttcg cttcatgctc tctccacttg taaaataact    3420
tagacttttc attcgcagga tgagtatata ataattaagt ttccaaacca gctaaactgt    3480
agctacaggc aattccagtg ttcaccatgg aagaaaaag ccacatgtttt ttttaaaaac    3540 acagaattct gatataggct cagcacacag ttttaacat atcagcttag ctgctctaat    3600
tgtatcaaga tacgaggctg gaccactggc ctatgacaca tctaaaacct gccagaattg    3660
actgccacgt agataatact gctgtcagtg aacattccgg gcaagcaagt ttttgtagct    3720
gccccactat gctgcaatag attatctttc tattgaagat ttctcgctgc attccaatcc    3780
cagtgtggtg aaaacttaat tcctggattg aatgaacaca aatccgaggt ttcatataaa    3840
cgcagtgcgg tcactaggtc tgagcatcaa ctcaaatgtg ttgagtttgc aatgaaattc    3900
tagtgagaat cactccattc acacagtagg agatttttat ctggaccttc tagtgtcaac    3960
tgtgaggaga acaactatc attattattt atttattgta tttatatcca atgccaggcc     4020
aaagtattga tttagatcaa gcagtgccct tccccccct cccaaccccc catctttcta     4080
atccttctgc actatagaaa gtcaagactg gaggggaaat ccatattcat tgctgcaggg    4140
gaaagcaggt ttattaatcc tcccgctgtc tttatgagac cgattgacca atgtagctca    4200
ggcagaagtt tcatgtgggt gggatatcta caggagccta ggaaaacact tccagagaag    4260
ataaccacag actgttgttt ttgttcattt gttttatatc ttcatggtaa gataagcctg    4320
```

-continued

```
tcacggagtt acaaggcacc atgacactaa ggtagaatgt tccagaagtc tggctacctt    4380
cccaggctgc tcagttacct gggagtgtct agttactatc ttgttctgac gagaggagct    4440
tttgctcaag aactgccaga tacagacacc aagtcagccc tggcacactc tacaacctcc    4500
gggcataggt aatgggtctt tgactattgg attgcctcag tgtcaagtga gttcctagaa    4560
gaagagaccg agtaggctct acccccagga ctccaccaca ctctgagttg cattgacagg    4620
atcggtgtct agacacagtt ctttgtgaag tgtcaatgct agagacagtt gtgaggagat    4680
catgatgaca gcccagaact ttctagcttt caaatgcatc cttttccagt ctttgttttg    4740
ataacagcta ttttgctatc agtttgggac aacagtagag tctgtggcca tgtgatctac    4800
agcttatgat cacacagctc ccatttcctg gtgcctgaga tcccagccat cagaaagtga    4860
tttgggtgag aattcacaac atatatgtca cctctgcata ttgaagtgac atctaataaa    4920
acaaggacgt cctatttttgt ctgaacccgc tgaatgaagc tctgttatcc tagttagtca    4980
ttgggccgcc atcctctgta cccgatagtac acacaaaaca gatgtcggtg cctgtacaag    5040
aattctcagt gcctgttgtg acagactgtg cttagaagaa acattcgtga gccataaagc    5100
aggaaccaca gatgaaaggg ccagttaaaa gtccacctgc tccaagtatc atagaaaacc    5160
caaaagcctg ttgtataatc tggtattgtc cccatcccca gatgctttga aaactaggat    5220
tctcagagca tggataccca cgcttccatc ttcccacaaa catttcctag agttgtactg    5280
gtgggtgcag ccctaggtgg ttggttgggg gaagtcttgg aagctgtact ttgattgcag    5340
gtcaagcaaa gccaaatcca gatatttctg tgtcactcac cagttgtcca tgtccaccca    5400
caaaacaatt gtattatagt caagttgtcc tagctgattg gtcctcaaat aaggatgcaa    5460
ctatgtttgc aacccagtta ggacacattt gaaagaacct gactcactag catctaaaca    5520
atatcatttc cccaatgctt ggtggcactt cagacttttg ttctcctggt tgatcaaggt    5580
gttgcctggt ggtgccgcct cctagtgtga atatttcagt taagtgtggg tctgagcatg    5640
accgggctgg gcttagctca ctgctacttg gaaaatgact ggcattctgc ttcctaggcc    5700
ctaaacccat attcagaggg aaaattcact atcaagcctc acagcgaaat cacagcagtg    5760
ttggaattct tattttcaag tgcttatctc acaacattga aaaatatttt tggtgtatta    5820
agatttaaaa taaagtcatc ataaactttt gaatttaaaa aaaaaaaaa aaaaaaaaa    5880 aaaaaaaaaa aaa                                                         5893
```

```
<210> SEQ ID NO 3
<211> LENGTH: 34
<212> TYPE: DNA
<213> ORGANISM: Artificial
<220> FEATURE:
<223> OTHER INFORMATION: PCR primer

<400> SEQUENCE: 3
gccaccatgg gcaacatgtc agtgttgact ttac                                   34

<210> SEQ ID NO 4
<211> LENGTH: 24
<212> TYPE: DNA
<213> ORGANISM: Artificial
<220> FEATURE:
<223> OTHER INFORMATION: PCR primer

<400> SEQUENCE: 4
ctactcagcc ttcgtggctt tctt                                              24
```

```
<210> SEQ ID NO 5
<211> LENGTH: 27
<212> TYPE: DNA
<213> ORGANISM: Artificial
<220> FEATURE:
<223> OTHER INFORMATION: probe

<400> SEQUENCE: 5
ctttcctgtt ttctgcgctg tacgctg                                        27

<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
ggatgcagga aaactggaag aa                                             22

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
tgccgaccac caaagataaa g                                              21

<210> SEQ ID NO 8
<211> LENGTH: 19
<212> TYPE: DNA
<213> ORGANISM: Artificial
<220> FEATURE:
<223> OTHER INFORMATION: probe

<400> SEQUENCE: 8
atcactgtgc tcctgtact                                                 19

<210> SEQ ID NO 9
<211> LENGTH: 23
<212> TYPE: DNA
<213> ORGANISM: Artificial
<220> FEATURE:
<223> OTHER INFORMATION: PCR primer

<400> SEQUENCE: 9
agctgatctt cctgcactgg tat                                            23

<210> SEQ ID NO 10
<211> LENGTH: 24
<212> TYPE: DNA
<213> ORGANISM: Artificial
<220> FEATURE:
<223> OTHER INFORMATION: PCR primer

<400> SEQUENCE: 10
ggcaaccatg tctttgtagg agta                                           24

<210> SEQ ID NO 11
<211> LENGTH: 34
<212> TYPE: DNA
<213> ORGANISM: Artificial
<220> FEATURE:
<223> OTHER INFORMATION: PCR primer
```

```
<400> SEQUENCE: 11
gccaccatgg gcaacatgtc agtgttgact ttac                          34

<210> SEQ ID NO 12
<211> LENGTH: 25
<212> TYPE: DNA
<213> ORGANISM: Artificial
<220> FEATURE:
<223> OTHER INFORMATION: PCR primer

<400> SEQUENCE: 12
ctattcagct ttcgttgttt tcctc                                    25

<210> SEQ ID NO 13
<211> LENGTH: 21
<212> TYPE: RNA
<213> ORGANISM: Artificial
<220> FEATURE:
<223> OTHER INFORMATION: sense strand of hLCE-siRNA-1

<400> SEQUENCE: 13
gaccgcaagg cauucauuuu u                                        21

<210> SEQ ID NO 14
<211> LENGTH: 21
<212> TYPE: RNA
<213> ORGANISM: Artificial
<220> FEATURE:
<223> OTHER INFORMATION: antisense strand of hLCE-siRNA-1

<400> SEQUENCE: 14
uucuggcguu ccguaaguaa a                                        21

<210> SEQ ID NO 15
<211> LENGTH: 21
<212> TYPE: RNA
<213> ORGANISM: Artificial
<220> FEATURE:
<223> OTHER INFORMATION: sense strand of hLCE-siRNA-2

<400> SEQUENCE: 15
cacucgaaau caagcgcuuu u                                        21

<210> SEQ ID NO 16
<211> LENGTH: 21
<212> TYPE: RNA
<213> ORGANISM: Artificial
<220> FEATURE:
<223> OTHER INFORMATION: antisense strand of hLCE-siRNA-2

<400> SEQUENCE: 16
uugugagcuu uaguucgcga a                                        21

<210> SEQ ID NO 17
<211> LENGTH: 21
<212> TYPE: RNA
<213> ORGANISM: Artificial
<220> FEATURE:
<223> OTHER INFORMATION: sense strand of hLCE-siRNA-3

<400> SEQUENCE: 17
cacguagcga cuccgaagau u                                        21

<210> SEQ ID NO 18
<211> LENGTH: 21
```

```
<212> TYPE: RNA
<213> ORGANISM: Artificial
<220> FEATURE:
<223> OTHER INFORMATION: antisense strand of hLCE-siRNA-3

<400> SEQUENCE: 18
uugugcaucg cugaggcuuc u                                              21

<210> SEQ ID NO 19
<211> LENGTH: 21
<212> TYPE: RNA
<213> ORGANISM: Artificial
<220> FEATURE:
<223> OTHER INFORMATION: sense strand of hLCE-siRNA-4

<400> SEQUENCE: 19
ugaagccauc caauggaugu u                                              21

<210> SEQ ID NO 20
<211> LENGTH: 21
<212> TYPE: RNA
<213> ORGANISM: Artificial
<220> FEATURE:
<223> OTHER INFORMATION: antisense strand of hLCE-siRNA-4

<400> SEQUENCE: 20
uuacuucggu agguuaccua c                                              21

<210> SEQ ID NO 21
<211> LENGTH: 21
<212> TYPE: RNA
<213> ORGANISM: Artificial
<220> FEATURE:
<223> OTHER INFORMATION: sense strand of hLCE-siRNA-5

<400> SEQUENCE: 21
gccauuagug cucuggucuu u                                              21

<210> SEQ ID NO 22
<211> LENGTH: 21
<212> TYPE: RNA
<213> ORGANISM: Artificial
<220> FEATURE:
<223> OTHER INFORMATION: antisense strand of hLCE-siRNA-5

<400> SEQUENCE: 22
uucgguaauc acgagaccag a                                              21

<210> SEQ ID NO 23
<211> LENGTH: 21
<212> TYPE: RNA
<213> ORGANISM: Artificial
<220> FEATURE:
<223> OTHER INFORMATION: sense strand of hLCE-siRNA-6

<400> SEQUENCE: 23
aggccugaag cagucaguuu u                                              21

<210> SEQ ID NO 24
<211> LENGTH: 21
<212> TYPE: RNA
<213> ORGANISM: Artificial
<220> FEATURE:
<223> OTHER INFORMATION: antisense strand of hLCE-siRNA-6

<400> SEQUENCE: 24
```
uuuccggacu ucgucaguca a          21

<210> SEQ ID NO 25
<211> LENGTH: 21
<212> TYPE: RNA
<213> ORGANISM: Artificial
<220> FEATURE:
<223> OTHER INFORMATION: sense strand of LCE-siRNA-2

<400> SEQUENCE: 25
uggaccuguc agcaaauucu u          21

<210> SEQ ID NO 26
<211> LENGTH: 21
<212> TYPE: RNA
<213> ORGANISM: Artificial
<220> FEATURE:
<223> OTHER INFORMATION: antisense strand of LCE-siRNA-2

<400> SEQUENCE: 26
uuaccuggac agucguuuaa g          21

<210> SEQ ID NO 27
<211> LENGTH: 21
<212> TYPE: RNA
<213> ORGANISM: Artificial
<220> FEATURE:
<223> OTHER INFORMATION: sense strand of hLCE-siRNA-7

<400> SEQUENCE: 27
agcacccgaa cuaggagauu u          21

<210> SEQ ID NO 28
<211> LENGTH: 21
<212> TYPE: RNA
<213> ORGANISM: Artificial
<220> FEATURE:
<223> OTHER INFORMATION: antisense strand of hLCE-siRNA-7

<400> SEQUENCE: 28
uuucgugggc uugauccucu a          21

<210> SEQ ID NO 29
<211> LENGTH: 21
<212> TYPE: RNA
<213> ORGANISM: Artificial
<220> FEATURE:
<223> OTHER INFORMATION: sense strand of hLCE-siRNA-8

<400> SEQUENCE: 29
caucuucugg uccucacucu u          21

<210> SEQ ID NO 30
<211> LENGTH: 21
<212> TYPE: RNA
<213> ORGANISM: Artificial
<220> FEATURE:
<223> OTHER INFORMATION: antisense strand of hLCE-siRNA-8

<400> SEQUENCE: 30
uuguagaaga ccaggaguga g          21

<210> SEQ ID NO 31
<211> LENGTH: 21
<212> TYPE: RNA
<213> ORGANISM: Artificial

```
<220> FEATURE:
<223> OTHER INFORMATION: sense strand of hLCE-siRNA-9

<400> SEQUENCE: 31
ucacacgugg ugcagcuaau u                                              21

<210> SEQ ID NO 32
<211> LENGTH: 21
<212> TYPE: RNA
<213> ORGANISM: Artificial
<220> FEATURE:
<223> OTHER INFORMATION: antisense strand of hLCE-siRNA-9

<400> SEQUENCE: 32
uuagugugca ccacgucgau u                                              21

<210> SEQ ID NO 33
<211> LENGTH: 21
<212> TYPE: RNA
<213> ORGANISM: Artificial
<220> FEATURE:
<223> OTHER INFORMATION: sense strand of hLCE-siRNA-10

<400> SEQUENCE: 33
gcacugcugc uggaagaccu u                                              21

<210> SEQ ID NO 34
<211> LENGTH: 21
<212> TYPE: RNA
<213> ORGANISM: Artificial
<220> FEATURE:
<223> OTHER INFORMATION: antisense strand of hLCE-siRNA-10

<400> SEQUENCE: 34
uucgugacga cgaccuucug g                                              21

<210> SEQ ID NO 35
<211> LENGTH: 21
<212> TYPE: RNA
<213> ORGANISM: Artificial
<220> FEATURE:
<223> OTHER INFORMATION: sense strand of hLCE-siRNA-11

<400> SEQUENCE: 35
acugugcgag cacaacacau u                                              21

<210> SEQ ID NO 36
<211> LENGTH: 21
<212> TYPE: RNA
<213> ORGANISM: Artificial
<220> FEATURE:
<223> OTHER INFORMATION: antisense strand of hLCE-siRNA-11

<400> SEQUENCE: 36
uuugacacgc ucguguugug u                                              21

<210> SEQ ID NO 37
<211> LENGTH: 21
<212> TYPE: RNA
<213> ORGANISM: Artificial
<220> FEATURE:
<223> OTHER INFORMATION: sense strand of hLCE-siRNA-12

<400> SEQUENCE: 37 aggggguga auacuucccu u                                               21
```

<210> SEQ ID NO 38
<211> LENGTH: 21
<212> TYPE: RNA
<213> ORGANISM: Artificial
<220> FEATURE:
<223> OTHER INFORMATION: antisense strand of hLCE-siRNA-12

<400> SEQUENCE: 38 uuuccccac uuaugaaggg g                                              21

<210> SEQ ID NO 39
<211> LENGTH: 22
<212> TYPE: DNA
<213> ORGANISM: Artificial
<220> FEATURE:
<223> OTHER INFORMATION: probe

<400> SEQUENCE: 39
acccgctcgg catggctatc tt                                            22

<210> SEQ ID NO 40
<211> LENGTH: 23
<212> TYPE: DNA
<213> ORGANISM: Artificial
<220> FEATURE:
<223> OTHER INFORMATION: PCR primer

<400> SEQUENCE: 40
gcaaattcga cctttctcag aac                                           23

<210> SEQ ID NO 41
<211> LENGTH: 18
<212> TYPE: DNA
<213> ORGANISM: Artificial
<220> FEATURE:
<223> OTHER INFORMATION: PCR primer

<400> SEQUENCE: 41
ggaccccgtg gaatgtca                                                 18

<210> SEQ ID NO 42
<211> LENGTH: 20
<212> TYPE: DNA
<213> ORGANISM: Artificial
<220> FEATURE:
<223> OTHER INFORMATION: PCR primer

<400> SEQUENCE: 42
tacgcctccc tcaacttccg                                               20

<210> SEQ ID NO 43
<211> LENGTH: 20
<212> TYPE: DNA
<213> ORGANISM: Artificial
<220> FEATURE:
<223> OTHER INFORMATION: PCR primer

<400> SEQUENCE: 43
cacttgaggg gccgtaccac                                               20

<210> SEQ ID NO 44
<211> LENGTH: 28
<212> TYPE: DNA
<213> ORGANISM: Artificial
<220> FEATURE:
<223> OTHER INFORMATION: probe

```
<400> SEQUENCE: 44
cacatgctga tcctcataat tcccgacg                                      28

<210> SEQ ID NO 45
<211> LENGTH: 21
<212> TYPE: DNA
<213> ORGANISM: Artificial
<220> FEATURE:
<223> OTHER INFORMATION: PCR primer

<400> SEQUENCE: 45
gcccaccaca agttttcaga a                                             21

<210> SEQ ID NO 46
<211> LENGTH: 22
<212> TYPE: DNA
<213> ORGANISM: Artificial
<220> FEATURE:
<223> OTHER INFORMATION: PCR primer

<400> SEQUENCE: 46
ccacgtgaga gaagaaaaag cc                                            22

<210> SEQ ID NO 47
<211> LENGTH: 20
<212> TYPE: DNA
<213> ORGANISM: Artificial
<220> FEATURE:
<223> OTHER INFORMATION: PCR primer

<400> SEQUENCE: 47
tgtggagcca ccgctcttac                                               20

<210> SEQ ID NO 48
<211> LENGTH: 20
<212> TYPE: DNA
<213> ORGANISM: Artificial
<220> FEATURE:
<223> OTHER INFORMATION: PCR primer

<400> SEQUENCE: 48
aagcgtgggc aggatgaagc                                               20

<210> SEQ ID NO 49
<211> LENGTH: 21
<212> TYPE: RNA
<213> ORGANISM: Artificial
<220> FEATURE:
<223> OTHER INFORMATION: sense strand of hLCE-siRNA-6

<400> SEQUENCE: 49
aggccugaag cagucaguuu u                                             21

<210> SEQ ID NO 50
<211> LENGTH: 21
<212> TYPE: RNA
<213> ORGANISM: Artificial
<220> FEATURE:
<223> OTHER INFORMATION: antisense strand of hLCE-siRNA-6

<400> SEQUENCE: 50
uuuccggacu ucgucaguca a                                             21

<210> SEQ ID NO 51
```

-continued

```
<211> LENGTH: 21
<212> TYPE: RNA
<213> ORGANISM: Artificial
<220> FEATURE:
<223> OTHER INFORMATION: sense strand of mLCE-siRNA-7

<400> SEQUENCE: 51
ucccauaugg ugcagcuaau u                                      21

<210> SEQ ID NO 52
<211> LENGTH: 21
<212> TYPE: RNA
<213> ORGANISM: Artificial
<220> FEATURE:
<223> OTHER INFORMATION: antisense strand of mLCE-siRNA-7

<400> SEQUENCE: 52
uuaggguaua ccacgucgau u                                      21

<210> SEQ ID NO 53
<211> LENGTH: 21
<212> TYPE: RNA
<213> ORGANISM: Artificial
<220> FEATURE:
<223> OTHER INFORMATION: sense strand of mLCE-siRNA-11

<400> SEQUENCE: 53
gcauccguug uucaguugcu u                                      21

<210> SEQ ID NO 54
<211> LENGTH: 21
<212> TYPE: RNA
<213> ORGANISM: Artificial
<220> FEATURE:
<223> OTHER INFORMATION: antisense strand of mLCE-siRNA-11

<400> SEQUENCE: 54
uucguaggca acaagucaac g                                      21

<210> SEQ ID NO 55
<211> LENGTH: 27
<212> TYPE: DNA
<213> ORGANISM: Artificial
<220> FEATURE:
<223> OTHER INFORMATION: probe

<400> SEQUENCE: 55
atgctggcca aactaactac ggcttcg                                27

<210> SEQ ID NO 56
<211> LENGTH: 22
<212> TYPE: DNA
<213> ORGANISM: Artificial
<220> FEATURE:
<223> OTHER INFORMATION: PCR primer

<400> SEQUENCE: 56
tggccttctc ctctgtaagc tg                                     22

<210> SEQ ID NO 57
<211> LENGTH: 23
<212> TYPE: DNA
<213> ORGANISM: Artificial
<220> FEATURE:
<223> OTHER INFORMATION: PCR primer

<400> SEQUENCE: 57
```

```
ctgttcacat atacgctcca tgg                                          23

<210> SEQ ID NO 58
<211> LENGTH: 20
<212> TYPE: DNA
<213> ORGANISM: Artificial
<220> FEATURE:
<223> OTHER INFORMATION: PCR primer

<400> SEQUENCE: 58
ttccgctaca tggctcaggg                                              20

<210> SEQ ID NO 59
<211> LENGTH: 20
<212> TYPE: DNA
<213> ORGANISM: Artificial
<220> FEATURE:
<223> OTHER INFORMATION: PCR primer

<400> SEQUENCE: 59
cccgtacact cactcgtggc                                              20

<210> SEQ ID NO 60
<211> LENGTH: 24
<212> TYPE: DNA
<213> ORGANISM: Artificial
<220> FEATURE:
<223> OTHER INFORMATION: PCR primer

<400> SEQUENCE: 60
caacacagca accagaaact caag                                         24

<210> SEQ ID NO 61
<211> LENGTH: 21
<212> TYPE: DNA
<213> ORGANISM: Artificial
<220> FEATURE:
<223> OTHER INFORMATION: PCR primer

<400> SEQUENCE: 61
ttgcttttgt ggacagcagt g                                            21

<210> SEQ ID NO 62
<211> LENGTH: 20
<212> TYPE: DNA
<213> ORGANISM: Artificial
<220> FEATURE:
<223> OTHER INFORMATION: PCR primer

<400> SEQUENCE: 62
cggagaagct gcctatcaac                                              20

<210> SEQ ID NO 63
<211> LENGTH: 20
<212> TYPE: DNA
<213> ORGANISM: Artificial
<220> FEATURE:
<223> OTHER INFORMATION: PCR primer

<400> SEQUENCE: 63
ggtcagtgtg tcctccacct                                              20

<210> SEQ ID NO 64
<211> LENGTH: 23
<212> TYPE: DNA
```

<213> ORGANISM: Artificial
<220> FEATURE:
<223> OTHER INFORMATION: PCR primer

<400> SEQUENCE: 64
gatatcgctc ctccatcaat gac                                    23

<210> SEQ ID NO 65
<211> LENGTH: 21
<212> TYPE: DNA
<213> ORGANISM: Artificial
<220> FEATURE:
<223> OTHER INFORMATION: PCR primer

<400> SEQUENCE: 65
acttgtgcat cttggcgtct g                                      21

<210> SEQ ID NO 66
<211> LENGTH: 20
<212> TYPE: DNA
<213> ORGANISM: Artificial
<220> FEATURE:
<223> OTHER INFORMATION: PCR primer

<400> SEQUENCE: 66
cattctgacc acaatgcctg                                        20

<210> SEQ ID NO 67
<211> LENGTH: 20
<212> TYPE: DNA
<213> ORGANISM: Artificial
<220> FEATURE:
<223> OTHER INFORMATION: PCR primer

<400> SEQUENCE: 67
agtagggaga gaagccagcc                                        20

<210> SEQ ID NO 68
<211> LENGTH: 26
<212> TYPE: DNA
<213> ORGANISM: Artificial
<220> FEATURE:
<223> OTHER INFORMATION: probe

<400> SEQUENCE: 68
ccgggaggaa atcaaaccaa ttcgtc                                 26

<210> SEQ ID NO 69
<211> LENGTH: 20
<212> TYPE: DNA
<213> ORGANISM: Artificial
<220> FEATURE:
<223> OTHER INFORMATION: PCR primer

<400> SEQUENCE: 69
tgctttacag gcgcaaactg                                        20

<210> SEQ ID NO 70
<211> LENGTH: 19
<212> TYPE: DNA
<213> ORGANISM: Artificial
<220> FEATURE:
<223> OTHER INFORMATION: PCR primer

<400> SEQUENCE: 70
tggaatcgtg gatcccaaa                                         19

<210> SEQ ID NO 71
<211> LENGTH: 25
<212> TYPE: DNA
<213> ORGANISM: Artificial
<220> FEATURE:
<223> OTHER INFORMATION: PCR primer

<400> SEQUENCE: 71
atttgaagtt aaaatcctgg tgggc                                    25

<210> SEQ ID NO 72
<211> LENGTH: 20
<212> TYPE: DNA
<213> ORGANISM: Artificial
<220> FEATURE:
<223> OTHER INFORMATION: PCR primer

<400> SEQUENCE: 72
ttcccacgtc caaaataggc                                          20

<210> SEQ ID NO 73
<211> LENGTH: 28
<212> TYPE: DNA
<213> ORGANISM: Artificial
<220> FEATURE:
<223> OTHER INFORMATION: probe

<400> SEQUENCE: 73
agctgcaagc ctgtcatcct caatatcg                                 28

<210> SEQ ID NO 74
<211> LENGTH: 25
<212> TYPE: DNA
<213> ORGANISM: Artificial
<220> FEATURE:
<223> OTHER INFORMATION: PCR primer

<400> SEQUENCE: 74
ttctgaatgt ggctatcaag actga                                    25

<210> SEQ ID NO 75
<211> LENGTH: 22
<212> TYPE: DNA
<213> ORGANISM: Artificial
<220> FEATURE:
<223> OTHER INFORMATION: PCR primer

<400> SEQUENCE: 75
tgctgggtga actctctgaa ca                                       22

<210> SEQ ID NO 76
<211> LENGTH: 20
<212> TYPE: DNA
<213> ORGANISM: Artificial
<220> FEATURE:
<223> OTHER INFORMATION: PCR primer

<400> SEQUENCE: 76
tagtgtcagc gatgttctgt                                          20

<210> SEQ ID NO 77
<211> LENGTH: 20
<212> TYPE: DNA
<213> ORGANISM: Artificial
<220> FEATURE:

```
<223> OTHER INFORMATION: PCR primer

<400> SEQUENCE: 77
aaatctctga tccacctcac                                                    20

<210> SEQ ID NO 78
<211> LENGTH: 23
<212> TYPE: DNA
<213> ORGANISM: Artificial
<220> FEATURE:
<223> OTHER INFORMATION: probe

<400> SEQUENCE: 78
actcgcctac accaacgggc tcc                                                23

<210> SEQ ID NO 79
<211> LENGTH: 18
<212> TYPE: DNA
<213> ORGANISM: Artificial
<220> FEATURE:
<223> OTHER INFORMATION: PCR primer

<400> SEQUENCE: 79
tttccaagcg cagttccg                                                      18

<210> SEQ ID NO 80
<211> LENGTH: 19
<212> TYPE: DNA
<213> ORGANISM: Artificial
<220> FEATURE:
<223> OTHER INFORMATION: PCR primer

<400> SEQUENCE: 80
atcgagcgtg gacttcggt                                                     19

<210> SEQ ID NO 81
<211> LENGTH: 20
<212> TYPE: DNA
<213> ORGANISM: Artificial
<220> FEATURE:
<223> OTHER INFORMATION: PCR primer

<400> SEQUENCE: 81
cacccatccc gagagtcagg                                                    20

<210> SEQ ID NO 82
<211> LENGTH: 20
<212> TYPE: DNA
<213> ORGANISM: Artificial
<220> FEATURE:
<223> OTHER INFORMATION: PCR primer

<400> SEQUENCE: 82
gtgggccggc atgatgatag                                                    20

<210> SEQ ID NO 83
<211> LENGTH: 27
<212> TYPE: DNA
<213> ORGANISM: Artificial
<220> FEATURE:
<223> OTHER INFORMATION: probe

<400> SEQUENCE: 83
cttcaaatgt gcaatccatg gctccgt                                            27
```

```
<210> SEQ ID NO 84
<211> LENGTH: 19
<212> TYPE: DNA
<213> ORGANISM: Artificial
<220> FEATURE:
<223> OTHER INFORMATION: PCR primer

<400> SEQUENCE: 84
gtagcgtctg cacgcccta                                               19

<210> SEQ ID NO 85
<211> LENGTH: 22
<212> TYPE: DNA
<213> ORGANISM: Artificial
<220> FEATURE:
<223> OTHER INFORMATION: PCR primer

<400> SEQUENCE: 85
cttggttgtt gatgagctgg ag                                           22

<210> SEQ ID NO 86
<211> LENGTH: 20
<212> TYPE: DNA
<213> ORGANISM: Artificial
<220> FEATURE:
<223> OTHER INFORMATION: PCR primer

<400> SEQUENCE: 86
aagctgtcgg ggtagcgtct                                              20

<210> SEQ ID NO 87
<211> LENGTH: 20
<212> TYPE: DNA
<213> ORGANISM: Artificial
<220> FEATURE:
<223> OTHER INFORMATION: PCR primer

<400> SEQUENCE: 87
aggctcgagt aacccagcac                                              20

<210> SEQ ID NO 88
<211> LENGTH: 25
<212> TYPE: DNA
<213> ORGANISM: Artificial
<220> FEATURE:
<223> OTHER INFORMATION: probe

<400> SEQUENCE: 88
acttagccgc ttcaagcccg atgtg                                        25

<210> SEQ ID NO 89
<211> LENGTH: 18
<212> TYPE: DNA
<213> ORGANISM: Artificial
<220> FEATURE:
<223> OTHER INFORMATION: PCR primer

<400> SEQUENCE: 89
agaaggtgcc cgagtggc                                                18

<210> SEQ ID NO 90
<211> LENGTH: 21
<212> TYPE: DNA
<213> ORGANISM: Artificial
<220> FEATURE:
<223> OTHER INFORMATION: PCR primer
```

```
<400> SEQUENCE: 90
ccccagatac ctgatccatg a                                             21

<210> SEQ ID NO 91
<211> LENGTH: 20
<212> TYPE: DNA
<213> ORGANISM: Artificial
<220> FEATURE:
<223> OTHER INFORMATION: PCR primer

<400> SEQUENCE: 91
cagtaggctc catggatggc                                               20

<210> SEQ ID NO 92
<211> LENGTH: 20
<212> TYPE: DNA
<213> ORGANISM: Artificial
<220> FEATURE:
<223> OTHER INFORMATION: PCR primer

<400> SEQUENCE: 92
atgaccttag caccccggtg                                               20

<210> SEQ ID NO 93
<211> LENGTH: 25
<212> TYPE: DNA
<213> ORGANISM: Artificial
<220> FEATURE:
<223> OTHER INFORMATION: hLCE-5BBamHI

<400> SEQUENCE: 93
ggatccaaca tgtcagtgtt gactt                                         25

<210> SEQ ID NO 94
<211> LENGTH: 25
<212> TYPE: DNA
<213> ORGANISM: Artificial
<220> FEATURE:
<223> OTHER INFORMATION: hLCE-3XhoI

<400> SEQUENCE: 94
ctcgagctat tcagctttcg ttgtt                                         25

<210> SEQ ID NO 95
<211> LENGTH: 22
<212> TYPE: DNA
<213> ORGANISM: Artificial
<220> FEATURE:
<223> OTHER INFORMATION: hLCE-F4

<400> SEQUENCE: 95
aacatgtcag tgttgacttt ac                                            22

<210> SEQ ID NO 96
<211> LENGTH: 20
<212> TYPE: DNA
<213> ORGANISM: Artificial
<220> FEATURE:
<223> OTHER INFORMATION: hLCE-510S

<400> SEQUENCE: 96
gtgctcttcg aactggtgct                                               20

<210> SEQ ID NO 97
<211> LENGTH: 20
```

```
<212> TYPE: DNA
<213> ORGANISM: Artificial
<220> FEATURE:
<223> OTHER INFORMATION: T7

<400> SEQUENCE: 97
taatacgact cactataggg                                                    20

<210> SEQ ID NO 98
<211> LENGTH: 24
<212> TYPE: DNA
<213> ORGANISM: Artificial
<220> FEATURE:
<223> OTHER INFORMATION: C99A

<400> SEQUENCE: 98
ccctggtcgg caactgactg cttc                                               24

<210> SEQ ID NO 99
<211> LENGTH: 24
<212> TYPE: DNA
<213> ORGANISM: Artificial
<220> FEATURE:
<223> OTHER INFORMATION: C225A

<400> SEQUENCE: 99
gtgagagtgg gcctggtcat gctg                                               24

<210> SEQ ID NO 100
<211> LENGTH: 22
<212> TYPE: DNA
<213> ORGANISM: Artificial
<220> FEATURE:
<223> OTHER INFORMATION: H141A

<400> SEQUENCE: 100
gtgataccag gccaggaaga tc                                                 22

<210> SEQ ID NO 101
<211> LENGTH: 21
<212> TYPE: DNA
<213> ORGANISM: Artificial
<220> FEATURE:
<223> OTHER INFORMATION: H144A

<400> SEQUENCE: 101
gtgatgtggg cataccagtg c                                                  21

<210> SEQ ID NO 102
<211> LENGTH: 22
<212> TYPE: DNA
<213> ORGANISM: Artificial
<220> FEATURE:
<223> OTHER INFORMATION: H145A

<400> SEQUENCE: 102
cacagtgatg gcgtgatacc ag                                                 22

<210> SEQ ID NO 103
<211> LENGTH: 22
<212> TYPE: DNA
<213> ORGANISM: Artificial
<220> FEATURE:
<223> OTHER INFORMATION: H174A

<400> SEQUENCE: 103
```
catcacggcg gccacgccat ag                                              22

<210> SEQ ID NO 104
<211> LENGTH: 265
<212> TYPE: PRT
<213> ORGANISM: Homo sapiens

<400> SEQUENCE: 104

```
Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Val Tyr Ile Leu Met Thr Lys Gly Leu Lys Gln
                85                  90                  95

Ser Val Cys Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Val Asn Tyr Leu Val Phe Cys Trp Met Gln His Asp Gln
    210                 215                 220

Cys His Ser His Phe Gln Asn Ile Phe Trp Ser Ser Leu Met Tyr Leu
225                 230                 235                 240

Ser Tyr Leu Val Leu Phe Cys His Phe Phe Glu Ala Tyr Ile Gly
                245                 250                 255

Lys Met Arg Lys Thr Thr Lys Ala Glu
            260                 265
```

<210> SEQ ID NO 105
<211> LENGTH: 265
<212> TYPE: PRT
<213> ORGANISM: Artificial
<220> FEATURE:
<223> OTHER INFORMATION: hLCE(C99A)

<400> SEQUENCE: 105

```
Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45
```

```
His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
 65                  70                  75                  80

Thr Gly Ala Tyr Met Val Tyr Ile Leu Met Thr Lys Gly Leu Lys Gln
                 85                  90                  95

Ser Val Ala Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
            115                 120                 125

Phe Ile Ile Leu Arg Lys Gln Lys Leu Ile Phe Leu His Trp Tyr His
            130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
            195                 200                 205

Gly Cys Val Val Asn Tyr Leu Val Phe Cys Trp Met Gln His Asp Gln
210                 215                 220

Cys His Ser His Phe Gln Asn Ile Phe Trp Ser Ser Leu Met Tyr Leu
225                 230                 235                 240

Ser Tyr Leu Val Leu Phe Cys His Phe Phe Glu Ala Tyr Ile Gly
            245                 250                 255

Lys Met Arg Lys Thr Thr Lys Ala Glu
            260                 265

<210> SEQ ID NO 106
<211> LENGTH: 265
<212> TYPE: PRT
<213> ORGANISM: Artificial
<220> FEATURE:
<223> OTHER INFORMATION: hLCE(C225A)

<400> SEQUENCE: 106

Met Asn Met Ser Val Leu Thr Leu Gln Glu Tyr Glu Phe Glu Lys Gln
 1               5                  10                  15

Phe Asn Glu Asn Glu Ala Ile Gln Trp Met Gln Glu Asn Trp Lys Lys
                20                  25                  30

Ser Phe Leu Phe Ser Ala Leu Tyr Ala Ala Phe Ile Phe Gly Gly Arg
            35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
 65                  70                  75                  80

Thr Gly Ala Tyr Met Val Tyr Ile Leu Met Thr Lys Gly Leu Lys Gln
                 85                  90                  95

Ser Val Cys Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
            115                 120                 125

Phe Ile Ile Leu Arg Lys Gln Lys Leu Ile Phe Leu His Trp Tyr His
            130                 135                 140
```

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Val Asn Tyr Leu Val Phe Cys Trp Met Gln His Asp Gln
    210                 215                 220

Ala His Ser His Phe Gln Asn Ile Phe Trp Ser Ser Leu Met Tyr Leu
225                 230                 235                 240

Ser Tyr Leu Val Leu Phe Cys His Phe Phe Glu Ala Tyr Ile Gly
                245                 250                 255

Lys Met Arg Lys Thr Thr Lys Ala Glu
            260                 265

<210> SEQ ID NO 107
<211> LENGTH: 265
<212> TYPE: PRT
<213> ORGANISM: Artificial
<220> FEATURE:
<223> OTHER INFORMATION: hLCE(H141A)

<400> SEQUENCE: 107

Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Val Tyr Ile Leu Met Thr Lys Gly Leu Lys Gln
                85                  90                  95

Ser Val Cys Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu Ala Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Val Asn Tyr Leu Val Phe Cys Trp Met Gln His Asp Gln
    210                 215                 220

Cys His Ser His Phe Gln Asn Ile Phe Trp Ser Ser Leu Met Tyr Leu
225                 230                 235                 240

Ser Tyr Leu Val Leu Phe Cys His Phe Phe Glu Ala Tyr Ile Gly
            245                 250                 255

Lys Met Arg Lys Thr Thr Lys Ala Glu
            260                 265

<210> SEQ ID NO 108
<211> LENGTH: 265
<212> TYPE: PRT
<213> ORGANISM: Artificial
<220> FEATURE:
<223> OTHER INFORMATION: hLCE(H144A)

<400> SEQUENCE: 108

Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Val Tyr Ile Leu Met Thr Lys Gly Leu Lys Gln
                85                  90                  95

Ser Val Cys Asp Gln Gly Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr Ala
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Val Asn Tyr Leu Val Phe Cys Trp Met Gln His Asp Gln
    210                 215                 220

Cys His Ser His Phe Gln Asn Ile Phe Trp Ser Ser Leu Met Tyr Leu
225                 230                 235                 240

Ser Tyr Leu Val Leu Phe Cys His Phe Phe Glu Ala Tyr Ile Gly
            245                 250                 255

Lys Met Arg Lys Thr Thr Lys Ala Glu
            260                 265

<210> SEQ ID NO 109
<211> LENGTH: 265
<212> TYPE: PRT
<213> ORGANISM: Artificial
<220> FEATURE:
<223> OTHER INFORMATION: hLCE(H145A)

<400> SEQUENCE: 109

Met Asn Met Ser Val Leu Thr Leu Gln Glu Tyr Glu Phe Glu Lys Gln

```
                1               5                  10                 15
Phe Asn Glu Asn Glu Ala Ile Gln Trp Met Gln Glu Asn Trp Lys Lys
                20                 25                 30

Ser Phe Leu Phe Ser Ala Leu Tyr Ala Ala Phe Ile Phe Gly Gly Arg
            35                 40              45

His Leu Met Asn Lys Arg Ala Lys Phe Glu Leu Arg Lys Pro Leu Val
        50              55              60

Leu Trp Ser Leu Thr Leu Ala Val Phe Ser Ile Phe Gly Ala Leu Arg
65              70              75              80

Thr Gly Ala Tyr Met Val Tyr Ile Leu Met Thr Lys Gly Leu Lys Gln
                85              90              95

Ser Val Cys Asp Gln Gly Phe Tyr Asn Gly Pro Val Ser Lys Phe Trp
            100             105             110

Ala Tyr Ala Phe Val Leu Ser Lys Ala Pro Glu Leu Gly Asp Thr Ile
        115             120             125

Phe Ile Ile Leu Arg Lys Gln Lys Leu Ile Phe His Trp Tyr His
        130             135             140

Ala Ile Thr Val Leu Leu Tyr Ser Trp Tyr Ser Tyr Lys Asp Met Val
145             150             155             160

Ala Gly Gly Gly Trp Phe Met Thr Met Asn Tyr Gly Val His Ala Val
                165             170             175

Met Tyr Ser Tyr Tyr Ala Leu Arg Ala Ala Gly Phe Arg Val Ser Arg
            180             185             190

Lys Phe Ala Met Phe Ile Thr Leu Ser Gln Ile Thr Gln Met Leu Met
        195             200             205

Gly Cys Val Val Asn Tyr Leu Val Phe Cys Trp Met Gln His Asp Gln
    210             215             220

Cys His Ser His Phe Gln Asn Ile Phe Trp Ser Ser Leu Met Tyr Leu
225             230             235             240

Ser Tyr Leu Val Leu Phe Cys His Phe Phe Glu Ala Tyr Ile Gly
            245             250             255

Lys Met Arg Lys Thr Thr Lys Ala Glu
        260             265
```

<210> SEQ ID NO 110
<211> LENGTH: 265
<212> TYPE: PRT
<213> ORGANISM: Artificial
<220> FEATURE:
<223> OTHER INFORMATION: hLCE(H174A)

<400> SEQUENCE: 110

```
Met Asn Met Ser Val Leu Thr Leu Gln Glu Tyr Glu Phe Glu Lys Gln
1               5                  10                 15

Phe Asn Glu Asn Glu Ala Ile Gln Trp Met Gln Glu Asn Trp Lys Lys
                20                 25                 30

Ser Phe Leu Phe Ser Ala Leu Tyr Ala Ala Phe Ile Phe Gly Gly Arg
            35                 40              45

His Leu Met Asn Lys Arg Ala Lys Phe Glu Leu Arg Lys Pro Leu Val
        50              55              60

Leu Trp Ser Leu Thr Leu Ala Val Phe Ser Ile Phe Gly Ala Leu Arg
65              70              75              80

Thr Gly Ala Tyr Met Val Tyr Ile Leu Met Thr Lys Gly Leu Lys Gln
                85              90              95

Ser Val Cys Asp Gln Gly Phe Tyr Asn Gly Pro Val Ser Lys Phe Trp
```

-continued

```
                100                     105                      110
Ala Tyr Ala Phe Val Leu Ser Lys Ala Pro Glu Leu Gly Asp Thr Ile
        115                     120                      125

Phe Ile Ile Leu Arg Lys Gln Lys Leu Ile Phe Leu His Trp Tyr His
        130                     135                      140

His Ile Thr Val Leu Leu Tyr Ser Trp Tyr Ser Tyr Lys Asp Met Val
145                     150                     155                      160

Ala Gly Gly Gly Trp Phe Met Thr Met Asn Tyr Gly Val Ala Ala Val
                165                     170                      175

Met Tyr Ser Tyr Tyr Ala Leu Arg Ala Ala Gly Phe Arg Val Ser Arg
            180                     185                      190

Lys Phe Ala Met Phe Ile Thr Leu Ser Gln Ile Thr Gln Met Leu Met
        195                     200                      205

Gly Cys Val Val Asn Tyr Leu Val Phe Cys Trp Met Gln His Asp Gln
        210                     215                      220

Cys His Ser His Phe Gln Asn Ile Phe Trp Ser Ser Leu Met Tyr Leu
225                     230                     235                      240

Ser Tyr Leu Val Leu Phe Cys His Phe Phe Glu Ala Tyr Ile Gly
                245                     250                      255

Lys Met Arg Lys Thr Thr Lys Ala Glu
                260                     265
```